(12) United States Patent
Marfat

(10) Patent No.: US 6,716,978 B2
(45) Date of Patent: *Apr. 6, 2004

(54) THERAPEUTICALLY ACTIVE COMPOUNDS BASED ON INDAZOLE BIOISOSTERE REPLACEMENT OF CATECHOL IN PDE4 INHIBITORS

(75) Inventor: Anthony Marfat, Mystic, CT (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,446

(22) PCT Filed: Oct. 9, 1998

(86) PCT No.: PCT/IB98/01579
§ 371 (c)(1),
(2), (4) Date: Sep. 20, 1999

(87) PCT Pub. No.: WO99/23076
PCT Pub. Date: May 14, 1999

(65) Prior Publication Data
US 2002/0058687 A1 May 16, 2002

Related U.S. Application Data
(60) Provisional application No. 60/064,160, filed on Nov. 4, 1997.

(51) Int. Cl.[7] ............................................. C07D 231/56
(52) U.S. Cl. .................. 540/575; 544/251; 544/363; 544/371; 548/361.1; 548/362.5
(58) Field of Search ............................... 514/405, 228.2, 514/230.5, 234.5, 241, 243, 252.06, 254.06, 255.06, 259, 266, 297, 300, 306, 310, 322, 362, 364, 367, 365, 372, 374, 379, 381; 548/361.1, 362.5

(56) References Cited

U.S. PATENT DOCUMENTS 5,958,953 A * 9/1999 Marfat ........................ 514/333
6,040,329 A * 3/2000 Marfat ........................ 514/405
6,127,398 A * 10/2000 Marfat ........................ 514/403
6,211,222 B1 * 4/2001 Marfat ........................ 514/403
6,262,040 B1 * 7/2001 Marfat ........................ 514/158
6,391,872 B1 * 5/2002 Marfat ........................ 514/218

OTHER PUBLICATIONS

"Webster's New World Dictionary, College Ed." no author listed, World Publishing, 1962, p. 300.*

* cited by examiner

Primary Examiner—Richard L. Raymond
(74) Attorney, Agent, or Firm—Peter C. Richardson; Gregg C. Benson; Robert T. Ronau

(57) ABSTRACT

This application is directed to therapeutically active compositions of matter are useful for treating or preventing inflammatory bowel disease and conditions including joint inflammation, Crohn's disease and inflammatory bowel disease; respiratory diseases such as chronic obstructive pulmonary disease (COPD) including asthma, chronic bronchitis, and pulmonary emphysema; infectious diseases including endotoxic shock and toxic shock syndrome; immune diseases including systemic lupus erythematosis and psoriasis; and other diseases including bone resorption diseases and reperfusion injury; wherein said composition of matter comprises a compound which is an inhibitor of phosphodiesterase isozyme 4 (PDE4) and wherein an indazole is one essential component of said compound's overall chemical structure, and wherein said indazole constitutes a bioisosteric replacement of a catechol component or functional derivative thereof in a known compound having the same said therapeutic activity and the same remaining said components of its overall chemical structure. Included are compounds of Formula (IA) or (IB):

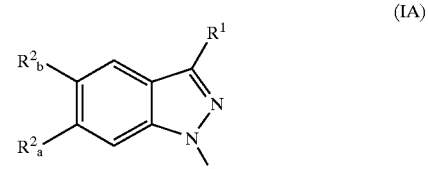

(IA)

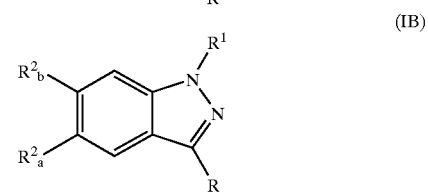

(IB)

wherein the variable are defined as set forth in the specification.

11 Claims, No Drawings

THERAPEUTICALLY ACTIVE COMPOUNDS BASED ON INDAZOLE BIOISOSTERE REPLACEMENT OF CATECHOL IN PDE4 INHIBITORS

This application is a 371 of PCT/IB98/01579, filed Oct. 9, 1998 and claims priority to U.S Provisional Application No. 60/064,160, filed Nov. 4, 1997.

FIELD OF THE INVENTION

The present invention is in the field of compositions of matter, and pharmaceutical compositions and methods of treatment utilizing one or more of said compositions of matter as the active ingredient and the active agent with respect thereto, wherein said composition of matter comprises an indazole as an essential feature of its overall chemical structure, said indazole constituting a bioisosteric replacement of a catechol or functional derivative thereof.

The catechol-containing as well as the indazole-based compositions of matter have biological activity as selective inhibitors of phosphodiesterase (PDE) type IV and the production of tumor necrosis factor (TNF), and as such are useful in the treatment of asthma, chronic obstructive pulmonary disease (COPD), psoriasis, allergic rhinitis, dermatitis, Crohn's disease, arthritis, and other inflammatory diseases, AIDS, septic shock and other diseases involving the production of TNF. This invention also relates to a method of using such compounds in the treatment of the foregoing diseases in mammals, especially humans, and to pharmaceutical compositions containing such compounds.

BACKGROUND OF THE INVENTION

Since the recognition that cyclic adenosine phosphate (AMP) is an intracellular second messenger, E. W. Sutherland, and T. W. Rall, Pharmacol. Rev., 12, 265, (1960), inhibition of the phosphodiesterases has been a target for modulation and, accordingly, therapeutic intervention in a range of disease processes. More recently, distinct classes of PDE have been recognized, J. A. Beavo et al., TiPS, 11, 150, (1990), and their selective inhibition has led to improved drug therapy, C. D. Nicholson, M. S. Hahid, TiPS, 12, 19, (1991). More particularly, it has been recognized that inhibition of PDE type IV can lead to inhibition of inflammatory mediator release, M. W. Verghese et al., J. Mol. Cell Cardiol., 12 (Suppl. II), S 61, (1989) and airway smooth muscle relaxation (T. J. Torphy in "Directions for New Anti-Asthma Drugs," eds S. R. O'Donnell and C. G. A. Persson, 1988, 37 Birkhauser-Verlag). Thus, compounds that inhibit PDE type IV, but which have poor activity against other PDE types, would inhibit the release of inflammatory mediators and relax airway smooth muscle without causing cardiovascular effects or antiplatelet effects.

TNF is recognized to be involved in many infectious and auto-immune diseases, W. Friers, FEBS Letters, 285, 199, (1991). Furthermore, it has been shown that TNF is the prime mediator of the inflammatory response seen in sepsis and septic shock, C. E. Spooner et al., Clinical Immunology and Immunopathology, 62, S11, (1992). The role of these mediators in the pathogenesis of Crohn's disease is discussed in Van Hogezand, R. A. and Verspaget, H. W., Drugs, 56(3), 299–305 (1998).

The present invention is concerned with the discovery that the indazole nucleus is a moiety which is capable of being a bioisostere replacement for the catechol moiety which is an essential part of endogenous ligands acting on phosphodiesterase-4 receptors and thereby carrying out essential metabolic functions in the body. The indazole nucleus is also a bioisostere replacement for the catechol moiety which is an essential part of numerous drugs which have been and in the future will be created and developed for therapeutic treatments as detailed further herein. This bioisostere replacement will be better understood from the following structural representation of the catechol moiety and the indazole moiety which replaces it:

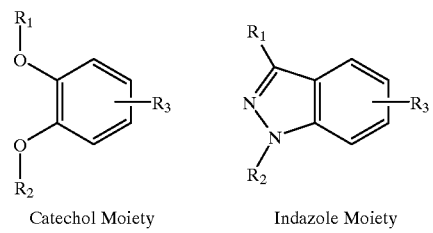

Catechol Moiety       Indazole Moiety

The terms "bioisostere", "bioisosteric replacement", "bioisosterism" and closely related terms as used herein have the same meanings as those generally recognized in the art. Bioisosteres are atoms, ions, or molecules in which the peripheral layers of electrons can be considered identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Bioisosterism arises from a reasonable expectation that a proposed bioisosteric replacement will result in maintenance of similar biological properties. Such a reasonable expectation may be based on structural similarity alone. This is especially true in those cases where a number of particulars are known regarding the characteristic domains of the receptor, etc. involved, to which the bioisosteres are bound or which works upon said bioisosteres in some manner.

Phosphodiesterase-4 is a cAMP-specific phosphodiesterase which plays an important role in the regulation of inflammatory and immune cell activation. A significant variety of different structural types of compounds active as PDE-4 inhibitors has been reported, and PDE isozymes have been characterized in cardiac muscle, and airway and arterial smooth muscles. Attention has also been focused on a high-affinity allosteric binding site which is abundant in brain PDE4 isozyme, whose differential modulation relative to the cAMP catalytic site has yielded drugs with greater therapeutic utility. Rolipram, which contains catechol as a key part of its overall chemical structure, is representative of this type of PDE4 inhibitor and may be depicted as follows:

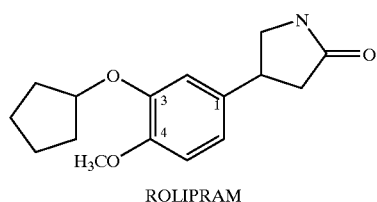

ROLIPRAM

Accordingly, there is disclosed herein a substantial number of indazole-containing compositions of matter which are PDE4 inhibitors and which are the result of a bioisostere replacement of catechol from a compound which originally contained said catechol moiety and which also had PDE4 inhibitor activity. However, there is also disclosed herein a number of catechol-containing compounds which are PDE4 inhibitors and which are also suitable to be subjected to indazole bioisostere replacement in accordance with the present invention. These latter compounds are claimed both as novel indazole compositions of matter and as the products of indazole bioisostere replacement in accordance with the present invention.

SUMMARY OF THE INVENTION

The present invention relates to compounds having therapeutic usefulness based on their activity as phosphodiesterase-4 inhibitors, comprising an indazole as one essential component of their overall chemical structure, wherein said indazole constitutes a bioisosteric replacement of a catechol component or functional derivative thereof in a known compound or compounds having the same said therapeutic usefulness based on possession of phosphodiesterase-4 inhibitor activity, as well as having the same remaining said components which make up the overall chemical structure of the compound(s) involved.

In particular, the present invention relates to the above-described compounds which are therapeutically useful in treating or preventing asthma.

The present invention thus also relates to an improved method of treating asthma using a known compound having a catechol moiety or functional derivative thereof as one essential component of its overall chemical structure; wherein the improvement consists of using a compound having an indazole moiety as one essential component of its overall chemical structure and having the same remaining said components of its overall chemical structure, wherein said indazole moiety constitutes a bioisosteric replacement for said catechol moiety.

The present invention further relates to a compound (a) useful as a therapeutically active agent in a therapeutically effective amount for a method of treating or preventing; and (b) useful as an active ingredient in a pharmaceutical composition for treating or preventing: one or members selected from the groups of diseases and conditions consisting essentially of (1) inflammatory comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory comprising: acute respiratory distress syndrome, chronic obstructive pulmonary disease (COPD) including asthma, chronic bronchitis and pulmonary emphysema, and silicosis; (3) infectious comprising: sepsis, septic shock, endotoxic shock, gram negative sepsis, toxic shock syndrome, fever and myalgias due to bacterial, viral or fungal infection, and influenza; (4) immune comprising: autoimmune diabetes, systemic lupus erythematosis, graft vs. host reaction, allograft rejections, multiple sclerosis, psoriasis, and allergic rhinitis; and (5) general comprising: bone resorption diseases; reperfusion injury; cachexia secondary to infection or malignancy; cachexia secondary to human acquired immune deficiency syndrome (AIDS), human immunodeficiency virus (HIV) infectioin, or AIDS related complex (ARC); keloid formation; scar tissue formation; type 1 diabetes mellitus; and leukemia; wherein said compound comprises an inhibitor of phosphodiesterase isozyme 4 (PDE4) and wherein an indazole is one essential component of said compound's overall chemical structure, and wherein said indazole constitutes a bioisosteric replacement of a catechol component or functional derivative thereof in a known compound having the same said one or more types of therapeutic activity and the same remaining said components of its overall chemical structure.

Especially important among the above-recited diseases and conditions which may be treated or prevented using the compounds of the present invention are the inflammatory diseases and conditions and the respiratory diseases and conditions. Among the inflammatory diseases and conditions which are especially significant with regard to successful treatment or prevention using the compounds of the present invention comprise: joint inflammation, rheumatoid arthritis, osteoarthritis, and inflammatory bowel disease. Among the respiratory diseases and conditions which are especially significant with regard to successful treatment or prevention using the compounds of the present invention comprise: asthma, acute respiratory distress syndrome, and bronchitis.

The present invention relates to novel compositions of matter and to therapeutic agents and active ingredients useful in treating or preventing one or members selected from the groups of diseases and conditions as above-described, comprising a compound of Formula (IA) or (IB):

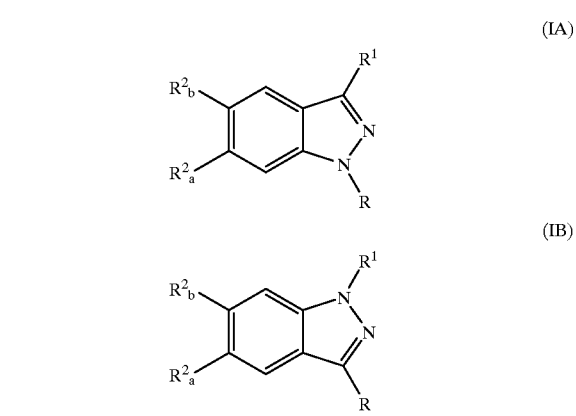

and to pharmaceutically acceptable salts thereof, wherein:

R is a member independently selected from the group consisting essentially of hydrogen, $(C_1-C_9)$alkyl; —$(CH_2)_n(C_3-C_{10})$ cycloalkyl wherein n is an integer selected from 0, 1, and 2; $(C_1-C_6)$alkoxy$(C_1-C_6)$alkyl; —$(C_2-C_6)$alkenyl; —$(CH_2)_n(C_3-C_9)$ heterocyclyl wherein n is an integer selected from 0, 1, and 2; and —$(Z^1)_b(Z^2)_c(C_6-C_{10})$ aryl wherein b and c are integers independently selected from 0 and 1, $Z^1$ is $(C_1-C_6)$ alkylene or $(C_2-C_6)$ alkenylene, and $Z^2$ is O, S, $SO_2$, or $NR^{119}$; and further wherein said heterocyclyl is a member independently selected from the group consisting essentially of acridinyl; benzimidazolyl; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl;

pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; wherein said aryl is a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; wherein said alkyl, alkenyl, alkoxyalkyl, heterocyclyl, and aryl moieties defining said R groups are substituted by 0 to 3 substituents where each said substituent comprises a member independently selected from the group consisting essentially of bromo, chloro, or fluoro; hydroxy; $(C_1-C_5)$ alkyl; $(C_2-C_5)$ alkenyl; $(C_1-C_5)$ alkoxy; $(C_3-C_6)$ cycloalkoxy; mono-, di-, and tri-fluoromethyl; nitro; —C(=O)OR$^{119}$, —C(=O)NR$^{119}$R$^{120}$, —NR$^{119}$R$^{120}$ and —S(=O)$_2$ NR$^{119}$R$^{120}$;

R$^1$ is a member independently selected from the group consisting essentially of hydrogen; $(C_1-C_9)$alkyl; $(C_2-C_3)$alkenyl; phenyl; $(C_3-C_7)$cycloalkyl; and $(C_3-C_7)$ cycloalkyl$(C_1-C_2)$alkyl; wherein said alkyl, alkenyl and phenyl moieties defining said R$^1$ groups are substituted by 0 to 3 substituents where each said substituent comprises a member independently selected from the group consisting essentially of methyl; ethyl; mono-, di-, and tri-fluoromethyl; and bromo, chloro, or fluoro; and R$^2_a$ and R$^2_b$ are independently selected from the group consisting essentially of hydrogen and hereinafter recited substituents, provided that one, but not both of R$^2_a$ and R$^2_b$ must be independently selected as hydrogen, wherein said substituents comprise moieties of the groups (I) through (V) summarized below, including those of the partial Formulas therein set out, all as defined in detail herein:

I a moiety of partial Formulas (IC), (ID), (IE), or (IF):

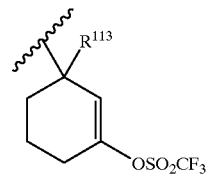
(IC)

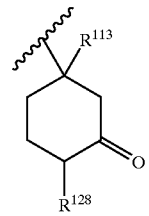
(ID)

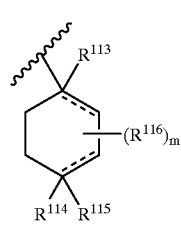
(IE)

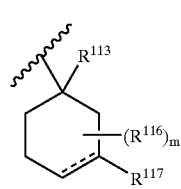
(IF)

II a member selected from the group consisting essentially of R$^{229}$; —C(=O)NR$^{222}$(CHR$^{222}$)$_m$C(=O)NR$^{222}$O(CH$_2$)$_q$(C$_6$-C$_{10}$)aryl); —C(=NR$^{242}$)NH(CH$_2$)$_p$(C$_6$-C$_{10}$) aryl; —C(=O)NR$^{218}$(CHR$^{222}$)$_m$C(=O)NR$^{222}$(CH$_2$)$_p$OR$^{222}$; —C(=O)NR$^{222}$(CHR$^{222}$)$_m$S(C$_1$-C$_4$) alkyl; —C[=NOC(=O)R$^{235}$]R$^{236}$; —CR$^{227}$R$^{228}$CHR$^{238}$NR$^{219}$SO$_2$(CH$_2$)$_p$A; —CR$^{227}$R$^{228}$CHR$^{238}$NR$^{219}$P(=O)(OR$^{222}$)C(=O)(C$_1$-C$_4$)alkyl; —CR$^{227}$R$^{238}$CHR$^{238}$NR$^{219}$P(=O)[(C$_1$-C$_4$) alkoxy]$_2$, —Z$^3$—R$^{217}$; and —(CR$^{227}$R$^{228}$)$_m$NR$^{219}$(C(O))$_q$R$^{220}$ wherein p is an integer selected from 0, 1, and 2; m is an integer selected from 1, 2, 3, 4, 5, and 6; and q is an integer selected from 1 and 2;

—OR, a moiety of partial Formulas (IIA) through (III), inclusive:

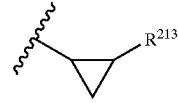
(IIA)

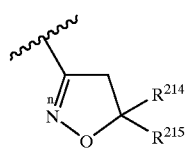
(IIB)

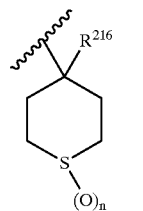
(IIC)

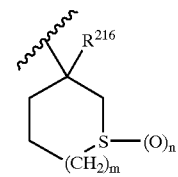
(IID)

-continued (IIE) 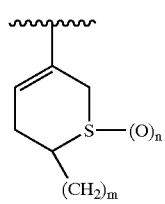

(IIF) 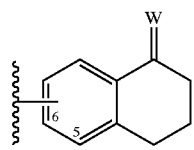

(IIG) 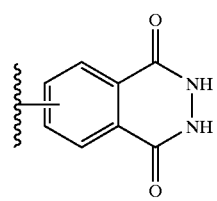

(IIIA) 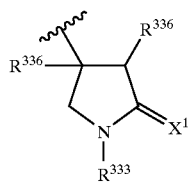

(IIIC) 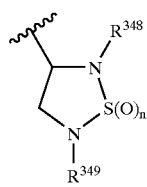

(IIIE) 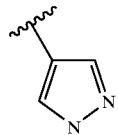

(IIIG) 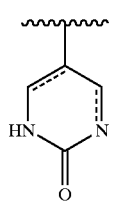

(IIII) 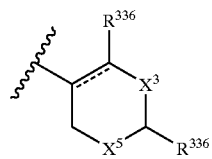

-continued (IIH) 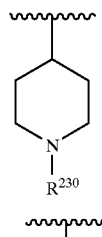

(III) 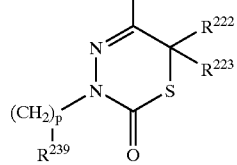

III a member independently selected from the group consisting essentially of 2-oxo-4-pyrrolyl; pyrazolyl; 2-oxo-3,4-dihydro-5-pyrimidyl; 2-oxo-3,4-dihydro4-pyrimidyl; 2-oxo-tetrahydro-4-pyrimidyl; 2-oxo-tetrahyro-5-pyrimidyl; 2-oxo4-pyrimidyl; and 2-oxo-5-pyrimidyl; wherein each of said $R^2_a$ and $R^2_b$ groups is substituted by 0, 1, 2, 3, or 4 $R^{236}$ groups;

—OR, a moiety of partial Formulas (IIIA) through (III), inclusive:

(IIIB) 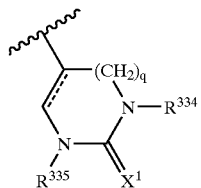

(IIID) 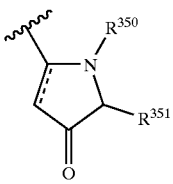

(IIIF) 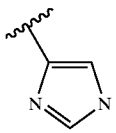

(IIIH) 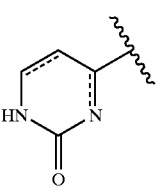

(IIIJ) 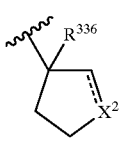

-continued
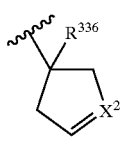
(IIIK)
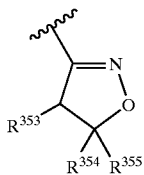
(IIIL)
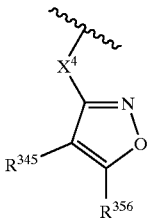
(IIIM)
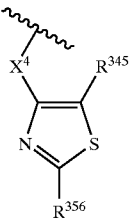
(IIIN)
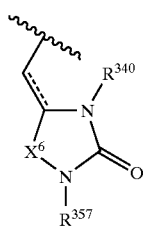
(IIIO)
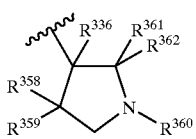
(IIIP)
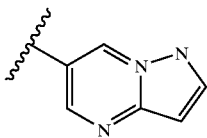
(IIIQ)
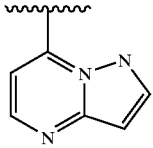
(IIIR)
(IIIS)
(IIIT)
IV
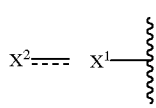
(IV)
a moiety of partial Formulas (VA) through (VM), inclusive:
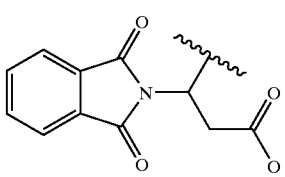
(VA)
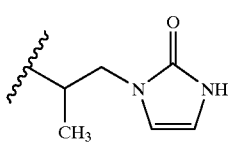
(VB)

-continued
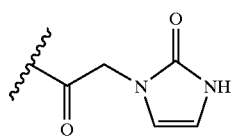
(VC)
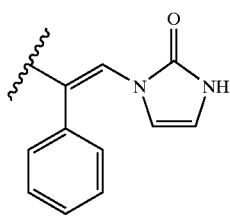
(VD)
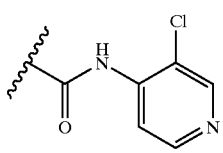
(VE_a)
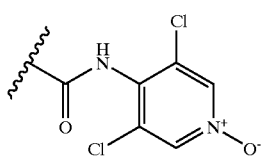
(VE)
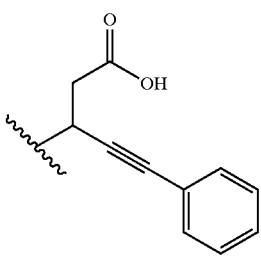
(VF)
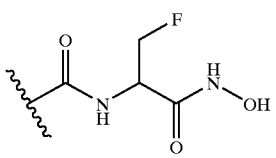
(VG)
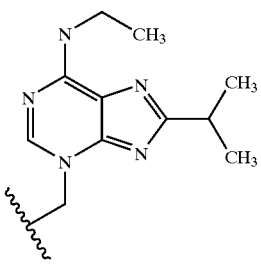
(VH)
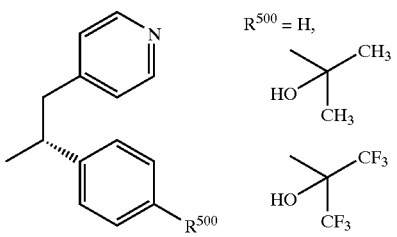
(VI) $R^{500}$ = H,
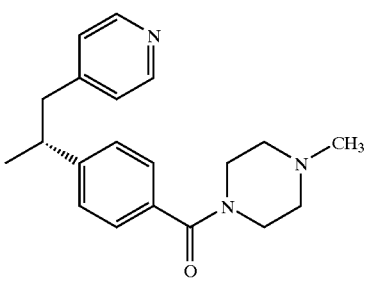
(VJ)
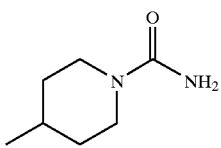
(VK)
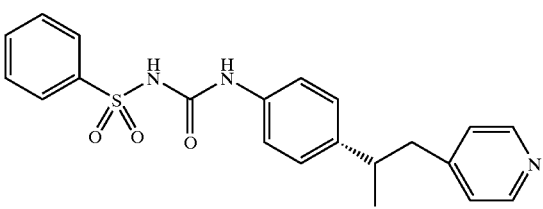
(VL)
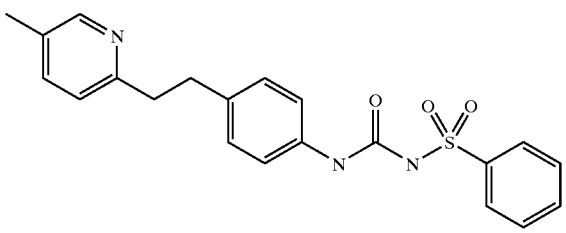
(VM)

DETAILED DESCRIPTION OF THE INVENTION

The present invention relates to a novel class of therapeutically active compositions of matter and member species thereof comprising indazole-containing compounds having PDE4 inhibitory activity which are produced by an indazole-for-catechol bioisostere replacement. In particular, the novel compositions of matter of the present invention comprise a compound of Formula (IA) or (IB):

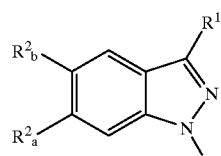
(IA)

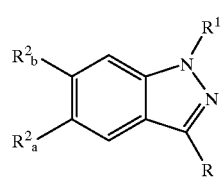
(IB)

and to pharmaceutically acceptable salts thereof, wherein:

R is a member independently selected from the group consisting essentially of hydrogen, $(C_1-C_9)$alkyl; $-(CH_2)_n(C_3-C_{10})$cycloalkyl wherein n is an integer selected from 0, 1, and 2; $(C_1-C_6)$alkoxy$(C_1-C_6)$alkyl; $(C_2-C_6)$alkenyl; $-(CH_2)_n(C_3-C_9)$heterocyclyl wherein n is an integer selected from 0, 1, and 2; and $-(Z^1)_b(Z^2)_c(C_6-C_{10})$aryl wherein b and c are integers independently selected from 0 and 1, $Z^1$ is $(C_1-C_6)$ alkylene or $(C_2-C_6)$ alkenylene, and $Z^2$ is O, S, $SO_2$, or $NR^{119}$; and further wherein said heterocyclyl is a member independently selected from the group consisting essentially of acridinyl; benzimidazolyl; benzodioxolane; 1,3-benzodioxol-5-yl; benzoblbfuranyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; soquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; wherein said aryl is a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; wherein said alkyl, alkenyl, alkoxyalkyl, heterocyclyl, and aryl moieties defining said R groups are substituted by 0 to 3 substituents where each said substituent comprises a member independently selected from the group consisting essentially of bromo, chloro, or fluoro; hydroxy; $(C_1-C_5)$alkyl; $(C_2-C_5)$alkenyl; $(C_1-C_5)$alkoxy; $(C_3-C_6)$cycloalkoxy; mono-, di-, and tri-fluoromethyl; nitro; $-C(=O)OR^{119}$, $-C(=O)NR^{119}R^{120}$, $-NR^{119}R^{120}$ and $-S(=O)_2NR^{119}R^{120}$;

$R^1$ is a member independently selected from the group consisting essentially of hydrogen; $(C_1-C_9)$ alkyl; $(C_2-C_3)$ alkenyl; phenyl; $(C_3-C_7)$ cycloalkyl; and $(C_3-C_7)$ cycloalkyl$(C_1-C_2)$ alkyl; wherein said alkyl, alkenyl and phenyl moieties defining said $R^1$ groups are substituted by 0 to 3 substituents where each said substituent comprises a member independently selected from the group consisting essentially of methyl; ethyl; mono-, di-, and tri-fluoromethyl; and bromo, chloro, or fluoro; and $R^2_a$ and $R^2_b$ are independently selected from the group consisting essentially of hydrogen and hereinafter recited substituents, provided that one, but not both of $R^2_a$ and $R^2_b$ must be independently selected as hydrogen, wherein said substituents comprise moieties of the groups (I) through (V):

I  a moiety of partial Formulas (IC), (ID), (IE), or (IF):

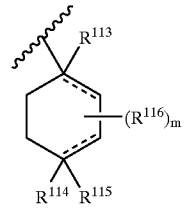
(IC)

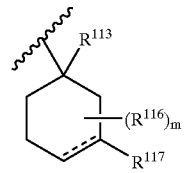
(ID)

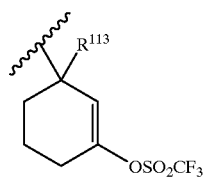
(IE)

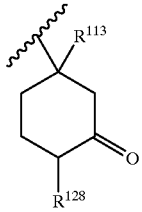
(IF)

wherein the dashed lines in formulas (IC) and (ID) independently and optionally represent a single or double bond, provided that in formula (IC) both dashed lines cannot both represent double bonds at the same time;

m is an integer selected from 0, 1, 2, 3, and 4, and when 2, may apply to a single carbon atom on the ring;

$R^{113}$ is a member selected from the group consisting essentially of H; bromo, chloro, or fluoro; cyano; $(C_2-C_4)$alkynyl substituted by 0 or 1 substituent where said substituent is a member selected from the group consisting essentially of phenyl, pyridyl and pyrimidinyl; $(C_1-C_4)$ alkyl substituted by 0 to 6 bromo, chloro, or fluoro; —$CH_2NHC(=O)C(=O)NH_2$; cyclopropyl substituted by 0 or 1 substituent where said substituent is a member selected from the group consisting essentially of $R^{121}$; $R^{127}$; $CH_2OR^{119}$; $NR^{119}R^{120}$; $CH_2NR^{119}R^{120}$; $C(=O)OR^{119}$; $C(=O)NR^{119}R^{120}$; $C\equiv CR_{11}$; $C(Z)H$; and —$CH=CR^{121}R^{121}$; provided that $R^{113}$ is H in Formula (IC) when the dashed line for the ring carbon of $R^{113}$ attachment represents a double bond;

$R^{114}$ is a member selected from the group consisting essentially of H; $R^{116}$; $C(Y)R^{124}$; $C(=O)OR^{124}$; $C(Y)NR^{127}R^{124}$; CN; $C(NR^{127})NR^{127}R^{124}$; $C(NOR^{119})R^{124}$; $C(=O)NR^{119}NR^{119}C(=O)R^{119}$; $C(=O)NR^{119}NR^{127}R^{124}$; $C(NOR^{124})R^{119}$; $C(NR^{119})NR^{127}R^{124}$; $C(NR^{124})NR^{119}R^{120}$; $C(NCN)NR^{127}R^{124}$; $C(NCN)S(C_1-C_4)$ alkyl; $CR^{119}R^{120}OR^{124}$, $CR^{119}R^{120}SR^{124}$, $CR^{119}R^{120}S(O)_nR^{125}$ where n is an integer selected from 0, 1, and 2; $CR^{119}R^{120}NR^{124}R^{127}$; $CR^{119}R^{120}NR^{127}S(=O)_2R_{15}$; $CR^{119}R^{120}NR^{127}C(Y)R^{124}$; $CR^{119}R^{120}NR^{127}C(=O)OR^{125}$; $CR^{119}R^{120}NR^{127}C(Y)NR^{127}R^{124}$; $CR^{119}R^{120}NR^{127}C(NCN)NR^{127}R^{124}$; $CR^{119}R^{120}NR^{127}C(CR^{119}NO_2)S(C_1-C_4)$alkyl; $CR^{119}R^{120}C(=O)OR^{125}$; $CR^{119}R^{120}C(Y)NR^{127}R^{124}$; $CR^{119}R^{120}C(NR^{127})NR^{127}R^{124}$; $CR^{119}R^{120}CN$; $CR^{119}R^{120}C(NOR^{120})R^{124}$; $CR^{119}R^{120}C(NOR^{124})R^{120}$; $CR^{119}R^{120}NR^{127}C(NR^{127})S(C_1-C_4)$ alkyl; $CR^{119}R^{120}NR^{127}C(NR^{127})NR^{127}R^{124}$; $CR^{119}R^{120}NR^{127}C(=O)C(=O)NR^{127}R^{124}$; $CR^{119}R^{120}NR^{127}C(=O)C(=O)OR^{24}$; tetrazolyl; thiazolyl; imidazolyl; imidazolidinyl; pyrazolyl; thiazolidinyl; oxazolyl; oxazolidinyl; triazolyl; isoxazolyl; oxadiazolyl; thiadiazolyl; $CR^{119}R^{120}$(tetrazolyl); $CR^{119}R^{120}$(thiazolyl); $CR^{119}R^{120}$(imidazolyl); $CR^{119}R^{120}$(imidazolidinyl); $CR^{119}R^{120}$(pyrazolyl); $CR^{119}R^{120}$(thiazolidinyl); $CR^{119}R^{120}$(oxadiazolyl); $CR^{119}R^{120}$(oxazolidinyl); $CR^{119}R^{120}$(triazolyl); $CR^{119}R^{120}$(isoxazolyl); $CR^{119}R^{120}$(oxadiazolyl); $CR^{119}R^{120}$(thiadiazolyl); $CR^{119}R^{120}$(morpholinyl); $CR^{119}R^{120}$(piperidinyl); $CR^{119}R^{120}$(piperazinyl); and $CR^{119}R^{120}$(pyrrolyl); said heterocyclic groups being substituted by 0 to 3 substituents $R^{124}$;

$R^{115}$ is a member selected from the group consisting essentially of $R^{119}$; $OR^{119}$; —$CH_2OR^{119}$; cyano; $C(=O)R^{119}$; $C(=O)OR^{119}$; $C(=O)NR^{119}R^{120}$; and $NR^{119}R^{120}$; provided that $R^{115}$ is absent when the dashed line in Formula (9.2) represents a double bond; or $R^{114}$ and $R^{115}$ are taken together to form =O or =$R^{118}$;

or $R^{115}$ is hydrogen and $R^{114}$ is $OR^{124}$; $SR^{124}$; $S(O)_nR^{125}$, where n is an integer selected from 0, 1, and 2; $S(=O)_2NR^{127}R^{124}$; $NR^{127}R^{124}$; $NR^{124}C(=O)R^{119}$; $NR^{127}C(Y)R^{124}$; $NR^{127}C(=O)OR^{125}$; $NR^{127}C(Y)NR^{127}R^{124}$; $NR^{127}S(=O)_2NR^{127}R^{124}$; $NR^{127}C(NCN)NR^{127}R^{124}$; $NR^{127}S(=O)_2R^{125}$; $NR^{127}C(CR^{119}NO_2)NR^{127}R^{124}$; $NR^{127}C(NCN)S(C_1-C_4)$ alkyl; $NR^{127}C(CR^{119}NO_2)S(C_1-C_4)$ alkyl; $NR^{127}C(NR^{127})NR^{127}R^{124}$; $NR^{127}C(=O)C(=O)NR^{127}R^{124}$; or $NR^{127}C(=O)C(=O)OR^{124}$;

$R^{116}$ is a member independently selected from the group consisting essentially of methyl and ethyl substituted by 0 to 5 bromo, chloro, or fluoro, wherein m may be 2 with respect to a single ring carbon atom to which $R^{116}$ is attached;

$R^{117}$ is a member independently selected from the group consisting essentially of $OR^{124}$; $SR^{124}SO_2NR^{127}R^{124}$; $NR^{127}R^{124}$; $NR^{124}C(=O)R^{119}$; $NR^{127}C(Y)R^{124}$; $NR^{127}C(=O)OR^{125}$; $S(O)_nR_{12}$ where n is an integer selected from 0, 1, and 2; $OS(=O)_2R^{122}$; $OR^{122}$; $OC(=O)NR^{123}R^{122}$; $OC(=O)R^{123}$; $OC(=O)OR^{123}$; $O(CR^{122}R^{123})_mOR^{122}$ where m is an integer selected from 0, 1, and 2; $CR^{119}R^{120}OR^{124}$; $CR^{119}R^{120}NR^{127}R^{124}$; $C(Y)R^{124}$; $C(=O)OR^{124}$; $C(Y)NR^{127}R^{124}$; CN; $C(NR^{127})NR^{127}R^{124}$; $C(NOR^{119})R^{124}$; $C(=O)NR^{119}NR^{119}C(=O)R^{119}$; $C(=O)NR^{119}NR^{127}R^{124}$; $C(NOR^{124})R^{119}$; $C(NR^{119})NR^{127}R^{124}$; $C(NR^{124})NR^{119}R^{120}$; $C(NCN)NR^{127}R^{124}$; $C(NCN)S(C_1-C_4)$ alkyl; tetrazolyl; thiazolyl; imidazolyl; imidazolidinyl; pyrazolyl; thiazolidinyl; oxazolyl; oxazolidinyl; triazolyl; isoxazolyl; oxadiazolyl; and thiadiazolyl; where the recited heterocyclic groups are substituted by 0 to 3 substituents where said substituent is $R^{124}$;

$R^{118}$ is a member independently selected from the group consisting essentially of —$NR\ 125$; —$NCR_{119}R^{120}$ $(C_2-C_6)$alkenyl; —$NOR^{124}$; —$NOR^{129}$; —$NOCR^{119}R^{120}(C_2-C_6)$ alkenyl; —$NNR^{119}R^{124}$; —$NNR^{119}R^{129}$; —NCN; —$NNR^{119}C(Y)NR^{119}R^{124}$; —$C(CN)_2$; —$CR^{124}CN$; —$CR^{124}C(=O)R^{119}$; —$CR^{124}C(=O)NR^{119}R^{124}$; —$C(CN)NO_2$; —$C(CN)C(=O)O(C_1-C_4)$ alkyl; —$C(CN)OC(=O)O(C_1-C_4)$ alkyl; —$C(CN)(C_1-C_4)$alkyl; —$C(CN)C(=O)NR^{119}R^{124}$; 2-(1,3-dithiane), 2-(1,3-dithiolane), dimethylthio ketal, diethylthio ketal, 2-(1,3-dioxolane), 2-(1,3-dioxane), 2-(1,3-oxathiolane); dimethyl ketal and diethyl ketal;

$R^{119}$ and $R^{120}$ are each a member independently selected from the group consisting essentially of hydrogen and $(C_1-C_4)$ alkyl substituted by 0 to 3 fluorine atoms;

$R^{121}$ is a member independently selected from the group consisting essentially of fluoro and $R^{120}$;

$R^{122}$ is a member independently selected from the group consisting essentially of $(C_1-C_6)$ alkyl; $(C_2-C_3)$ alkenyl; $(C3-C_7)$ cycloalkyl; $(C_3-C_7)$ cycloalkyl$(C_1-C_2)$ alkyl; $(C_6-C_{10})$ aryl; and $(C_3-C_9)$heterocyclyl; where said aryl and heterocyclyl are as defined under $R^A{}_5$ above; and where said $R^{122}$ groups are substituted with 0 to 3 substituents independently selected from the group consisting essentially of methyl; ethyl; mono-, di-, and tri-fluoromethyl; and bromo, chloro, or fluoro;

$R^{123}$ is a member independently selected from the group consisting essentially of hydrogen and $R^{122}$;

$R^{124}$ is a member independently selected from the group consisting essentially of hydrogen and $R^{125}$; or when $R^{124}$ and $R^{127}$ appear together as $NR^{127}R^{124}$ then $R^{127}$ and $R^{124}$ may be taken together with the nitrogen to which they are attached to form a 5- to 7-membered ring optionally containing one additional heteroatom selected from O, N and S;

$R^{125}$ is a member independently selected from the group consisting essentially of $(C_1-C_6)$ alkyl and —$(CR^{119}R^{120})_nR^{126}$, where n is an integer selected from 0, 1, and 2 and $R^{126}$ and said $(C_1-C_6)$ alkyl are substituted by 0 to 3 substituents where each said substituent is a member independently selected from the group consisting essentially of bromo, chloro, or fluoro; nitro; cyano; $NR^{120}R^{127}$; $C(=O)R^{119}$; $OR^{119}$;

C(=O)NR¹²⁰R¹²⁷; OC(=O)NR¹²⁰R¹²⁷; NR¹²⁷C
(=O)NR¹²⁷R¹²⁰; NR¹²⁷C(=O)R¹²⁰; NR₁₇C(=O)O
(C₁–C₄) alkyl; C(NR¹²⁷)NR¹²⁷R¹²⁰; C(NCN)
NR¹²⁷R¹²⁰; C(NCN)S(C₁–C₄) alkyl; NR¹²⁷C(NCN)S
(C₁–C₄) alkyl; NR¹²⁷C(NCN)NR¹²⁷R¹²⁰; NR¹²⁷S
(=O)₂(C₁–C₄)alkyl; S(O)ₙ(C₁–C₄) alkyl; where n is an
integer selected from 0, 1, and 2; NR¹²⁷C(=O)C(=O)
NR¹²⁷R¹²⁰, NR¹²⁷C(=O)C(=O)R¹²⁷; thiazolyl; imidazolyl; oxazolyl; pyrazolyl; triazolyl; tetrazolyl; and
(C₁–C₂) alkyl substituted with 0 to 3 fluorine atoms;

R¹²⁶ is a member independently selected from the group consisting essentially of (C₃–C₇) cycloalkyl; pyridyl; pyrimidyl; pyrazolyl; imidazolyl; triazolyl; pyrrolyl; piperazinyl; piperidinyl; morpholinyl; furanyl; thienyl; thiazolyl; quinolinyl; naphthyl; and phenyl;

R¹²⁷ is a member independently selected from the group consisting essentially of OR¹¹⁹ and R¹²¹;

R¹²⁸ is a member independently selected from the group consisting essentially of H; C(Y)R¹²⁴; C(=O)OR²; C(Y)NR¹²⁷R¹²⁴; CN; C(NR¹²⁷)NR¹²⁷R¹²⁴; C(NOR¹¹⁹)R¹²⁴; C(=O)NR¹¹⁹NR¹¹⁹C(=O)R¹¹⁹; C(=O)NR¹¹⁹NR¹²⁷R¹²⁴; C(NOR¹²⁴)R¹¹⁹; C(NR¹¹⁹)NR¹²⁷R¹²⁴; C(NR¹²⁴)NR¹¹⁹R¹²⁰; C(NCN)NR¹²⁷R¹²⁴; C(NCN)S(C₁–C₄) alkyl; CR¹¹⁹R¹²⁰OR¹²⁴; CR¹¹⁹R¹²⁰SR¹²⁴; CR¹¹⁹R¹²⁰S(O)ₙR¹²⁵, where n is an integer selected from 0, 1, and 2; CR¹¹⁹R¹²⁰NR¹²⁴R¹²⁷; CR¹¹⁹R¹²⁰NR¹²⁷S(=O)₂R¹²⁵; CR¹¹⁹R¹²⁰NR¹²⁷C(Y)R¹²⁴; CR¹¹⁹R¹²⁰NR¹²⁷C(=O)OR¹²⁵; CR¹¹⁹R¹²⁰NR¹²⁷C(Y)NR¹²⁷R¹²⁴; CR¹¹⁹R¹²⁰NR¹²⁷C(NCN)NR¹²⁷R¹²⁴; CR¹¹⁹R¹²⁰NR¹²⁷C(CR₉NO₂)S(C₁–C₄) alkyl; tetrazolyl; thiazolyl; imidazolyl; imidazolidinyl; pyrazolyl; thiazolidinyl; oxazolyl; oxazolidinyl; triazolyl; isoxazolyl; oxadiazolyl; thiadiazolyl; wherein said recited heterocyclic groups are substituted by 0 to 3 substituents where each said substituent is independently selected from the group consisting essentially of R¹²⁴;

R¹²⁹ is a member independently selected from the group consisting essentially of —C(=O)R¹²; —C(=O)NR¹¹⁹R¹²⁴; —S(=O)₂R¹²⁵; and —S(=O)₂NR¹¹⁹R¹²⁴;

Y is O or S; and,

Z is O; NR¹²⁷; NCN; C(—CN)₂; CR¹¹⁹CN; CR¹¹⁹NO₂; CR¹¹⁹C(=O)OR¹¹⁹; CR¹¹⁹C(=O)NR¹¹⁹R¹²⁰; C(—CN)C(=O)O(C₁–C₄) alkyl); and C(—CN)C(=O)NR¹¹⁹R¹²⁰;

—OR, said substituents defining R²ₐ and R²ᵦ comprise:

II a member selected from the group consisting essentially of R²²⁹; —C(=O)NR²²²(CHR²²²)ₘC(=O)NR²²²(CH₂)ᵩ(C₆–C₁₀) aryl); —C(=NR²⁴²)NH(CH₂)ₚ(C₆–C₁₀) aryl; —C(=O)NR²¹⁸(CHR²²²)ₘC(=O)NR²²²(CH₂)ₚOR²²²; —C(=O)NR²²²(CHR²²²)ₘS(C₁–C₄) alkyl; —C[=NOC(=O)R²³⁵]R²³⁶; —CR²²⁷R²²⁸CHR²³⁸NR²¹⁹SO₂(CH₂)ₚA; —CR²²⁷R²²⁸CHR²³⁸NR²¹⁹P(=O)(OR²²²)C(=O)(C₁–C₄) alkyl; —CR²²⁷R²³⁸CHR²³⁸NR²¹⁹P(=O)[(C₁–C₄) alkoxy]₂, -Z³-R²¹⁷; and —(CR²²⁷R²²⁸)ₘNR²¹⁹(C(O))ᵩR²²⁰ wherein p is an integer selected from 0, 1, and 2; m is an integer selected from 1, 2, 3, 4, 5, and 6; and q is an integer selected from 1 and 2;

—OR, said substituents defining R²ₐ and R²ᵦ comprise a moiety of partial Formulas (IIA) through (III), inclusive:

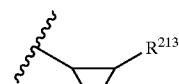

(IIA)

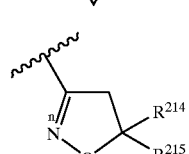

(IIB)

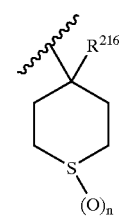

(IIC)

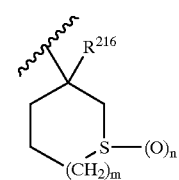

(IID)

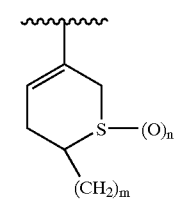

(IIE)

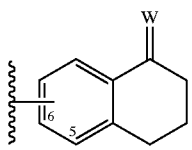

(IIF)

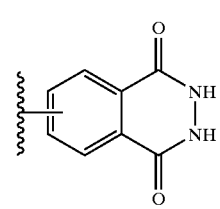

(IIG)

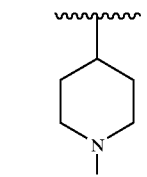

(IIH)

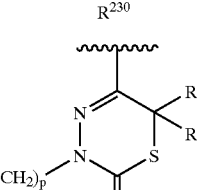

(III)

wherein in said partial Formulas (IIA)–(III), the structures of partial Formulas (IIF) and (IIG) are attached to the nucleus of Formula (IA) or (IB) at carbons 5, 6, or 7 of said partial Formulas (IIF) and (IIG); the dashed line in partial Formulas (IIC) and (IID) indicates a single bond or double bond, except that $R^{316}$ is absent in formulas (IIC) and (IIID) where said dashed line indicates a double bond; n is an integer selected from 0, 1, and 2; p is an integer selected from 0, 1, 2, 3, 4, 5, and 6; and m is an integer selected from 0, and 1;

$R^{213}$ is a member independently selected from the group consisting essentially of —C(=O)N(CH$_3$)(OCH$_3$) and —(CH$_2$)$_n$OH, where n is an integer selected from 0, 1, 2, 3, and 4;

$R^{214}$ and $R^{215}$ are independently selected from the group consisting essentially of H; ethyl; —CO$_2$H; and —C(=O)NHOH;

$R^{216}$ is a member independently selected from the group consisting essentially of H; hydroxy; (C$_1$–C$_6$) alkyl; (C$_1$–C$_6$) alkoxy; —OC(=O)(C$_1$–C$_6$) alkyl and —OC(=O)(C$_6$–C$_{10}$) aryl;

$R^{217}$ is a member independently selected from the group consisting essentially of (C$_6$–C$_{10}$)aryl and a 5- to 10-membered heterocyclyl, wherein said $R^{217}$ groups are substituted by 0 to 3 substituents independently selected from the group consisting essentially of bromo, chloro, or fluroro; trifluoromethyl; cyano; nitro; —CO$_2$R$^{222}$, (C$_1$–C$_4$) alkoxy; —OC(=O)(C$_1$–C$_4$) alkyl; —NR$^{222}$C(=O)(C$_1$–C$_4$)alkyl; —C(=O)NH$_2$; —C(=O)NHOH; —C(=O)O(C$_1$–C$_4$) alkyl; (C$_1$–C$_4$) alkyl; —S(O)$_n$R$^{222}$ where n is an integer selected from 0, 1, and 2; benzoyl; —NR$^{222}$R$^{223}$, —OR$^{222}$, (C$_1$–C$_6$) alkanoyl; —Y$^1$—(C$_6$–C$_{10}$) aryl; —C(=O)O(C$_6$–C$_{10}$) aryl; —NH(C$_6$–C$_{10}$) aryl; —C(=O)NH(C$_6$–C$_{10}$) aryl; —C(=O)NR$^{222}$O(CH$_2$)$_n$(C$_6$–C$_{10}$) aryl, where n is an integer select from 1, 2, and 3; and —SO$_2$NH(C$_6$–C$_{10}$) aryl;

$R^{218}$ is a member independently selected from the group consisting essentially of H; (C$_1$–C$_6$) alkyl; and —(CH$_2$)$_n$(C$_6$–C$_{10}$) aryl, where n is an integer selected from 0, 1, 2, 3, and 4;

$R^{219}$ is a member independently selected from the group consisting essentially of H; —OR$^{220}$; —(CH$_2$)$_m$A; and —CH$_2$O(CH$_2$)$_m$A, where m is an integer selected from 0, 1, and 2

$R^{220}$ is a member independently selected from the group consisting essentially of (C$_1$–C$_4$) alkyl; —OR$^{222}$, —CR$^{222}$R$^{223}$OR$^{222}$; —CR$^{222}$R$^{223}$NR$^{222}$R$^{223}$; —CR$^{222}$(OR$^{223}$)CR$^{222}$R$^{223}$OR$^{222}$; 2,2-dimethyl-1,3-dioxolan-4-yl; —NR$^{222}$C(=O)NR$^{222}$R$^{223}$, —S(CR$^{222}$R$^{223}$)$_n$CH$_3$ where n is an integer selected from 0, 1, 2, 3, 4, and 5; —NR$^{222}$(CH$_2$)$_q$(pyridyl) where q is an integer selected from 0 and 1; —P(=O)[(C$_1$–C$_4$) alkoxy)]$_2$; —NR$^{222}$R$^{223}$; —NR$^{222}$OR$^{223}$; —NR$^{222}$NR$^{223}$R$^{221}$, —NR$^{222}$CH$_2$R$^{224}$; —OCH$_2$NR$^{222}$C(=O)R$^{224}$; —OCH$_2$C(=O)NR$^{225}$R$^{226}$, —OCHR$^{222}$OC(=O)(C$_1$–C$_4$) alkyl; —OCHR$^{222}$C(=O)(C$_1$–C$_3$) alkoxy; —O(CH$_2$)$_m$R$^{221}$; and —NR$^{222}$(CH$_2$)$_m$R$^{221}$ where m is an integer selected from 0, 1, and 2;

$R^{221}$ is a member independently selected from the group consisting essentially of H and A;

each $R^{222}$ and $R^{223}$ is a member independently selected from the group consisting essentially of H and (C$_1$–C$_4$) alkyl;

$R^{224}$ is a member independently selected from the group consisting essentially of methyl and phenyl;

$R^{225}$ is a member independently selected from the group consisting essentially of H; methyl; ethyl; and —CH$_2$CH$_2$OH;

$R^{226}$ is a member independently selected from the group consisting essentially of H; methyl; ethyl; —CH$_2$C(=O)NH$_2$; and —CH$_2$CH$_2$OH;

each $R^{227}$ is a member independently selected from the group consisting essentially of H; hydroxy; cyano; halo; (C$_1$–C$_3$) alkyl; (C$_1$–C$_3$) alkoxy; —NR$^{222}$R$^{223}$; —C(=O)OR$^{222}$; —C(=O)OR$^{222}$; —C(=O)R$^{222}$; —CH=CR$^{222}$R$^{223}$; —C≡CR$^{222}$; —CH$_2$NR$^{222}$R$^{223}$; —CH$_2$OR$^{222}$; —C(=O)NR$^{222}$R$^{223}$; —C(Y$^5$)H; and —CH$_2$NR$^{12}$C(=O)C(=O)NR$^{222}$R$^{223}$; provided that when $R^{227}$ is hydroxy then $R^{228}$ is H or (C$_1$–C$_4$) alkyl;

each $R^{228}$ is a member independently selected from the group consisting essentially of H; fluoro; cyano; and (C$_1$–C$_4$) alkyl; where said methyl is substituted by 0 to 3 substituents each comprising a fluorine atom;

or $R^{227}$ and $R^{228}$ are taken together to form an oxo (=O) moiety;

$R^{229}$ is a member independently selected from the group consisting essentially of phenyl; naphthyl; pyrrolyl; furanyl; thienyl; oxazolyl; pyridinyl; pyrimidinyl; pyridazinyl; quinolinyl; isoquinolinyl; 5,6,7,8-tetrahydroquinolinyl; and 5,6,7,8tetrahydroisoquinolinyl, where said $R^{229}$ groups, except said phenyl, are substituted by 0 to 3 substituents $R^{233}$, and wherein said phenyl $R^{229}$ group is substituted by 0 to 3 substituents independently selected from $R^{233}$ and $R^{234}$;

$R^{230}$ is a member independently selected from the group consisting essentially of —C(=O)R$^{231}$; —C(=O)C(=O)R$^{231}$, —C(=O)C(Y$^2$)C(=O)R$^{231}$and a moiety of partial Formula (IIJ):

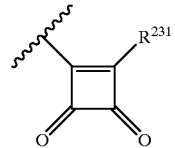

(IIJ)

wherein
$R^{231}$ is a member independently selected from the group consisting essentially of H; —OR$^{232}$; —NHR$^{232}$, —NHOH; —NHNH$_2$; —(CH$_2$)$_n$Y$^3$(phenyl) and —(CH$_2$)$_n$Y$^3$(pyridyl) where n is an integer selected from 0, 1, 2, 3, and 4;

$R^{232}$ is a member independently selected from the group consisting essentially of H; (C$_1$–C$_8$) alkyl; —(CH$_2$)$_n$Y$^3$(phenyl) and —(CH$_2$)$_n$Y$^3$(pyridyl) where n is an integer selected from 0, 1, 2, 3, and 4;

each $R^{233}$ is a member independently selected from the group consisting essentially of bromo, chloro, or fluoro; (C$_1$–C$_6$) alkyl; (C$_1$–C$_7$)alkoxy; (C$_2$–C$_6$) alkylenedioxy; trifluoromethyl; —NR$^{222}$R$^{223}$; nitro; —C(NR$^{222}$)NR$^{222}$R$^{223}$; —C(=O)NR$^{222}$R$^{223}$C(=O)R$^{222}$; —C(NOR$^{222}$)R$^{223}$; —C(NCN)NR$^{222}$R$^{223}$; —C(NCN)SR$^{222}$; —(CH$_2$)$_m$(CN) where m is an integer selected from 0, 1, 2, and 3; hydroxy; —C(=O)R$^{222}$, —C(=O)NR$^{222}$OR$^{223}$; —C(=O)NR$^{222}$NR$^{222}$R$^{223}$; —OC(=O)NR$^{222}$R$^{223}$; —NR$^{222}$C(=O)R$^{222}$; —C(=O)C(=O)NR$^{222}$R$^{223}$; —CO$_2$R$^{222}$; —SO$_2$R$^{222}$; —SO$_2$NR$^{222}$R$^{222}$; —C(=O)NR$^{222}$R$^{223}$; —NR$^{222}$SO$_2$R$^{223}$; and —NR$^{222}$C(=O)NR$^{222}$R$^{223}$;

each $R^{234}$ is a member independently selected from the group consisting essentially of imidazolyl; pyrazolyl; triazolyl; tetrazolyl; oxazolyl; isoxazolyl; oxadiazolyl; thiadiazolyl; thiazolyl; oxazolidinyl; thiazolidinyl; and imidazolidinyl, where each of said foregoing $R^{234}$ substituents is substituted by 0 to 3 substituents $R^{233}$;

R²³⁵ is a member independently selected from the group consisting essentially of —NR²²²R²²³; —NH(C₆–C₁₀) aryl; (C₁–C₆) alkoxy; and (C₆–C₁₀) aryloxy;

R²³⁶ is a member independently selected from the group consisting essentially of H; (C₁–C₆) alkyl and —(CH₂)ₘY⁴(phenyl) where m is an integer selected from 0, 1, 2, 3, and 4 and the phenyl moiety of said —(CH₂)ₘY⁴(phenyl)R²³⁶ group is substituted by 0 to 3 substituents independently selected from the group consisting essentially of bromo, chloro, or fluoro; —OR²²²; (C₁–C₆) alkanoyloxy; (C₆–C₁₀)aryloxy; —NR²²²R²²³; —NH(C₆–C₁₀)aryl; and —NHC(=O)(C₁–C₄) alkyl;

each R²³⁷ is a member independently selected from the group consisting essentially of bromo, chloro, or fluoro; —(CH₂)ₚNR²²²C(=O)CH₃ where p is an integer selected from 1, 2, 3, 4, and; (C₁–C₄) alkoxy; nitro; cyano; —NR²²²R²²³; —COR²²²; —OR²²², —C(Y¹)NR²²²R²²³; —NR²²²C(NCN)S(C₁–C₃) alkyl; —NR²²²C(NCN)NR²²²R²²³; —NR²²²C(=O)NR²²²R²²³; —NR²²²C(=O)C(=O)NR²²²R²²³; —C(=NR²²²)NR²²²R²²³; —S(O)ₘCH₃ where m is an integer selected from 0, 1, and 2, —C(=NR²²²)S(C₁–C₃) alkyl; —NR²²²SO₂(C₁–C₃) alkyl; —OC(=O)R²²², —OC(=O)NR²²²R²²³; —NR²²²SO₂CF₃; —NR²²²C(=O)C(=O)OR²²², —NR²²²C(=O)R²²²; —NR²²²C(=O)OR²²²; imidazolyl; thiazolyl; oxazolyl; pyrazolyl; triazolyl; and tetrazolyl;

R²³⁸ is a member independently selected from the group consisting essentially of H; fluoro; cyano; and (C₁–C₂) alkyl, where said alkyl is substituted by 0 to 3 substituents independently selected from the group consisting essentially of bromo, chloro, or fluoro; —C(=O)NR²²²R²²³; and —C(=O)OR²²²;

R²³⁹ is a member independently selected from the group consisting essentially of phenyl substituted by 0 to 2 substituents independently selected from —NR²²²R²²³, nitro, halo, —OR²²², —NHR²⁴⁰, —N²⁴⁰R²⁴¹, and —C(=O)OR²²²;

each R²⁴⁰ and R²⁴¹ is a member independently selected from the group consisting essentially of (C₁–C₈) alkyl and (C₂–C₈) alkenyl;

R²⁴² is pyridin-4-yl substituted by 0 to 2 substituents independently selected from the group consisting essentially of bromo, chloro, or fluoro; and (C₁–C₄) alkyl;

each A is a member independently selected from the group consisting essentially of (C₁–C₆) alkyl; pyridyl; morpholinyl; piperidinyl; imidazolyl; thienyl; pyrimidyl; thiazolyl; triazolyl; quinolinyl; phenyl; and naphthyl; wherein the foregoing A groups are substituted with 0 to 3 substituents R²³⁷; or A is —(CH₂)qS(C₁–C₄) alkyl wherein q is an integer selected from 1 and 2;

W is a member independently selected from the group consisting essentially of O; NOH; NNH₂; NOC(=O)CH₃; and NNHC(=O)CH₃;

Y is O or S;

Y² is O, NOH or H₂;

Y³ is a bond or —CH=CH—;

Y⁴ is a bond, O, S, or —NH—;

Y⁵ is a member independently selected from the group consisting essentially of O; NR²²²; NOR²²²; NCN; C(CN)₂; CR²²²NO₂; CR²²²C(=O)OR²²²; CR²²²C(=O)NR²²²R²²³; C(CN)NO₂; C(CN)C(=O)OR²²²; and C(CN)C(=O)NR²²²R²²³; and Z³ is a member independently selected from the group consisting essentially of —NR²²²; —(CH₂)ₘ—; —CH₂C(=O)NH—; —NHCH₂C(=O)—; —CH₂C(Y¹)CH₂—; —CH=CH—, —C≡C—, —CH(Y¹H)—; —C(Y¹)—; —CH₂C(Y¹); —C(Y¹)CH₂—; —C(Y₁)C(Y₁)-; —CH₂NR²²²—; —CH₂-Y¹; —C(Y¹)NR²¹⁸(CHR²²²)ₙ—; —NR²¹⁸C(Y¹)(CHR²²²)ₙ—; —NHCH₂—; -Y¹-CH₂—; —SOCH₂—; —CH₂SO—; —SO₂CH₂—; —CH₂SO₂—; —OC(Y¹)-; —N=N—; —NHSO₂—; —SO₂NH—; —C(Y¹)C(Y¹)NH—; —NHC(=O)O—; —OC(=O)NH—; and —NHC(=O)NH—; wherein for said Z₃ moieties n is an integer selected from 0, 1, 2, 3, and 4; and m is an integer selected from 1, 2, and 3;

—OR said substituents defining R²ₐ and R²b comprise:

III a member independently selected from the group consisting essentially of 2-oxo-4-pyrrolyl; pyrazolyl; 2-oxo-3,4-dihydro-5-pyrimidyl; 2-oxo-3,4-dihydro-4-pyrimidyl; 2-oxo-tetrahydro-4-pyrimidyl; 2-oxo-tetrahyro-5-pyrimidyl; 2-oxo-4-pyrimidyl; and 2-oxo-5-pyrimidyl; wherein each of said R²ₐ and R²ᵦ groups is substituted by 0, 1, 2, 3, or 4 R²³⁶ groups;

—OR, said substituents defining R²ₐ and R²ᵦ comprise a moiety of partial Formulas (IIA) through (III), inclusive:

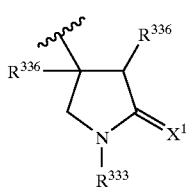

(IIIA)

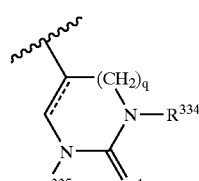

(IIIB)

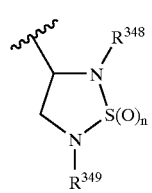

(IIIC)

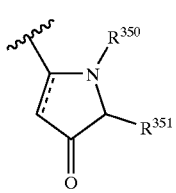

(IIID)

-continued
| (IIIE) | (IIIF) |
|---|---|
| 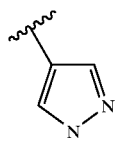 | 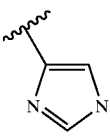 |
| (IIIG) | (IIIH) |
| 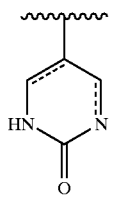 | 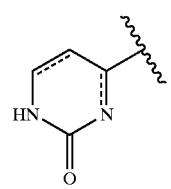 |
| (IIII) | (IIIJ) |
| 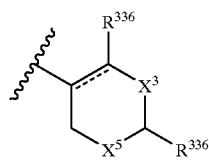 | 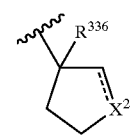 |
| (IIIK) | (IIIL) |
| 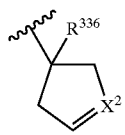 | 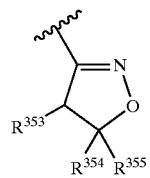 |
| (IIIM) | (IIIN) |
| 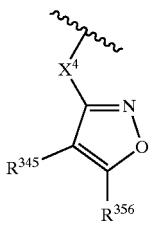 | 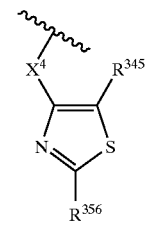 |
| (IIIO) | (IIIP) |
| 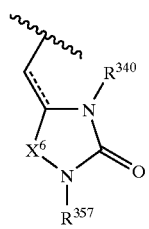 | 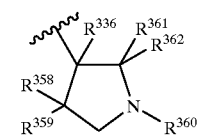 |
| (IIIQ) | (IIIR) |
| 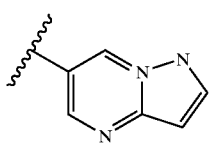 | 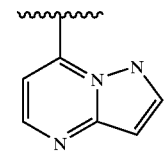 |
| (IIIS) | (IIIT) |
| 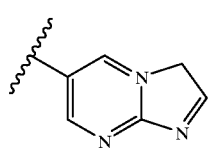 | 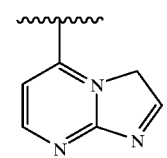 | wherein, in said partial Formulas (IIIA)–(IIIT), q is an integer selected from 0 and 1 in partial Formula (IIIB); n is an integer selected from 0, 1, and 2 in partial Formula (IIIC); and the dashed lines appearing in formulas (IIIB), (IIID), (IIIG), (IIIH), (IIII), (IIIJ) and (IIIO) represent a double bond or a single bond;

$X^1$ is O or S;

$X^2$, in formula (IIIK) and where the dashed line in formula (IIIJ) represents a double bond, is a member independently selected from the group consisting essentially of $CR^{335}$; $CR^{336}$; $CR^{346}$; and $COC(=O)NR^{339}R^{342}$; or, where the dashed line in formula (IIIJ) represents a single bond, $X^2$ is a member independently selected from the group consisting essentially of $CR^{335}R^{339}$; $CR^{336}R^{339}$; and $CR^{346}R^{339}$;

$X^3$ is a member independently selected from the group consisting essentially of $C(=Z^3)$; $C(S)$; and $CR^{336}R^{340}$;

$X^4$ is a member independently selected from the group consisting essentially of —$(CH_2)_m$- where m is an integer selected from 0, 1, and 2;

$X^5$ is a bond or —$CH_2$—;

$X^6$ is a member independently selected from the group consisting essentially of —$CH_2$— and —$C(=O)$—;

$R^{333}$ is a member independently selected from the group consisting of H; hydroxy; $(C_1-C_4)$alkoxy; —$CHR^{337}(O)_q(CH_2)_m A$ where q is an integer selected from 0 and 1, is an integer selected from 0, 1, and 2;

$R^{334}$ is a member independently selected from the group consisting of H; hydroxy; $(C_1-C_4)$ alkyl; $(C_1-C_2)$ alkoxy; —$OC(=O)CH_3$; $(C_2-C_3)$ alkenyl; and phenyl$(C_1-C_2)$ alkyl-;

$R^{335}$ is a member independently selected from the group consisting of H; hydroxy; —$(CH_2)_m A$ where m is an integer selected from 0, 1, and 2; $(C_1-C_6)$ alkyl; and $(C_2-C_3)$ alkanoyl; where said alkyl group is substituted by 0 to 3 subtituents independently selected from the group consisting essentially of bromo, chloro, or fluoro; nitro; —$NR^{340}R^{341}$; —$CO_2R^{340}$; —$OR^{340}$; —$OC(=O)R^{340}$; —$C(=O)R^{340}$; cyano; —$C(=Y)NR^{340}R^{341}$; —$NR^{340}C(=Y)NR^{340}R^{341}$; —$NR^{340}C(=Y)R^{340}$; —$NR^{340}C(=O)OR^{340}$); —$C(NR^{340})NR^{340}R^{341}$; —$C(NCN)NR^{340}R^{341}$; —$C(NCN)SR^{340}$; —$NR^{340}SO_2R^{340}$; —$S(O)_m R^{340}$, where m is an integer selected from 0, 1, and 2; —$NR^{340}SO_2CF_3$; —$NR^{340}C(=O)C(=O)NR^{340}R^{341}$; —$NR^{340}C(=O)C(=O)OR^{340}$; imidazolyl; and 1-$(NHR^{340})$-2-imidazolyl;

each $R^{336}$ is a member independently selected from the group consisting essentially of H; bromo, chloro, or fluoro; cyano; $R^{33}$; cyclopropyl substituted by 0 or 1 substituent independently selected from the group consisting essentially of $R^{339}$; —$OR^{340}$; —$CH_2OR^{340}$; —$NR^{340}R^{342}$; —$CH_2NR^{340}R^{342}$; —$C(=O)OR^{340}$; —$C(=O)NR^{340}R^{342}$; —$CH=CR^{339}R^{339}$; —$C≡CR^{339}$; and —$C(=Z^3)H$;

$R^{337}$ is a member independently selected from the group consisting essentially of H; —$C(=O)R^{338}$; imidazolyl; pyrazolyl; triazolyl; tetrazolyl; oxazolyl; isoxazolyl; oxadiazolyl; thiadiazolyl; thiazolyl; oxazolidinyl; thiazolidinyl; and imidazolidinyl;

each $R^{338}$ is a member independently selected from the group consisting essentially of —$OR^{340}$; —$NR\ R^{342}$; and —$R^{343}$;

each $R^{339}$ is a member independently selected from the group consisting essentially of H; bromo, chloro, or fluoro; and $(C_1-C_4)$ alkyl substituted by 0 to 3 fluorine atoms;

each $R^{340}$ and $R^{341}$ is a member independently selected from the group consisting essentially of hydrogen and $(C_1-C_4)$ alkyl;

each $R^{342}$ is a member independently selected from the group consisting essentially of —$OR^{340}$ and —$R^{340}$;

$R^{343}$ is $(C_1-C_4)$ alkyl;

each $R^{343}$ is a member independently selected from the group consisting essentially of bromo, chloro, or fluoro; nitro; cyano; —$NR^{340}R^{346}$; —$NR^{346}R^{342}$; —$C(=Z^3)R^{338}$; —$S(O)_m R^{343}$ where m is an integer selected from 0, 1, and 2; —$OR^{342}$; —$OC(=O)NR^{340}R^{342}$; —$C(NR^{342})NR^{340}R^{342}$; —$C(NR^{340})SR^{343}$; —$OC(=O)CH_3$; —$C(NCN)NR^{340}R^{342}$; —$C(S)NR^{340}R^{342}$; —$NR^{342}C(=O)R^{347}$; —$C(=O)R^{347}$; oxazolyl; imidazolyl; thiazolyl; pyrazolyl; triazolyl; and tetrazolyl;

each $R^{345}$ is a member independently selected from the group consisting essentially of hydrogen and $(C_1-C_4)$ alkyl substituted by 01 to 3 fluorine atoms;

each $R^{346}$ is a member independently selected from the group consisting essentially of H; —$R^{343}$; —$C(=O)R^{343}$; —$C(=O)C(=O)R^{338}$; —$C(=O)NR^{340}R^{342}$; —$S(O)_m R^{343}$ where m is an integer selected from 0, 1, and 2; —$C(NCN)SR^{343}$; —$C(NCN)R^{343}$; —$C(NR^{342})R^{343}$; —$C(NR^{342})SR^{343}$; and —$C(NCN)NR^{340}R^{342}$;

each $R^{347}$ is a member independently selected from the group consisting essentially of —$R^{343}$; —$C(=O)R^{343}$; oxazolidinyl; oxazolyl; thiazolyl; pyrazolyl; triazolyl; tetrazolyl; imidazolyl; imidazolidinyl; thiazolidinyl; isoxazolyl; oxadiazolyl; thiadiazolyl; morpholinyl; piperidinyl; piperazinyl; and pyrrolyl; where each of said recited $R^{347}$ heterocyclic groups is substituted by 0 to 2 $(C_1-C_2)$ alkyl groups;

$R^{348}$ is a member independently selected from the group consisting essentially of H; $(C_1-C_5)$ alkyl; $(C_2-C_5)$ alkenyl; benzyl; and phenethyl;

$R^{349}$ is a member independently selected from the group consisting essentially of H; $(C_1-C_5)$ alkyl; $(C_1-C_5)$ alkanoyl; and benzoyl;

$R^{350}$ is a member independently selected from the group consisting essentially of H; $(C_1-C_4)$ alkyl; carboxy; aminocarbonyl; $(C_1-C_6)$ alkyl substituted by 0 or 1 carboxy, —$(CH_2)_m C(=O)(C_1-C_6)$ alkoxy; or —$(CH_2)_m (C_6-C_{10})$ aryl; where m is an integer selected from by 0 or 1, and 2;

$R^{351}$ is a member independently selected from the group consisting essentially of H; $(C_1-C_6)$ alkyl; —$C(=Y)R^{352}$; —$C(=Y)NH^{352}$; —$C(=O)OR^{352}$; and —$(CH_2)_n X^7$(pyridyl) where n is an integer selected from 0, 1, 2, 3, 4, and to 5; and $X^7$ is a bond or —CH=CH—; and where said pyridyl moiety is substituted by 0 or 1 bromo, chloro, or fluoro;

$R^{352}$ is a member independently selected from the group consisting essentially of $(C_1-C_6)$ alkyl $(C_3-C_8)$ cycloalkyl; —$(CH_2)_m (C_6-C_{10})$ aryl; and —$(CH_2)_n X^7$ (pyridyl) where n is an integer selected from 0, 1, 2, 3, 4, and 5; and $X^7$ is a bond or —CH=CH—; and where said pyridyl moiety is substituted by 0 or 1 bromo, chloro, or fluoro;

$R^{353}$ is a member independently selected from the group consisting essentially of H; —$R^{345}$; $(C_1-C_3)$ alkyl substituted by 0 or 1 substituent hydroxy, or $(C_1-C_3)$ alkyoxy$(C_1-C_3)$ alkyl;

$R^{354}$ is a member independently selected from the group consisting essentially of H; —$R^{345}$; carboxy; $(C_1-C_3)$ alkyoxy($C_1$–$C_3$) alkyl-; (C3–$C_7$) cycloalkyl; and ($C_1$–$C_5$) alkyl substituted by 0 or 1 —$NR^{340}R^{341}$;
or $R^{353}$ and $R^{354}$ are taken together to form —$CH_2OCH_2OCH_2$—;

$R^{355}$ is a member independently selected from the group consisting essentially of H; hydroxy; ($C_1$–$C_4$) alkyl substituted by 0 or 1 substituent comprising a member independently selected from the group consisting essentially of hydroxy; —C(=O)$R^{340}$; —$NR^{340}R^{341}$; —$(CH_2)_m$NHC(=O)$R^{340}$; —$(CH_2)_m$NHC(=O)R; —$(CH_2)_m$CO$_2R^{340}$; —$(CH_2)_m$NHC(=O)$R^{341}$; —$(CH_2)_m$C(=O)N(OH)$R^{340}$; —$(CH_2)_m$SO$_2NR^{340}R^{341}$; —$(CH_2)_m$PO$_3H_2$; —$(CH_2)_m$SO$_2$NHC(=O)$R^{343}$; and —$(CH_2)_m$SO$_2$NHC(=O)(phenyl), where m is an integer selected from 0, 1, 2, 3, and 4;

$R^{353}$ is a member independently selected from the group consisting essentially of H; ($C_1$–$C_4$) alkyl; phenyl; —$NR^{340}R^{341}$; and —$NR^{340}$($C_1$–$C_4$) alkanoyl;

$R^{357}$ is a member independently selected from the group consisting essentially of —$R^{340}$; —$CH_2CO_2R^{343}$; and —$CH_2C$(=O)$NR^{340}R^{341}$;

$R^{358}$ is a member independently selected from the group consisting essentially of —C(=O)$R^{340}$; —C(=O)($C_6$–$C_{10}$) aryl; —C(=O)($C_3$–$C_9$) heteroaryl; —CO$_2R^{340}$; —C(=O)$NR^{340}R^{341}$; cyano; nitro; —$CH_2$OH; —$NR^{340}$SO$_2R^{340}$; —NHSO$_2$($C_6$–$C_{10}$) aryl; —NHCO$_2$($C_1$–$C_4$) alkyl; —$NR^{340}$C(=O)$R^{340}$; and —NHCO$_2$($C_6$–$C_{10}$) aryl;

$R^{359}$ is a member independently selected from the group consisting essentially of —$R^{345}$; cyano; carboxy; formyl; —C(=O)$R^{340}$; and ($C_1$–$C_4$) alkanoyl;

$R^{360}$ is a member independently selected from the group consisting essentially of cyano; —$NR^{340}R^{341}$; —SO$_2$($C_1$–$C_4$) alkyl; —SO$_2$($C_6$–$C_{10}$) aryl; —C(=O)$R^{340}$; —C(=O)($C_6$–$C_{10}$) aryl; —C(=O)($C_3$–$C_9$) heteroaryl; —C(=O)$NR^{340}R^{341}$; and —CO$_2R^{340}$;

$R^{361}$ and $R^{362}$ is each a member independently selected from the group consisting essentially of H; cyano; nitro; —CO$_2R^{340}$; —C(=O)$NR^{340}R^{341}$; —$CH_2$OH; —C(=O)$R^{340}$; —NHCO$_2R^{340}$; and —NHSO$_2R^3$;

A is a member independently selected from the group consisting essentially of pyridyl; morpholinyl; piperidinyl; imidazolyl; thienyl; pyrimidyl; thiazolyl; phenyl; and naphthyl; where each of said A groups is substituted by 0 to 2 substituents $R^{344}$ or by 1 substituent $R^{345}$;

$Z^3$ is a member independently selected from the group consisting essentially of O; —$NR^{342}$; $NOR^{340}$; N(CN); C(CN)$_2$; $CR^{340}NO_2$; $CR^{340}$C(=O)$OR^{343}$; $CR^{340}$C(=O)$NR^{340}R^{341}$; C(CN)$NO_2$; C(CN)C(=O)$OR^{343}$; and C(CN)C(=O)$NR^{340}R^{341}$; and, Y is O or S;

—OR said substituents defining $R^2_a$ and $R^2_b$ comprise a moiety of partial Formula (IV):

IV

(IV)

wherein
the broken line indicates a single or double bond;
$X^1$ is —$CR^{472}R^{473}$— where said broken line indicates a single bond; or —$CR^{473}$— where said broken line indicates a double bond;

$X^2$ is —$OR^{475}R^{477}R^{478}$— or —C(=$NOR^{481}$)$R^{482}$— where said broken line indicates a single bond; or —$CR^{477}R^{478}$ where said broken line indicates a double bond;

$R^{472}$ is a member independently selected from the group consisting essentially of H; hydroxy; bromo, chloro, or fluoro; and —$OR^{479}$;

each $R^{473}$ is a member independently selected from the group consisting essentially of cyano; cyanomethyl; benzyloxy; —$R^{475}$; —CO$_2R^{475}$; —CO$_2(CH_2)_n$($C_6$–$C_{10}$) aryl; —C(Y)$NR^{475}R^{476}$; —C(Y)$NR^{475}(CH_2)_n$($C_6$–$C_{10}$) aryl; —$(CH_2)_n$($C_6$–$C_{10}$) aryl; and —$(CH_2)_n$(5- to 10-membered heteroaryl); where n is an integer selected from 0, 1, 2, and 3; each $R^{473}$ group is substituted by 0 to 3 substituents $R^{474}$; and each $R^{473}$ group is substituted by 0 or 1 substituent $R^{480}$;

each $R^{474}$ is a member independently selected from the group consisting essentially of bromo, chloro, or fluoro; cyano; nitro; ($C_1$–$C_6$) alkyl; ($C_2$–$C_6$) alkenyl; —$OR^{475}$; ($C_3$–$C_7$)cycloalkoxy; —$NR^{475}R^{476}$; —$NR^{475}OR^{476}$; —S(O)$_mR^{475}$ where m is an integer selected from 0, 1, and 2; —CO$_2R^{475}$, —C(=O)$R^{475}$; —SO$_2NR^{475}R^{476}$; —C(=O)$NR^{475}NR^{476}$; —$CR^{475}R^{476}$SO$_2NR^{475}R^{476}$; —$CR^{475}R^{476}$C(=O)$NR^{475}R^{476}$; —NHSO$_2R^{475}$; —NHSO$_2NR^{475}R^{476}$; —NHC(=O)$NR^{476}$; —NHC(=O)($C_1$–$C_6$) alkyl; and —NHC(=O)O($C_1$–$C_6$) alkyl);

each $R^{475}$ and $R^{476}$ is a member independently selected from the group consisting essentially of H; and ($C_1$–$C_6$) alkyl;

$R^{477}$ is a member independently selected from the group consisting essentially of —$R^{473}$; 2-oxo-pyridyl; 3-oxo-pyridyl; 4-oxo-pyridyl; 2-oxo-pyrrolyl; 4-oxo-thiazolyl; 4-oxo-piperidyl; 2-oxo-quinolyl; 4-oxo-quinolyl; 1-oxo-isoquinolyl; 4-oxo-oxazolyl; 5-oxo-pyrazolyl; 5-oxo-isoxazolyl; and 4-oxo-isoxazolyl; where each of said $R^{477}$ groups is substituted by 0 to 3 substituents $R^{474}$;

$R^{478}$ is a member independently selected from the group consisting essentially of —$R^{475}$; cyano; —$(CH_2)_p$($C_6$–$C_{10}$) aryl; and —$(CH_2)_p$(5- to 10-membered heteroaryl); where p is an integer selected from 1, 2, and 3; and where each said $R^{478}$ group is substituted by 0 to 3 substituents $R^{474}$;

$R^{479}$ is a member independently selected from the group consisting essentially of formyl; carbamoyl; thiocarbamyl; ($C_1$–$C_6$) alkyl; ($C_2$–$C_6$) alkenyl; ($C_1$–$C_4$) alkoxy($C_1$–$C_4$) alkyl-; and ($C_1$–$C_6$) alkanoyl; where said alkyl moieties of each of said $R^{479}$ groups is substituted by 0 to 3 substituents independently selected from the group consisting essentially of bromo, chloro, or fluoro; hydroxy; and ($C_1$–$C_4$) alkoxy;

$R^{480}$ is a member independently selected from the group consisting essentially of cyclobutyl; cyclopentyl; cyclohexyl; 2-cyclobuten-1-yl; 2-cyclopenten-1-yl; 3-cyclopenten-1-yl; 2,4-cyclopentadien-1-yl; 3,5-cyclohexadien-1-yl; pyrrolyl; pyrrolidinyl; dioxolanyl; imidazolyl; oxazolyl; imidazolidinyl; pyrazolyl; pyrazolidinyl; pyranyl; piperidinyl; 1,4-dioxanyl; morpholinyl; 1,4-dithianyl; thiomorpholinyl; piperazinyl; 1,3,5-trithianyl; oxazinyl; isoxazinyl; oxathiazinyl; and oxadiazinyl; where each of said $R^{480}$ groups is substituted by 0 to 2 ($C_1$–$C_2$) alkyl;

$R^{481}$ is a member independently selected from the group consisting essentially of H; $(C_1-C_6)$ alkyl; $(C_2-C_6)$ alkenyl; $(C_2-C_6)$ alkynyl; —C(Y)NR$^{475}$R$^{476}$; —C(Y)NH $(C_6-C_{10})$ aryl; —C(Y)$(C_1-C_6)$ alkoxy; —C(Y) $(C_6-C_{10})$ aryloxy; and —C(Y)$(C_1-C_6)$ alkyl;

$R^{482}$ is a member independently selected from the group consisting essentially of phenyl and pyridinyl; where each of said $R^{482}$ groups is substituted by 0 to 3 substituents independently selected from the group consisting essentially of bromo, chloro, or fluoro; $(C_1-C_4)$ alkyl; hydroxy; $(C_1-C_4)$ alkoxy; —NR$^{475}$R$^{476}$; and —S(O)$_m$R$^{475}$, where m is an integer selected from 0, 1, and 2; and, Y is O or S;

—OR, said substituents defining $R^2_a$ and $R^2_b$ comprise a moiety of partial Formulas (VA) through (VM), inclusive:

V (VA)
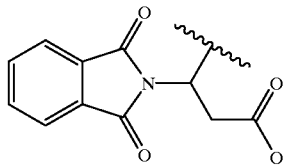

(VB)
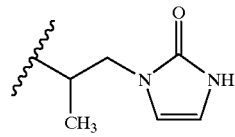

(VC)
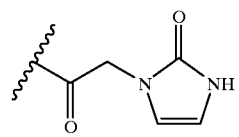

(VD)
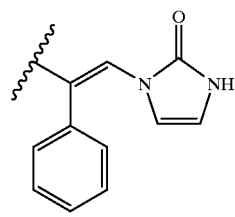

(VE$_a$)
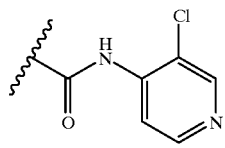

(VE)
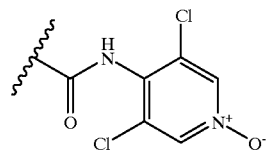

(VF)
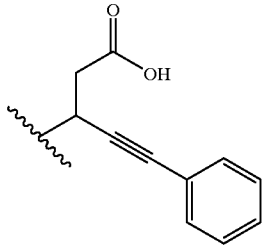

(VG)
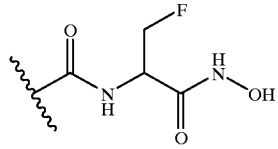

(VH)
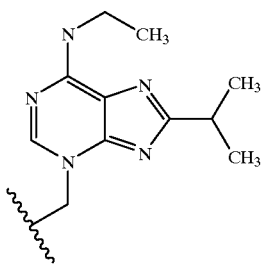

(VI)
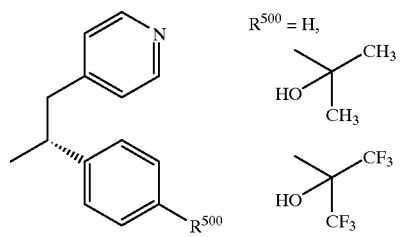

-continued

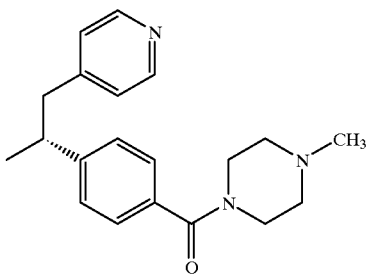
(VJ)

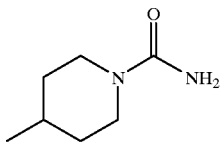
(VK)

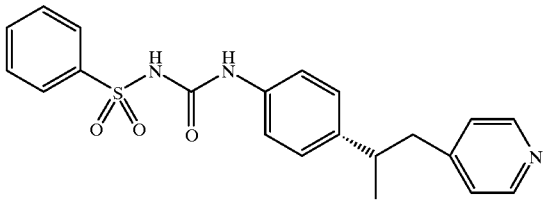
(VL)

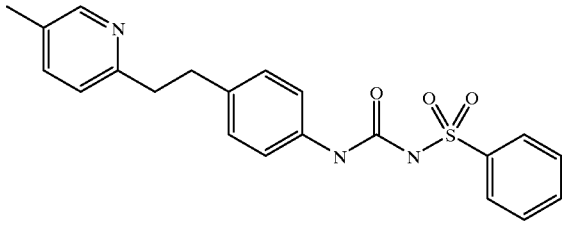
(VM)

Preferred compounds of Formula (IA) or (IB) where $R^2_a$ and $R^2_b$ are as defined under (-IV-) above, include those wherein $R^1$ is ethyl and R is cyclopentyl, cyclohexyl, or $(C_6–C_{10})$aryl.

Other preferred compounds of Formula (IA) or (IB) include those wherein $R^{473}$ is —$(CH_2)_n(C_6–C_{10})$ aryl or —$(CH_2)_n$(5- to 10-membered heteroaryl), where n is an integer selected from 0, 1, 2, and 3; and, more preferably, wherein $R^{473}$ is phenyl or pyridin-4-yl.

Specific embodiments of the compounds of Formula (IA) or (IB) where $R^2_a$ and $R^2_b$ are as defined under (-I-) include those wherein R is cyclopentyl or cyclohexyl, $R^1$ is $(C_1–C_2)$ alkyl, preferably ethyl, one of $R^2_a$ and $R^2_b$ is hydrogen and the other is a substituent of Formula (IC) where the dashed line represents a single bond, m is 0, $R^{113}$ and $R^{114}$ are in a cis relationship to each other, $R^{113}$ is cyano, $R^{115}$ is hydrogen, and $R^{114}$ is carboxy, —$CH_2OH$, or —$CH_2C(=O)NH_2$.

Other specific embodiments of the compounds of Formula (IA) or (IB) include those wherein R is phenyl substituted by fluoro, $R^1$ is $(C_1–C2)$ alkyl, preferably ethyl, one of $R^2_a$ and $R^2_b$ is hydrogen and the other is a substituent of Formula (IC) where the dashed line represents a single bond, $R^{113}$ is cyano, and $R^{115}$ and $R^{114}$ are both hydrogen.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals which are straight or branched moieties containing from one to six, preferably one to four, carbon atoms.

The term "alkoxy", as used herein, unless otherwise indicated, means O-alkyl groups wherein "alkyl" is defined above.

The term "alkenyl", as used herein, unless otherwise indicated, means unsaturated alkyl groups having one or more double bonds wherein "alkyl" is defined above.

The term "cycloalkyl", as used herein, unless otherwise indicated, means saturated monovalent cyclo hydrocarbon radicals containing from three to seven carbon atoms, preferably five or six carbon atoms, including such specific radicals as cyclobutyl, cyclopentyl and cycloheptyl.

The term "aryl", as used herein, unless otherwise indicated, means an organic radical derived from an aromatic hydrocarbon by removal of one hydrogen, comprising a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; and preferably means phenyl.

The term "heterocyclyl" or "heterocyclic", as used herein, unless otherwise indicated, means aromatic and non-aromatic heterocyclic groups containing one or more heteroatoms each selected from O, S and N. Included within this meaning are heterocyclic groups which are benzo-fused ring systems and ring systems substituted with an oxo moiety. Included within the scope of this definition are the following specific groups: acridinyl; benzimidazolyl; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl.

With reference to the $R^{114}$ substituent of partial Formula (IC) of Formula (IA) or (IB), the $(C_3–C_9)$heterocyclic group can be attached to the $(C_1–C_6)$ alkyl group by a nitrogen or, preferably, a carbon atom. An example of a $C_3$ heterocyclic group is thiazolyl, and an example of a $C_9$ heterocyclic group is quinolinyl. Examples of non-aromatic heterocyclic groups are pyrrolidinyl, piperidino, morpholino, thiomorpholino and piperazinyl. Examples of aromatic heterocyclic groups which are preferred are pyridinyl, imidazolyl, pyrimidinyl, pyrazolyl, triazolyl, pyrazinyl, tetrazolyl, furyl, thienyl, isoxazolyl and thiazolyl. A preferred heterocyclic group having a fused benzene ring is benzimidazolyl.

Where heterocyclic groups are specifically recited or covered as substituents for the compound of Formula (IA) or (IB) under (-I-), it is understood that all suitable isomers of such heterocyclic groups are intended. Thus, for example, in the definition of the substituent $R^{114}$, the term "thiazolyl" includes 2-, 4- or 5-thiazolyl; the term "imidazolyl" includes 2-, 4- or 5-inidazolyl; the term "pyrazolyl" includes 3-, 4- or 5-pyrazolyl; the term "oxazolyl" includes 2-, 4- or 5-oxazolyl; the term "isoxazolyl" includes 3-, 4- or 5-isoxazolyl, and so on. Likewise, in the definition of substituent $R^{116}$, the term "pyridyl" includes 2-, 3- or 4-pyridyl.

Certain "aminal" or "acetal"-like chemical structures within the scope of Formula (IA) or (IB) may be unstable. Such structures may occur where two heteroatoms are attached to the same carbon atom. For example, where R is ($C_1$–$C_6$) alkyl substituted by hydroxy, it is possible that the hydroxy may be attached to the same carbon that is attached to the nitrogen atom from which R extends. It is to be understood that such unstable compounds are not within the scope of the present invention.

Preferred compounds of Formula (IA) or (IB) under (-I-) include those wherein $R^2_a$ or $R^2_b$ is a group of the partial Formula ($IC_a$) or ($IC_b$):

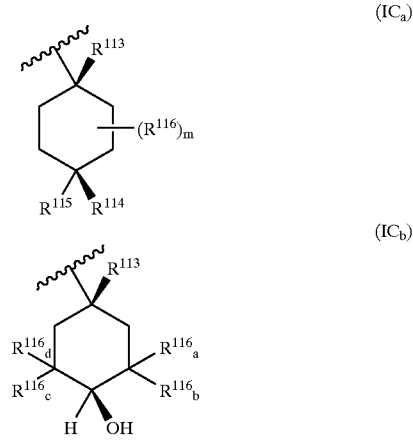

where for partial Formula ($IC_a$) $R^{113}$ and $R^{114}$, especially where $R^{114}$ is —OH, are cis with respect to each other; and for partial Formula ($IC_b$) $R^{116}_a$, $R^{116}_b$, $R^{116}_c$, and $R^{116}_d$ are independently selected from the group consisting essentially of —H; —$CH_3$; —$CF_3$; —$CHF_2$; —$CH_2F$; ethyl, i-propyl; and t-butyl;

Other preferred compounds of Formula (IA) or (IB) under (-I-) include those wherein R is a member independently selected from the group consisting essentially of cyclohexyl, cyclopentyl, cyclobutyl, methylenecyclopropyl, isopropyl, phenyl, and 4-fluoro-phenyl.

Other preferred compounds of Formula (IA) or (IB) under (-I-) include those wherein $R^1$ is ($C_1$–$C_2$) alkyl substituted by 0 to 3 fluorine atoms, and, more preferably, those wherein $R^1$ is ethyl.

Other preferred compounds of Formula (IA) or (IB) under (-I-) include those wherein one of $R^2_a$ and $R^2_b$ is hydrogen and the other is a group of partial Formula (IC) wherein the dashed line attached to the ring carbon atom to which $R^{113}$ is attached represents a single bond.

Other preferred compounds of Formula (IA) or (IB) under (-I-) include those wherein one of $R^2_a$ and $R^2_b$ is hydrogen and the other is a group of partial Formula (IC) wherein the dashed line attached to the ring carbon atom to which $R^{113}$ is attached represents a single bond and $R^{113}$ is cyano.

Other preferred compounds of Formula (IA) or (IB) under (-I-) include those wherein one of $R^2_a$ and $R^2_b$ is hydrogen and the other is a group of partial Formula (IC) wherein the dashed line attached to the ring carbon atom to which $R^{113}$ is attached represents a single bond, m is 0 and $R^{115}$ is hydrogen.

Other preferred compounds of Formula (IA) or (IB) under (-I-) include those wherein one of $R^2_a$ and $R^2_b$ is hydrogen and the other is a group of partial Formula (IC) wherein the dashed line attached to the ring carbon atom to which $R^{113}$ is attached represents a single bond; m is 0; $R^{115}$ is hydrogen; and $R^{114}$ is a member independently selected from the group consisting essentially of —H; —$CH_2OH$; —$C(CH_3)_2$OH; —C(=O)OH; —C(=O)$OCH_3$; —C(=O)$OCH_2CH_3$; and —$CH_2$C(=O)$NH_2$.

Other more preferred compounds of Formula (IA) or (IB) under (-I-) include those wherein R is a member independently selected from the group consisting essentially of cyclobutyl, cyclopentyl, cyclohexyl, and 4-fluoro-phenyl; $R^1$ is ethyl; one of $R^2_a$ and $R^2_b$ is hydrogen and the other is a group of partial Formula ($IC_b$); $R^{113}$ is cyano; $R^{115}$ is hydrogen; $R^{114}$ is —OH, and $R^{113}$ and $R^{114}$ are cis with respect to each other; and $R^{116}_a$, $R^{116}_b$, $R^{116}_c$, and $R^{116}_d$ are each a member independently selected from the group consisting essentially of —H; and —$CH_3$;

Preferred compounds of Formula (IA) or (IB) include those wherein $R^1$ is ethyl.

Other preferred compounds of Formula (IA) or (IB) include those wherein R is a member independently selected from the group consisting essentially of cyclohexyl; cyclopentyl; methylenecyclopropyl; isopropyl; phenyl; and 4-fluoro-phenyl.

Specific preferred compounds of Formula (IA) or (IB) under (-I-) include:

1-(1-Cyclopentyl-3-ethyl-1H-indazol-6-yl)-4-oxocyclohexanecarbonitrile;

Trans-4-cyano4-(1-cyclopentyl-3-ethyl-1H-indazol-6-yl)cyclohexanecarboxylic acid methyl ester;

Cis-4-cyano4-(1-cyclopentyl-3-ethyl-1H-indazol-6-yl)cyclohexanecarboxylic acid methyl ester;

Trans-4-cyano4-(1-cyclopentyl-3-ethyl-1H-indazol-6-yl)cyclohexanecarboxylic acid;

Cis-4-cyano4-(1-cyclopentyl-3-ethyl-1H-indazol-6-yl)cyclohexanecarboxylic acid;

1-(1-Cyclohexyl-3-ethyl-1H-indazol-6-yl)-4-oxocyclohexanecarbonitrile;

Cis-4-cyano-4-(1-cyclohexyl-3-ethyl-1H-indazol6-yl)cyclohexanecarboxylic acid methyl ester;

Trans-4-cyano-4-(1-cyclohexyl-3-ethyl-1H-indazol-6-yl)cyclohexanecarboxylic acid methyl ester;

Cis-4-cyano-4-(1-cyclohexyl-3-ethyl-1H-indazol-6-yl)cyclohexanecarboxylic acid;

Trans-4-cyano-4-(1-cyclohexyl-3-ethyl-1H-indazol-6-yl)cyclohexanecarboxylic acid;

Cis-1-(1-cyclohexyl-3-ethyl-1H-indazole-6-yl)-4-hydroxymethylcyclohexanecarbonitrile;

Cis-4-cyano4-(1-cyclohexyl-3-ethyl-1H-indazol4-yl)cyclohexanecarboxylic acid amide;

Trans-4-cyano-4-(1-cyclohexyl-3-ethyl-1H-indazol-6-yl)cyclohexanecarboxylic acid amide;

Cis-1-(1-cyclohexyl-3-ethyl-1H-indazol6-yl)-4-(1-hydroxy-1-methylethyl)cyclohexanecarbonitrile;

Cis-1-(1-cyclohexyl-3-ethyl-1H-indazol-6-yl)-4-hydroxycyclohexanecarbonitrile;
Cis-1-[3-ethyl-1-(4-fluorophenyl)-1H-indazol-6-yl]-4-hydroxycyclohexanecarbonitrile;
Cis-1-(1-cyclopentyl-3-ethyl-1H-indazol-6-yl)-4-hydroxycyclohexanecarbonitrile;
Cis-1-(1-cyclobutyl-3-ethyl-1H-indazol-6-yl)-4-hydroxycyclohexanecarbonitrile;
Cis-1-(1-cyclopentyl-3-ethyl-1H-indazol6-yl)-4-hydroxy4-methylcyclohexanecarbonitrile;
Trans-1-(1-cyclopentyl-3-ethyl-1H-indazol-6-yl)-4-hydroxy4-methylcyclohexanecarbonitrile;
Cis-4-cyano-4-(1-cyclobutyl-3-ethyl-1H-indazol-6-yl) cyclohexanecarboxylic acid;
Trans-4-cyano4-(1-cyclobutyl-3-ethyl-1H-indazol-6-yl) cyclohexanecarboxylic acid;
6-Bromo-3-ethyl-1-(4-fluorophenyl)-1H-indazole;
4-[3-Ethyl-1-(4-fluorophenyl)-1H-indazol-6-yl]-4-hydroxycyclohexanecarboxylic acid ethyl ester;
4-Cyano-4-[3-ethyl-1-(4-fluorophenyl)-1H-indazol-6-yl] cyclohexanecarboxylic acid ethyl ester;
4-[3-Ethyl-1-(4-fluorophenyl)-1H-indazol-6-yl] cyclohex-3-enecarboxylic acid ethyl ester;
4-Cyano4-(1-cyclohexyl-3-ethyl-1H-indazol6-yl)-cyclohexanecarboxylic acid ethyl ester;
Cis-4-Cyano-4-3-ethyl-1-(4-fluorophenyl)-1H-indazol-6-yl)cyclohexanecarboxylic acid;
4-[3-Ethyl-1-(4-fluorophenyl)-1H-indazol-6-yl] cyclohex-3-enecarboxylic acid; and
4-(1-Cyclohexyl-3-ethyl-1H-indazol6-yl)-4-hydroxycyclohexanecarboxylic acid.

The phrase "pharmaceutically acceptable salt(s)", as used herein, unless otherwise indicated, includes salts of acidic or basic groups which may be present in the compounds of Formula (IA) or (IB). For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts.

Certain species of abovedescribed compounds may have asymmetric centers and therefore exist in different enantiomeric forms. All optical isomers and stereoisomers of the compounds of Formula (IA) or (IB), and mixtures thereof, are considered to be within the scope of the invention. With respect to the compounds of Formula (IA) or (IB), the invention includes the use of a racemate, a single enantiomeric form, a single diastereomeric form, or mixtures thereof. The compounds of Formula (IA) or (IB) may also exist as tautomers. This invention relates to the use of all such tautomers and mixtures thereof.

The present invention further relates to a pharmaceutical composition for the inhibition of phosphodiesterase (PDE) type IV or the production of tumor necrosis factor (TNF) in a mammal comprising a pharmaceutically effective amount of a compound according to the above-described compounds, or a pharmaceutically acceptable salt thereof, and a pharmaceutically acceptable carrier.

The present invention further relates to a method for the inhibition of phosphodiesterase (PDE) type IV or the production of tumor necrosis factor (TNF) by administering to a patient an effective amount of a compound according to the above-described compounds or a pharmaceutically acceptable salt thereof.

Accordingly, the present invention also relates to method of treating or preventing a disease or condition in a mammal in need of such treatment wherein said disease or condition responds favorably to inhibition of PDE4 or production of TNF and is a member selected from the group consisting essentially of asthma; joint inflammation; rheumatoid arthritis; gouty arthritis; rheumatoid spondylitis; osteoarthritis; sepsis; septic shock; endotoxic shock; gram negative sepsis; toxic shock syndrome; acute respiratory distress syndrome; cerebal malaria; chronic obstructive pulmonary disease (COPD), including asthma, chronic bronchitis and pulmonary emphysema; silicosis; pulmonary sarcoidosis; bone resorption diseases; reperfusion injury; graft vs. host reaction; allograft rejections; fever and myalgias due to bacterial, viral or fungal infection including influenza; cachexia secondary to infection or malignancy; cachexia secondary to human acquired immune deficiency syndrome (AIDS); AIDS; HIV infection; ARC (AIDS related complex); keloid formation; scar tissue formation; Crohn's disease; ulcerative colitis; pyresis; multiple sclerosis; type 1 diabetes mellitus; autoimmune diabetes; systemic lupus erythematosis; bronchitis; psoriasis; Bechet's disease; anaphylactoid purpura nephritis; chronic glomerulonephritis; inflammatory bowel disease; leukemia; allergic rhinitis; and dermatitis, comprising administering to said mammal a therapeutically effective amount of a therapeutically active composition of matter comprising a compound of Formula (IA) or (IB), optionally together with a pharmaceutically acceptable carrier therefor.

The present invention further relates to a pharmaceutical composition for the prevention or treatment of the diseases and conditons enumerated above, especially including asthma, in a mammal, comprising a therapeutically effective amount of a compound according to Formula (IA) or (IB), or a pharmaceutically acceptable salt thereof, together with a pharmaceutically acceptable carrier therefor.

This invention further relates to a method of treating or preventing the foregoing specific diseases and conditions by administering to a patient an effective amount of a compound of Formula (IA) or (IB), or a pharmaceutically acceptable salt thereof. In particular, the present invention includes compounds useful in treating or preventing one or members selected from the groups of diseases and conditions consisting essentially of (1) inflammatory diseases and conditions comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory diseases and conditions comprising: acute respiratory distress syndrome, bronchitis, chronic obstructive pulmonary disease (COPD), including asthma, chronic bronchitis and pulmonary emphysema, and silicosis; (3) infectious diseases and conditions comprising: sepsis, septic shock, endotoxic shock, gram negative sepsis, toxic shock syndrome, fever and myalgias due to bacterial, viral or fungal infection, and influenza; (4) immune diseases and conditions comprising: autoimmune diabetes, systemic lupus erythematosis, graft vs. host reaction, allograft rejections, multiple sclerosis, psoriasis, and allergic rhinitis; and (5) other diseases and conditions comprising: bone resorption diseases; reperfusion injury; cachexia secondary to infection, malignancy, or to human acquired immune deficiency syndrome (AIDS), human immunodeficiency virus (HIV) infection, or AIDS related complex (ARC); keloid formation; scar tissue formation; type 1 diabetes mellitus; and leukemia; wherein said compound comprises an inhibitor of phosphodiesterase isozyme 4 (PDE4).

Especially important among the above-recited diseases and conditions which may be treated or prevented using the compounds of the present invention are the inflammatory diseases and conditions and the respiratory diseases and conditions. Among the inflammatory diseases and conditions which are especially significant with regard to successful treatment or prevention using the compounds of the present invention comprise: joint inflammation, rheumatoid arthritis, osteoarthritis, Crohn's disease, and inflammatory bowel disease. Among the respiratory diseases and conditions which are especially significant with regard to successful treatment or prevention using the compounds of the present invention comprise: chronic obstructive pulmonary disease (COPD), especially asthma and chronic bronchitis, as well as, acute respiratory distress syndrome.

The expression "treating or preventing", as used herein with regard to the administration of the compounds of the present invention for therapeutic purposes in the case of various members selected from the many groups of diseases and conditions specifically recited herein, is intended to denote both the therapeutic objective of said administration as well as the therapeutic results actually achieved by said administration. The extent of therapy accomplished by administration of the compounds of the present invention may range from an amelioration to a significant diminishing of the course of the disease involved, and beyond to active treatment of said disease, including a reversal of the disease process itself which is present. The higher or highest degrees of therapeutic effectiveness result in the prevention of any injury, damage, deterioration, or loss of body tissues or organs and basic body functions subsequent to the early stages of degeneration and decline in said body tissues or organs and basic body functions at the onset of the disease involved.

The expression "the early stages of degeneration and decline in body tissues or organs and basic body functions" is intended to mean the very beginning of the initial pathologic changes in said body tissues or organs and basic body functions which define and are the result of a disease process. Said pathologic changes with respect to tissues and organs include changes in the composition and cohesiveness; form and makeup; rigidity, strength, resilience, elasticity, conformational integrity and stability, density, tensile strength and other measures of physical quality; abundance and extent of its presence throughout the body; viability and regenerative capability on both a micro- and macro-level; and the ability to successfully resist various kinds of external stresses including mechanical force and invasion by microorganisms; of said tissues and organs from that present before the onset of said disease process, which result in a degradation and decline of the beneficial and necessary properties characterizing said tissues and organs.

Pathologic changes with respect to body functions are those which inherently arise from the changes above-described with respect to said tissues and organs, and which also, consequently, result in a degradation and decline in the beneficial and necessary performance which characterizes the normal and proper operation of said body functions. These pathologic changes, both with regard to tissues or organs and with respect to body functions, especially include improper repair of the above-discussed early stages of degeneration and decline.

Reaction Schemes 1–4 below illustrate the preparation of the compounds of the present invention:

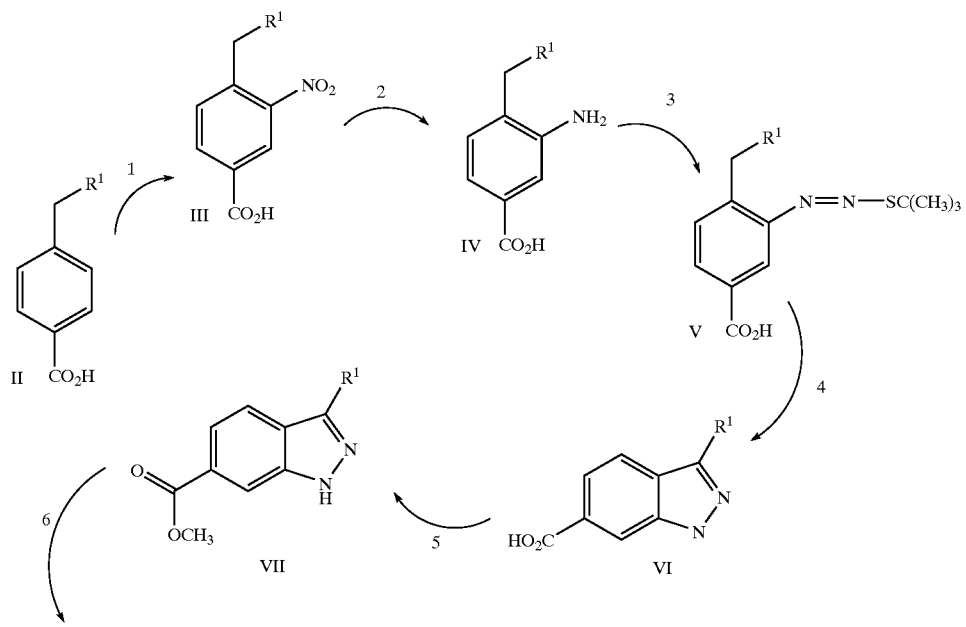

-continued
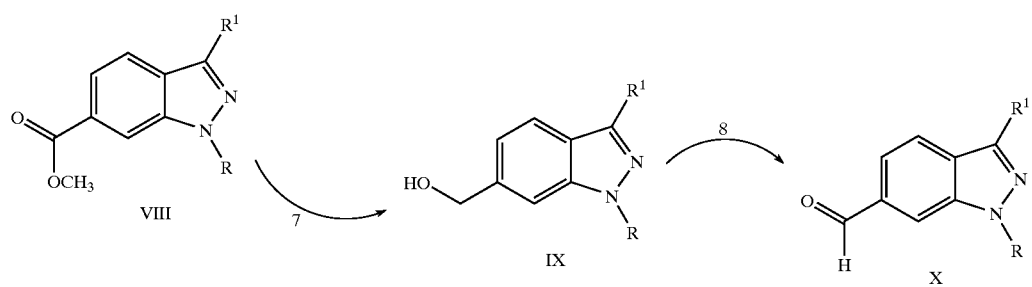
SCHEME 2
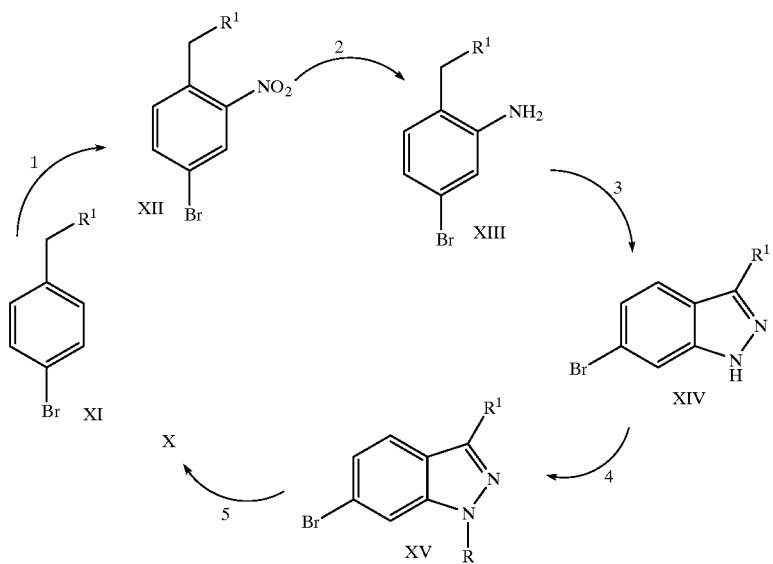
SCHEME 3
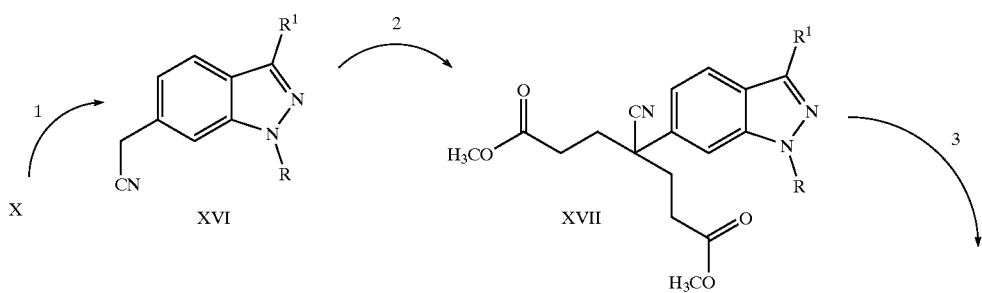

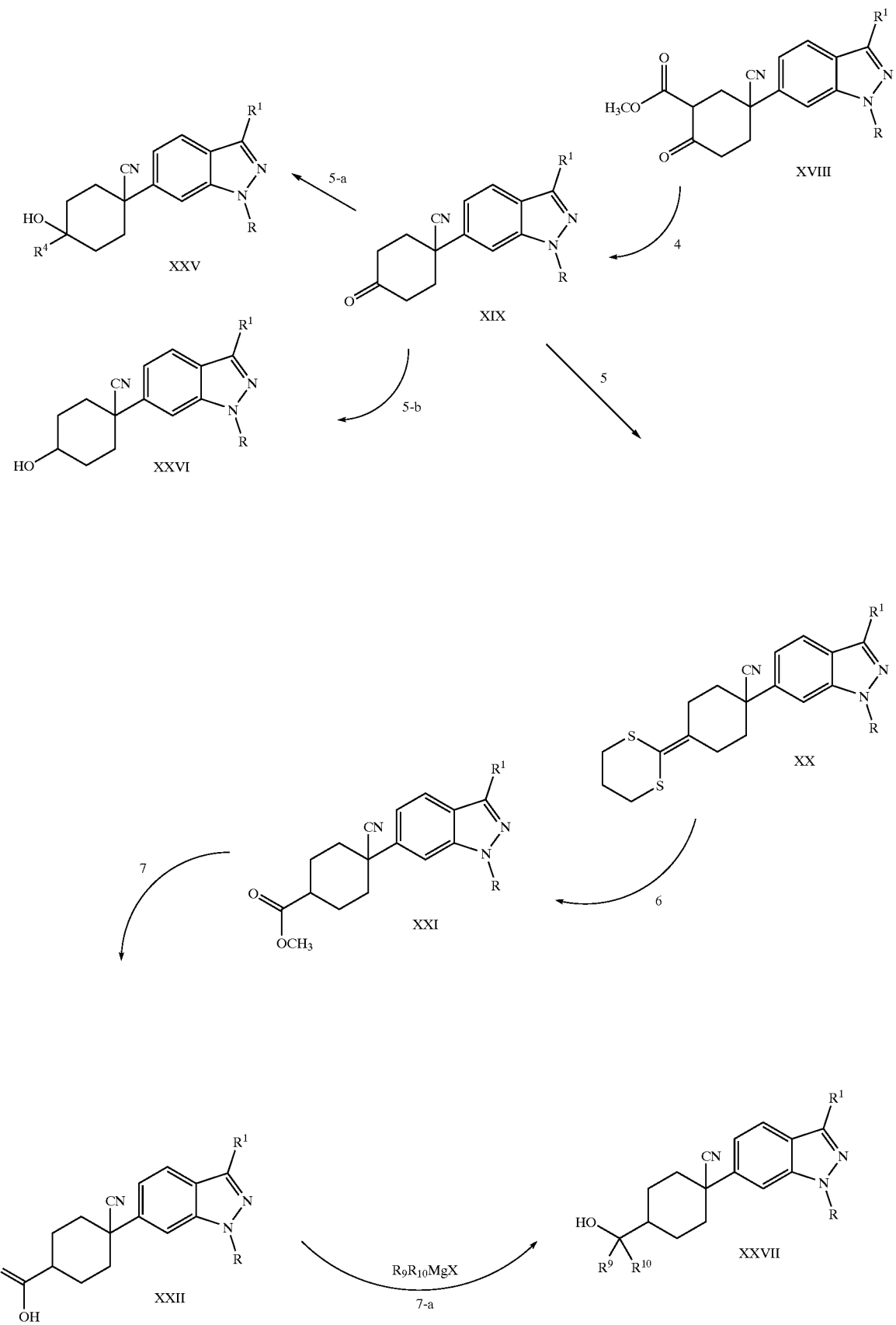

SCHEME 4

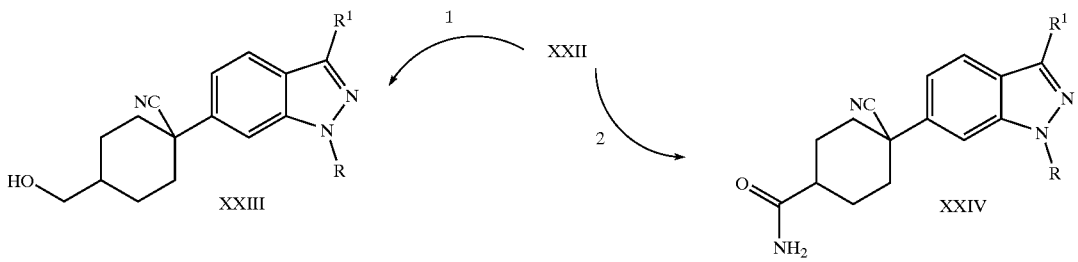

The compounds in the schematic representations above are numbered using Roman numerals in consecutive order, starting with II. These Roman numeral reference numbers are not necessarily related to the Roman numerals used elsewhere in defining the compounds of the present invention. Unless otherwise indicated, R and $R^1$ in the reaction schemes are defined the same as elsewhere herein.

The preparation of compounds of Formula (IA) or (IB) can be carried out by one skilled in the art according to one or more of the synthetic methods outlined in Schemes 1–4 above and the examples referred to below. In Step 1 of Scheme 1, the carboxylic acid of Formula II, which is available from known commercial sources or can be prepared according to methods known to those skilled in the art, is nitrated under standard conditions of nitration ($HNO_3$/$H_2SO_4$, 0° C.) and the resulting nitro derivative of Formula III is hydrogenated in Step 2 of Scheme 1 using standard hydrogenation methods ($H_2$-Pd/C under pressure) at ambient temperature (20–25° C.) for several hours (2–10 hours) to provide the compound of Formula IV. In Step 3 of Scheme 1, the amino benzoic acid of Formula IV is reacted with a base such as sodium carbonate under aqueous conditions and gently heated until mostly dissolved. The reaction mixture is chilled to a lower temperature (about 0° C.) and treated with sodium nitrate in water. After about 15 minutes, the reaction mixture is slowly transferred to an appropriate container holding crushed ice and a strong acid such as hydrochloric acid. The reaction mixture is stirred for 10–20 minutes and then added, at ambient temperature, to a solution of excess tert-butyl thiol in an aprotic solvent such as ethanol. The reaction mixture is acidified to a pH of 4–5 through addition of an inorganic base, preferably saturated aqueous $Na_2CO_3$, and the reaction mixture is allowed to stir at ambient temperature for 1–3 hours. Addition of brine to the reaction mixture, followed by filtration, provides the sulfide of Formula V.

In Step 4 of Scheme 1, the sulfide of Formula V is converted to the corresponding indazole carboxylic acid of Formula VI by reacting the sulfide of Formula V with a strong base, preferably potassium tert-butoxide, in dimethyl sulfoxide (DMSO) at ambient temperature. After stirring for several hours (1–4 hours), the reaction mixture is acidified with a strong acid, such as hydrochloric or sulfuric acid, and then extracted using conventional methods. In Step 5 of Scheme 1, the indazole carboxylic acid of Formula VI is converted to the corresponding ester of Formula VII by conventional methods known to those skilled in the art. In Step 6 of Scheme 1, the compound of Formula VII is provided through alkylation of the ester of Formula VII by subjecting the ester to conventional alkylation conditions (strong base/various alkylating agents and, optionally, a copper catalyst such as $CuBr_2$) in a polar aprotic solvent, such as tetrahydrofuran (THF), N-methylpyrrolidinone or dimethylformamide (DMF), at ambient or higher temperature (25–200° C.) for about 6–24 hrs, preferably about 12 hours. In Step 7 of Scheme 1, the compound of Formula VII is converted to the corresponding alcohol of IX by following conventional methods known to those skilled in the art for reducing esters to alcohols. Preferably, the reduction is effected through use of a metal hydride reducing agent, such as lithium aluminum hydride, in a polar aproptic solvent at a low temperature (about 0° C.). In Step 8 of Scheme 1, the alcohol of Formula IX is oxidized to the corresponding aldehyde of Formula X according to conventional methods known to those skilled in the art. For example, the oxidation can be effected through use of a catalytic amount of tetrapropylammonium perrutenate and excess N-methylmorpholine-N-oxide, as described in *J. Chem. Soc., Chem. Commun.*, 1625 (1987), in an anhydrous solvent, preferably methylene chloride.

Scheme 2 provides an alternative method of preparing the aldehyde of Formula X. In Step 1 of Scheme 2, the compound of Formula XI is nitrated using conventional nitration conditions (nitric and sulfuric acid) to provide the compound of Formula XII. In Step 2 of Scheme 2, the nitro derivative of Formula XII is reduced to the corresponding amine of Formula XIII according to conventional methods known to those skilled in the art. Preferably, the compound of Formula XII is reduced to the amine of Formula XII using anhydrous stannous chloride in an anhydrous aprotic solvent such as ethanol. In Step 3 of Scheme 2, the amine of Formula XIII is converted to the corresponding indazole of Formula XIV by preparing the corresponding diazonium fluoroforates as described in A. Roe, *Organic Reactions*, Vol. 5, Wiley, New York, 1949, pp. 198–206, followed by phase transfer catalyzed cyclization as described in R. A. Bartsch and I. W. Yang, *J. Het. Chem.* 21, 1063 (1984). In Step 4 of Scheme 2, alkylation of the compound of Formula XIV is performed using standard methods known to those skilled in the art, e.g., strong base, polar aprotic solvent and an alkyl halide, to provide the N-alkylated compound of Formula XV. In Step 5 of Scheme 2, the compound of Formula XV is subjected to metal halogen exchange employing an alkyl lithium, such as n-butyl lithium, in a polar aprotic solvent, such as THF, at low temperature (–50° C. to 100° C., with –78° C. being preferred) followed by quenching with DMF at low temperature and warming to ambient temperature to provide the aldehyde compound of Formula X.

Scheme 3 illustrates the preparation of a compound of Formula XXII which is a compound of Formula (IA) or (IB) wherein $R^2_a$ or $R^2_b$ is a ring moiety of Formula (IC). In Step 1 of Scheme 3, the aldehyde moiety of the compound of Formula X is converted to an appropriate leaving group, such as a halogen, mesylate or another leaving group familiar to those skilled in the art, followed by reacting the resulting compound with sodium cyanate in a polar solvent such as DMF to provide the compound of Formula XVI. In Step 2 of Scheme 3, the compound of Formula XVI is reacted under basic conditions with methyl acrylate or related derivatives depending on the $R^2_a$ or $R^2_b$ group to be added, in an aprotic solvent such as ethylene glycol dimethyl ether (DME) at high temperature, preferably at reflux, to provide the compound of Formula XVII. In Step 3 of Scheme 3, the compound of Formula XVII is converted to the compound of Formula XVIII using a strong base, such as sodium hydride, and a polar aprotic solvent, such as DMF or THF, at elevated temperature, preferably at reflux.

In Step 4 of Scheme 3, the compound of Formula XVIII is decarboxylated using conventional methods, such as using sodium chloride in DMSO at a temperature of about 140° C., to provide the compound of Formula XIX. In Step 5 of Scheme 3, derivatization of the compound of Formula XIX to the corresponding dithian-2-ylidine cyclohexane carbonitrile of Formula XX is done by reaction with 2-lithio-1, 3-dithiane. In Step 5-a of Scheme 3, further derivatization of the compound of Formula XIX to the corresponding cyclohexane carbonitrile of Formula XXV which is para-substituted on the cyclohexane group with an hydroxyl moiety and an $R^4$ substituent, e.g., methyl, is carried out by reacting the ketone with a nucleophilic reagent, e.g., an alkyllithium compound or a Grignard reagent in accordance with procedures well known in the art. In Step 5-b of Scheme 3, further derivatization of the compound of Formula XIX to the corresponding cyclohexane carbonitrile of Formula XXVI which is para-substituted on the cyclohexane group with an hydroxyl moiety, is carried out by reducing the ketone with, e.g., lithium aluminum hydride or sodium borohydride in accordance with procedures well known in the art. In Step 6 of Scheme 3, the compound of Formula XX is converted to the corresponding ester of Formula XXI using mercury (II) chloride and perchloric acid in a polar protic solvent such as methanol. In Step 7 of Scheme 3, the compound of Formula XXI is converted through hydrolysis to the corresponding carboxylic acid of Formula XXII using a standard method of hydrolysis, such as using aqueous sodium hydroxide in a polar solvent, or any of numerous existing hydrolysis methods known to those skilled in art as described in T. Green and P. G. M. Wets, *Protecting Groups in Organic Synthesis*, 2nd Edition, John Wiley and Sons, New York (1991). The synthetic steps described for Scheme 3 are analogous to the synthetic methods provided for the preparation of corresponding catechol-containing compounds in PCT published applications WO 93/19751 and WO 93/17949.

Other compounds of Formula (IA) or (IB) wherein one of $R^2_a$ or $R^2_b$ is selected from moieties (IC), (ID), (IE) and (IF), can be prepared from one or more of the intermediate compounds described in Schemes 1–3. In particular, the aldehyde of Formula X or the keto compound of Formula XIX can be used to prepare various compounds of Formula (IA) or (IB). Any of the various $R^2_a$ or $R^2_b$ moieties of formulas (IC), (ID), (IE) or (IF) can be introduced into one or more of the intermediate compounds referred to above using synthetic methods provided for corresponding non-indazole analogs in PCT published applications WO 93/19748, WO 93/19749, WO 93/09751, WO 93/19720, WO 93/19750, WO 95/03794, WO 95/09623, WO 95/09624, WO 95109627, WO 95/09836, and WO 95/09837. For example, with reference to Step 1 of Scheme 4, the carboxylic acid of Formula XXII can be converted to the alcohol of Formula XXIII by reduction with various metal hydrides in a polar solvent as described in Example 9, referred to below, and in accordance with synthetic methods provided for corresponding non-indazole analogs in PCT published applications publication numbers WO 93/19747, WO 93/19749 and WO 95/09836. Further, with reference to Step 2 of Scheme 4, the carboxylic acid of Formula XXII can be converted to the corresponding carboxamide of Formula XXIV through conversion to an intermediate acid chloride using conventional synthetic methods, and then reacting the acid chloride with ammonia in an aprotic solvent. Other carboxamide analogs of Formula XXIV can be prepared through reaction of the acid chloride intermediate with various primary or secondary amines according to conventional methods known to those skilled in the art and as described in the PCT published applications referred to above.

Other compounds of Formula (IA) or (IB) can be prepared from the intermediate compound of Formula XIX in accord with synthetic methods provided for corresponding non-indazole analogs in the PCT published applications referred to above. Compounds of Formula (IA) or (IB) wherein $R^2_a$ or $R^2_b$ is a moiety of partial Formula (IC), and either $R^{114}$ ($R^4$) or R is H, can be prepared from the keto intermediate of Formula XIX by reaction with a base such as lithium diisopropylamine in a polar aprotic solvent, such as THF, and excess N-phenyltrifluoromethylsulfonamide as described in PCT published application WO 93/19749 for corresponding non-indazole analogs. Compounds of Formula (IA) or (IB) wherein $R^2_a$ or $R^2_b$ is a moiety of partial Formula (IC), $R^{114}$ ($R^4$) is hydrogen, and $R^{115}$ ($R^5$) is —$CO_2CH_3$ or —$CO_2H$ prepared from the keto intermediate of Formula XIX through reaction with triflic anhydride in the presence of a tertiary amine base followed by reaction of the resulting triflate with (triphenylphosphine)palladium and carbon monoxide in the presence of an alcohol or amine to provide the methyl ester compounds of Formula (IA) or (IB) wherein $R^{115}$ ($R^5$) is —$CO_2CH_3$. The methyl ester compound can be hydrolyzed to obtain the corresponding carboxylic acid compound by employing standard methods for hydrolysis such as sodium or potassium hydroxide in aqueous methanol/tetrahydrofuran. Such synthetic methods are further described in PCT published application WO 93/19749 for corresponding non-indazole analogs.

Other compounds of Formula (IA) or (IB) can be prepared from the intermediate compound of Formula XIX in accord with synthetic methods described for corresponding non-indazole analogs in the published PCT applications referred to above. Compounds of Formula (IA) or (IB) wherein $R^2_a$ or $R^2_b$ is a moiety of partial Formula (IC), $R^{115}(R^5)$ is hydrogen, and $R^{114}(R^4)$ is hydroxy, can be prepared through reaction of the intermediate of Formula XIX with an appropriate reducing agent such as lithium borohydride, diamyl borane, lithium aluminum tris(tert-butoxide), or sodium borohydride in a suitable non-reacting solvent such as 1,2-dimethoxy ethane, THF or alcohol. Compounds of Formula (IA) or (IB) wherein $R^2_a$ or $R^2_b$ is a moiety of Formula (IC), $R^{115}$ ($R^5$) is hydrogen and $R^{114}$ ($R^4$) is —$NH_2$, —$NHCH_3$, or —$N(CH_3)_2$, can be prepared by reacting the intermediate of Formula XIX with an ammonium salt, such as ammonium formate, methylamine hydrochloride or dimethylamine hydrochloride, in the presence of sodium cyanoborohydride in an appropriate solvent such as alcohol.

Alternatively, compounds of Formula (IA) or (IB) wherein $R^2_a$ or $R^2_b$ is a moiety of Formula (IC), $R^{114}$ ($R^4$) is amino, and $R^{115}$ ($R^5$) is hydrogen, can be prepared by reacting the corresponding alcohol of Formula (IA) or (IB)

where $R^{14}$ ($R^4$)=OH and $R^{115}$ ($R^5$)=H, with a complex of an azadicarboxylate ester in the presence of an imide or phthalimide followed by reaction in an alcoholic solvent such as ethanol. Compounds of Formula (IA) or (IB) wherein $R^2_a$ or $R^2_b$ is a moiety of Formula (IC), $R^{115}$ ($R^5$) is H, and $R^{114}$ ($R^4$) is —$SR^{124}$ can be prepared by reacting the corresponding compound wherein $R^{114}$ ($R^4$) is a leaving group such as mesylate, tosylate, bromine or chlorine, with a metal salt of mercaptan such as $NaSR^{124}$ in an appropriate aprotic solvent. Corresponding compounds of Formula (IA) or (IB) wherein $R^{14}$ ($R^4$) is —SH can be prepared by reacting the corresponding alcohol $R^{114}$ ($R^4$)=OH, with a complex of a phosphine, such as triphenyl phosphine, and an azidocarboxylate ester in the presence of thiolacetic acid followed by hydrolysis of the resulting thioacetate. Furthermore, compounds of this structure wherein $R^{114}$ ($R^4$) is hydroxy can be interconverted using a standard alcohol inversion procedure known to those skilled in the art. The foregoing compounds of Formula (IA) or (IB) wherein $R^2_a$ or $R^2_b$ is a moiety of Formula (IC), $R^{115}$ ($R^5$) is hydrogen, and $R^{14}$ ($R^4$) is hydroxy, —SH or —$NH_2$, can be converted to various other compounds of Formula (IA) or (IB) through one or more synthetic methods described in PCT published applications WO 93/19751 and WO 93/19749 for corresponding non-indazole analogs.

Compounds of Formula (IA) or (IB) wherein $R^2_a$ or $R^2_b$ is a moiety of Formula (IC) and the dashed line represents a double bond attached to the ring carbon atom to which substituent $R^{113}$ ($R^3$) is attached, can be prepared from the intermediate of Formula XIX by following one or more synthetic methods provided for the preparation of corresponding non-indazole analogs in PCT published application WO 93/19720. Compounds of Formula (IA) or (IB) wherein $R^2_a$ or $R^2_b$ is a moiety of Formula (IC), and $R^{114}$ ($R^4$) and $R^{115}$ ($R^5$) are taken together to form =O or =$R^{118}$, wherein $R^{118}$ is as defined above, can be prepared from the corresponding ketone intermediate of formula XIX following one or more synthetic methods provided for corresponding non-indazole analogs in PCT published application WO 93/19750. Other compounds of Formula (IA) or (IB) wherein $R^2_a$ or $R^2_b$ is a moiety of Formula (IC) and $R^{114}$ ($R^4$) and $R^{115}$ ($R^5$) are taken together as =$R^{118}$ can be prepared from the intermediate of Formula XIX following one or more synthetic methods provided for the preparation of corresponding non-indazole analogs in PCT published application WO 93/19748.

Compounds of Formula (IA) or (IB) wherein $R^2_a$ or $R^2_b$ is a moiety of Formula (ID) can be prepared from one or more of the intermediates referred to above, such as the bromoindazole intermediate of Formula XV, following one or more synthetic methods provided for the preparation of corresponding non-indazole analogs in PCT published applications WO 95/09627, WO 95/09624, WO 95/09623, WO 95/09836 and WO 95/03794. Compounds of Formula (IA) or (IB) wherein $R^2_a$ or $R^2_b$ is a moiety of Formula (IE) can be prepared from the intermediate of Formula XV following one or more of synthetic methods provided for the preparation of corresponding non-indazole analogs in PCT published applications WO 95/09624 and WO 95/09837. Compounds of Formula (IA) or (IB) wherein $R^2_a$ or $R^2_b$ is a moiety of Formula (IF) can be prepared from the bromoindazole intermediate of Formula XV employing one or more synthetic methods provided for the preparation of the corresponding catechol-containing analogs in PCT published applications WO 95/09627, WO 95/09623 and WO 95109624.

Particularly preferred compounds of the present invention are those represented by Formulas (I-i) and (I-ii):

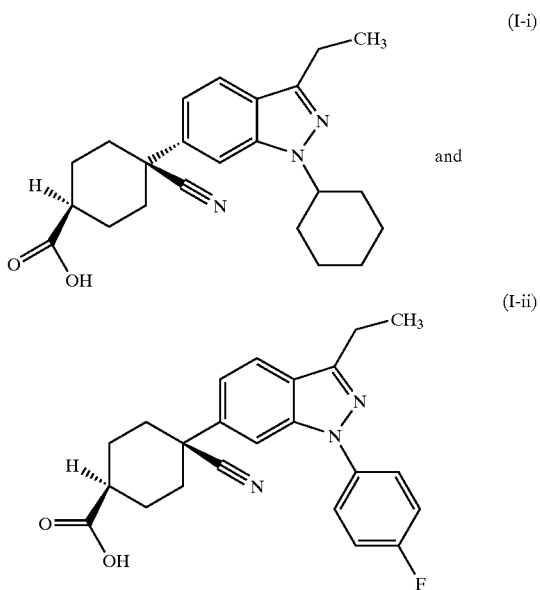

A method for the preparation of the compound of Formula (I-ii) is described in further below-recited Example 23. It is also possible to prepare said compound in accordance with the synthesis method described in above-depicted Scheme 2 and Scheme 3, using as the starting material for said method the compound prepared as described in below-recited Example 20, and represented by Formula (XV-i):

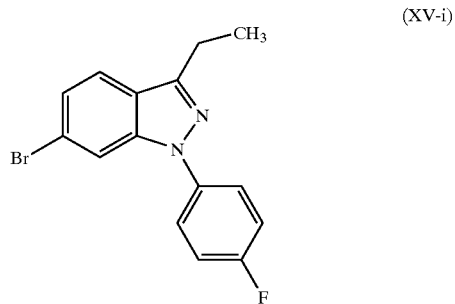

The preferred compound depicted in Formula (I-i)above may be prepared in accordance with the synthesis methods described in above-depicted Scheme 1, Scheme 2, and Scheme 3, and as further detailed in the below-recited Examples. Another, preferred, method of preparing said compound may also be employed, and is represented in the following synthesis Scheme 5, which is a more generalized representation of the above-mentioned preferred method of preparing said above-described preferred compound of the present invention.

SCHEME 5

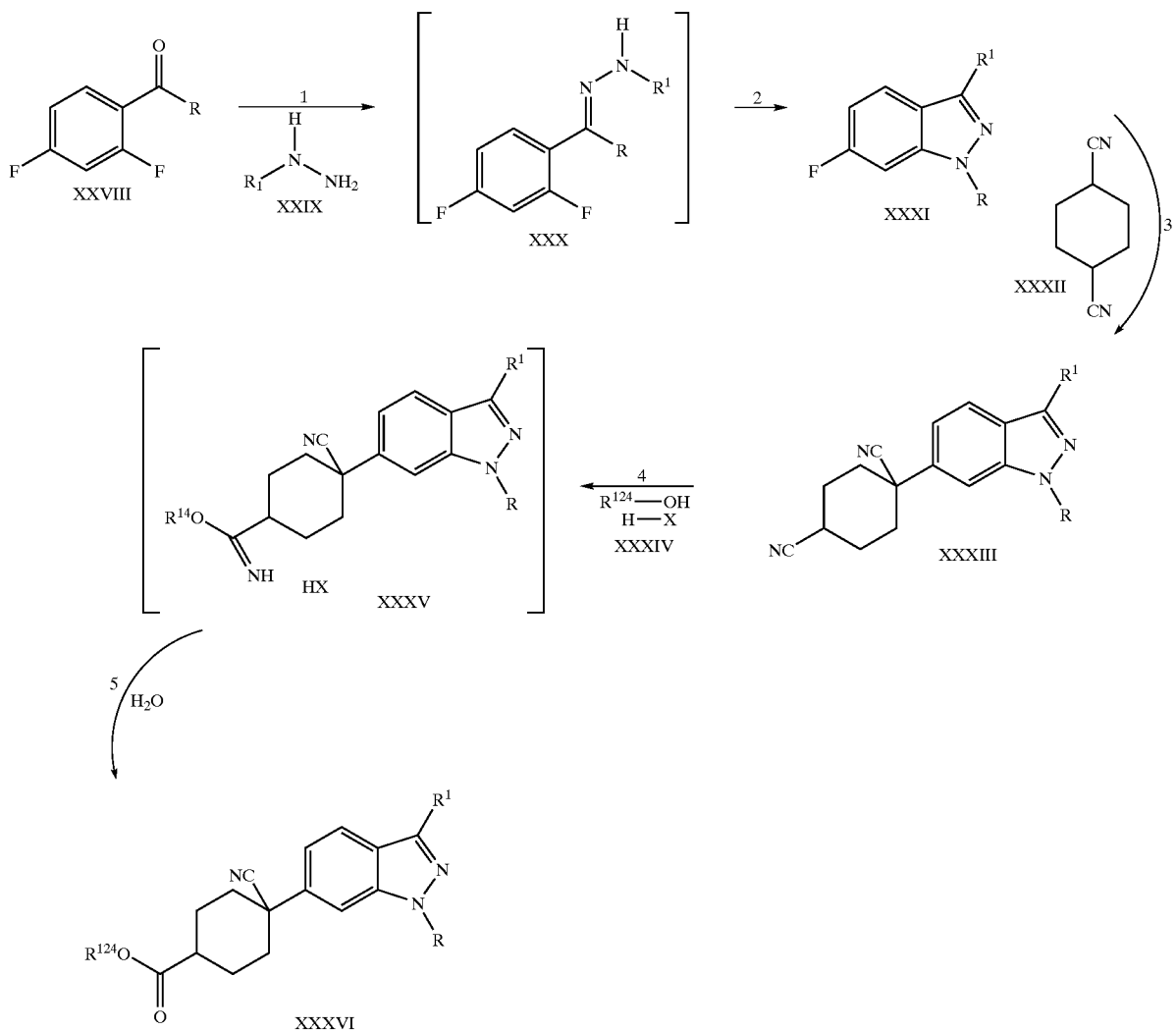

As illustrated, the starting material of Formula XXVIII is reacted with a hydrazine of Formula XXIX and the in situ product of Formula XXX is heated without separation to yield an indazole of Formula XXXI, which is in turn reacted with dicyanocyclohexane of Formula XXXII to yield the cyano-analog of said above-described preferred compound of Formula XXXIII.

In Step 1 of Scheme 5, the compound of Formula XXVIII is treated with a hydrazine derivative of Formula XXIX and an acid, preferably ammonium acetate, in a solvent such as heptane, tetrahydrofuran, xylenes, toluene, or mesitylene, or a mixture of two or more of the foregoing solvents, preferably toluene, to provide the compound of Formula XXX. In general, the compound of Formula XXX need not be separated or isolated from the reaction mixture.

In Step 2 of Scheme 5, the reaction mixture containing the compound of Formula XXX is heated at a temperature between about 75° C. and about 200° C., preferably between about 90° and 120° C., for a period of about 2 hours to 48 hours, preferably 12 hours, to provide the compound of Formula XXXI.

Alternatively, the process of Step 1 of Scheme 5 may be accomplished using a salt of the hydrazine derivative, such as the hydrochloride, hydrobromide, mesylate, tosylate, or oxalate salt of said compound, preferably the mesylate salt, which is reacted with a base, such as sodium or potassium acetate, in a solvent such as heptane, tetrahydrofuran, xylenes, toluene, or mesitylene, or a mixture of two or more of the foregoing solvents, preferably toluene.

In Step 3 of Scheme 5, the compound of Formula XXXI is treated with the compound of Formula XXXII in the presence of a base such as lithium bis(trimethylsilyl)amide, sodium bis(trimethylsilyl)amide, potassium bis(trimethylsilyl)amide, lithium diisopropylamide, or lithium 2,2,6,6-tetramethylpiperidine, preferably potassium bis(trimethylsilyl)amide, in a solvent such as tetrahydrofuran, toluene, or xylenes, preferably toluene, at a temperature between about 25° C. and about 125° C., preferably about 100° C., for a period 1 hour to 15 hours, preferably 5 hours, to provide compound of Formula XXXIII.

In Step 4 of Scheme 5, the compound of Formula XXXIII is treated with an acid such as hydrochloric acid, hydrobromic acid, sulfuric acid, p-toluenesulfonic acid, methanesulfonic acid, or trifluoromthanesulfonic acid, preferably hydrochloric acid, in a solvent of the Formula XXXIV, ie., $R^{124}$—OH wherein $R^{124}$ is as defined herein, e.g., $(C_1-C_6)$ alkyl, such as methanol, ethanol, propanol, isopropanol, preferably ethanol, at a temperature between 0° C. and 50° C., preferably ambient temperature (20–25° C.) for a period of 1 hour to 48 hours, preferably 14 hours, to provide a A particular version of the synthesis of Scheme 5 above carried out with reactants suitable for obtaining the preferred cyclohexanecarboxylic acid compound of the present invention, is illustrated below in Scheme 6:

SCHEME 6

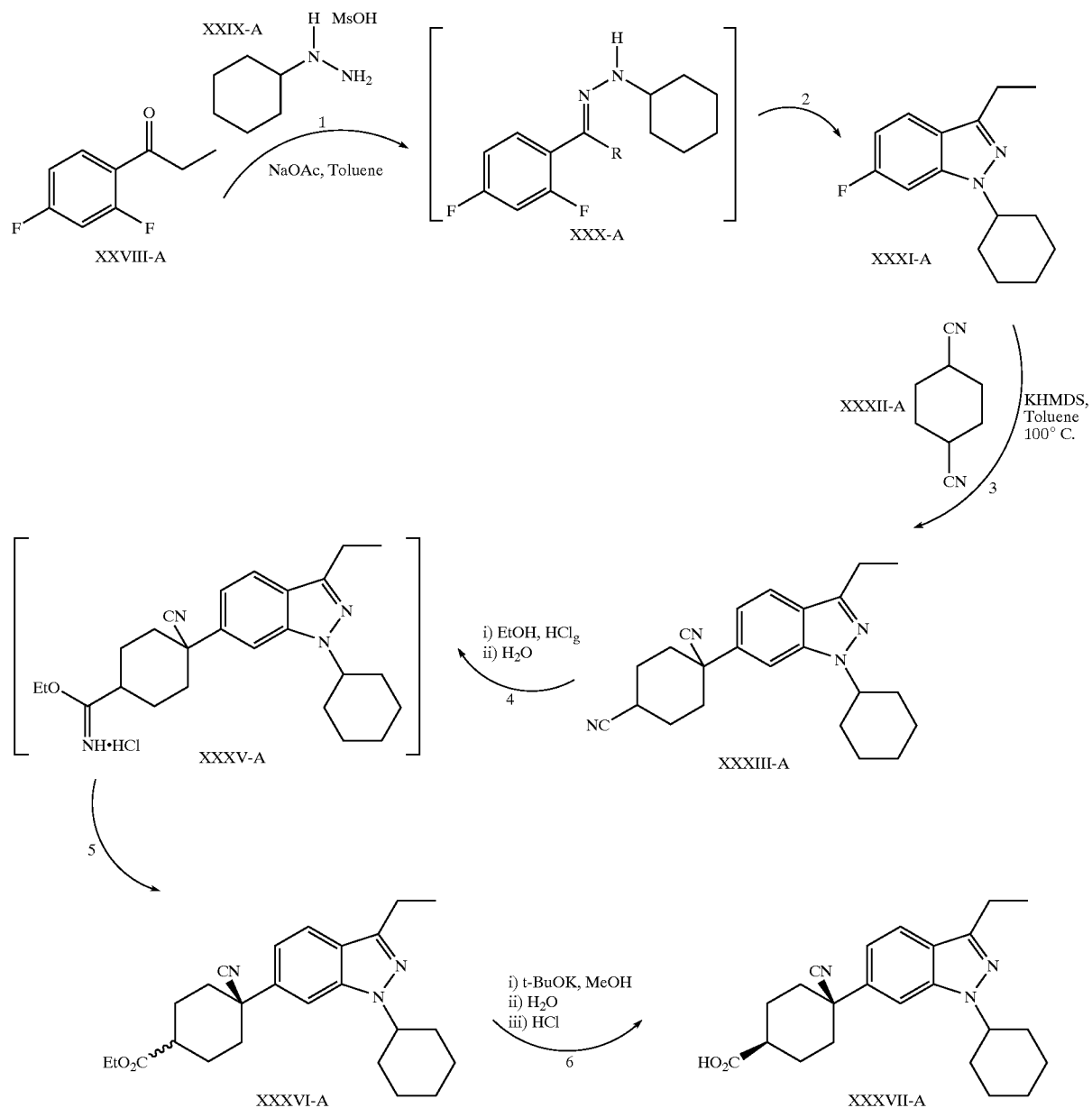

compound of Formula XXXV. In general, the compound of Formula XXXV need not to be separated or isolated from the reaction mixture.

In step 5 of Scheme 5, the compound of Formula XXXV is treated with water in a solvent such as toluene, ethyl acetate, diisopropyl ether, methyl tert-butyl ether, or dichloromethane, preferably toluene, at a temperature between about 0° C. and 50° C., preferably ambient temperature (20–25° C.) for a period of 1 hour to 24 hours, preferably 8 hours, to provide a compound of Formula XXXVI.

Scheme 7 set out below illustrates a procedure to facilitate the handling and purification of the indazole intermediate of Formula XXXI which is described above in reference to Scheme 5. In Step 1 of Scheme 7, the indazole of Formula XXXI is treated with an acid, such as hydrobromic, hydrochloric, or sulfuric acid, preferably hydrobromic acid, in a solvent such as toluene, xylenes, acetic acid, or ethyl acetate, preferably toluene, at a temperature ranging from 0° C. to ambient temperature (20–25° C.), preferably ambient temperature, to form a salt of the compound of Formula XXXVIII, wherein HX indicates the acid used to prepare the salt and X is the anion of said acid. The salt may be separated and purified according to methods familiar to those skilled in the art. In Step 2 of Scheme 7, the salt is converted back to the free base. In this step, the salt of the compound of Formula XXXVIII is treated with an aqueous base, such as sodium hydroxide, potassium hydroxide, sodium carbonate, sodium bicarbonate, potassium carbonate, or potassium bicarbonate, preferably sodium hydroxide, in a solvent such as hexane, toluene, dichloromethane, diisopropyl ether, methyl tert-butyl ether, or ethyl acetate, preferably toluene, at a temperature ranging from 0° C. to ambient temperature (20–25° C.), preferably ambient temperature, for a period of 5 minutes to 1 hour, preferably 20 minutes, to provide the compound of Formula XXXI.

SCHEME 7

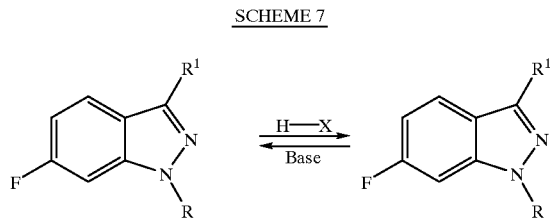

The compounds of the Formulas XXVIII-XXXVIII may have asymmetric carbon atoms and therefore exist in different enantiomeric forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound, e.g., alcohol, separating the diastereomers and converting, e.g., hydrolyzing, the individual diastereomers to the corresponding pure enantiomers. The use of all such isomers, including diastereomer mixtures and pure enantiomers, are considered to be part of the present invention.

Further details concerning the above-identified synthesis methods which are preferred for preparing the above-recited preferred compound of the present invention may be found in copending provisional U.S. Ser. No. 60/064,211 (Attorney Docket No. PC10004), filed Nov. 4, 1997, which is incorporated herein by reference in its entirety.

Pharmaceutically acceptable acid addition salts of the compounds of this invention include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid. Pharmaceutically acceptable cationic salts of the compounds of this invention of Formula (IA) or (IB) wherein, for example, $R^3$ is $CO_2R^9$, and $R^9$ is hydrogen, include, but are not limited to, those of sodium, potassium, calcium, magnesium, ammonium, N,N'-dibenzylethylenediamine, N-methylglucamine (meglumine), ethanolamine, tromethamine, and diethanolamine.

For administration to humans in the curative or prophylactic treatment of inflammatory diseases, oral dosages of a compound of Formula (IA) or (IB) or a pharmaceutically acceptable salt thereof (the active compounds) are generally in the range of 0.1–1000 mg daily for an average adult patient (70 kg). Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally, topically, and rectally (suppositories). In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substance; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The active compounds may also be administered to a mammal other than a human. The dosage to be administered to a mammal will depend on the animal species and the disease or disorder being treated. The active compounds may be administered to animals in the form of a capsule, bolus, tablet or liquid drench. The active compounds may also be administered to animals by injection or as an implant. Such formulations are prepared in a conventional manner in accordance with standard veterinary practice. As an alternative the compounds may be administered with the animal feedstuff and for this purpose a concentrated feed additive or premix may be prepared for mixing with the normal animal feed.

The ability of the compounds of Formula (IA) or (IB) or the pharmaceutically acceptable salts thereof to inhibit PDE4 may be determined by the following assay.

Thirty to forty grams of human lung tissue is placed in 50 ml of pH 7.4 Tris/phenylmethylsulfonyl fluoride (PMSF)/sucrose buffer and homogenized using a Tekmar Tissumizer® (Tekmar Co., 7143 Kemper Road, Cincinnati, Ohio 45249) at full speed for 30 seconds. The homogenate is centrifuged at 48,000×g for 70 minutes at 4° C. The supernatant is filtered twice through a 0.22 mm filter and applied to a Mono-Q FPLC column (Pharmacia LKB Biotechnology, 800 Centennial Avenue, Piscataway, N.J. 08854) pre-equilibrated with pH 7.4 Tris/PMSF Buffer. A flow rate of 1 ml/minute is used to apply the sample to the column, followed by a 2 ml/minute flow rate for subsequent washing and elution. Sample is eluted using an increasing, step-wise NaCl gradient in the pH 7.4 Tris/PMSF buffer. Eight ml fractions are collected. Fractions are assayed for specific PDE4 activity determined by [$^3$H]cAMP hydrolysis and the ability of a known PDE4 inhibitor (e.g. rolipram) to inhibit that hydrolysis. Appropriate fractions are pooled, diluted with ethylene glycol (2 ml ethylene glycol/5 ml of enzyme prep) and stored at $-20°$ C. until use.

Compounds are dissolved in dimethylsulfoxide (DMSO) at a concentration of 10 mM and diluted 1:25 in water (400 mM compound, 4% DMSO). Further serial dilutions are made in 4% DMSO to achieve desired concentrations. The final DMSO concentration in the assay tube is 1%. In duplicate the following are added, in order, to a 12×75 mm glass tube (all concentrations are given as the final concentrations in the assay tube).

i) 25 ml compound or DMSO (1%, for control and blank)
ii) 25 ml pH 7.5 Tris buffer
iii) [$^3$H]cAMP (1 mM)
iv) 25 ml PDE4 enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazine-ethanesulfonic acid (HEPES)/0.1M naci, pH 8.5) is added to each tube on an ice bath. The contents of each tube are applied to an AFF-Gel 601 column (Biorad Laboratories, P.O. Box 1229, 85A Marcus Drive, Melvile, N.Y. 11747) (boronate affinity gel, 1 ml bed volume) previously equilibrated with washing buffer. [$^3$H]cAMP is washed with 2×6 ml washing buffer, and [$^3$H]5' AMP is then eluted with 4 ml of 0.25M acetic acid. After vortexing, 1 ml of the elution is added to 3 ml scintillation fluid in a suitable vial, vortexed and counted for [$^3$H].

$$\% \text{ inhibition} = 1 - \frac{\text{average cpm(test compound} - \text{average cmp(blank)}}{\text{average cpm(control)} - \text{average cpm(blank)}}$$

IC$_{50}$ is defined as that concentration of compound which inhibits 50% of specific hydrolysis of [$^3$H]cAMP to [$^3$H] 5'AMP.

The ability of the compounds I or the pharmaceutically acceptable salts thereof to inhibit the production TNF and, consequently, demonstrate their effectiveness for treating disease involving the production of TNF is shown by the following in vitro assay:

Peripheral blood (100 ml) from human volunteers is collected in ethylenediamine-tetraacetic acid (EDTA). Mononuclear cells are isolated by FICOLL/Hypaque and washed three times in incomplete HBSS. Cells are resuspended in a final concentration of 1×10$^6$ cells per ml in pre-warmed RPMI (containing 5% FCS, glutamine, pen/step and nystatin). Monocytes are plated as 1×10$^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 ml) are then added to the cells at 3–4 concentrations each and incubated for 1 hour. LPS (10 ml) is added to appropriate wells. Plates are incubated overnight (18 hrs) at 37° C. At the end of the incubation period TNF was analyzed by a sandwich ELISA (R&D Quantikine Kit). IC$_{50}$ determinations are made for each compound based on linear regression analysis.

The following Examples further illustrate the invention, but they are not intended to be, nor should they be taken as in any way a limitation of the present invention. In the following examples, "DMF" means dimethylformamide, "THF" means tetrahydrofuran, "DMSO" means dimethyl sulfoxide, and "DMAP" means 4-dimethylaminopyridine.

EXAMPLE 1

A. 3-Nitro4-propyl-benzoic acid 9.44 g (57.5 mmol, 1.0 equiv.) of 4-propylbenzoic acid were partially dissolved in 50 mL conc. H$_2$SO$_4$ and chilled in an ice bath. A solution of 4.7 mL (74.7 mmol, 1.3 equiv) conc. HNO$_3$ in 10 mL conc. H$_2$SO$_4$ was added dropwise over 1–2 min. After stirring 1 hour at 0° C., the reaction mixture was poured into a 1 L beaker half full with ice. After stirring 10 minutes, the white solid which formed was filtered, washed 1×H$_2$O, and dried to give 12.01 g (100%) of the title compound: mp 106–109° C.; IR (KBr) 3200–3400, 2966, 2875, 2667, 2554, 1706, 1618, 1537, 1299, 921 cm$^{-1}$; $^1$H NMR (300 MHz, DMSO-d$_6$) d 0.90 (t, 3H, J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz), $^{13}$C NMR (75.5 MHz, DMSO-d$_6$) d 14.2, 23.7, 34.2, 125.4, 130.5, 132.9, 133.6, 141.4, 149.5, 165.9; Anal. calcd for C$_{10}$H$_{11}$NO$_4$.¼H$_2$O: C, 56.20; H, 5.42; N, 6.55. Found: C, 56.12; H, 5.31; N, 6.81.

B. 3-Amino-4-propyl-benzoic acid

A mixture of 11.96 g (57.2 mmol) 3-nitro-4-propyl-benzoic acid and 1.5 g 10% Pd/C, 50% water wet, in 250 mL CH$_3$OH was placed on a Parr hydrogenation apparatus and shaken under 25 psi H$_2$ at ambient temperature. After 1 hour, the reaction mixture was filtered through celite, and the filtrate concentrated and dried to give 9.80 g (96%) of a pale yellow crystalline solid: mp 139.5–142.5° C.; IR (Kbr) 3200–2400, 3369, 3298, 2969, 2874, 2588, 1690, 1426, 916, 864 cm$^{-5}$; $^1$H NMR (300 Mhz, DMSO-d$_6$) d 0.90 (t, 3H, J=7.2 Hz), 1.52 (m, 2H), 2.42 (m, 2H), 5.08 (br s, 2H), 6.96 (d, 1H, J=7.8 Hz), 7.05 (dd, 1H, J=1.7, 7.8 Hz), 7.20 (d, 1H, J=1.7 Hz); MS (Cl, NH$_3$) m/z 180 (M+H$^+$, base); Anal. calcd for C$_{10}$H$_{13}$NO$_2$.⅓H$_2$O: C, 64:85; N, 7.89; N, 7.56. Found: C, 64.69; H, 7.49; N, 7.86.

C. 3-Carboxy-6-propyl-benzenediazo t-butyl sulfide

A mixture of 8.80 g (49.1 mmol, 1.0 equiv) 3-amino4-propyl-benzoic acid and 2.34 g (22.1 mmol, 0.45 equiv) sodium carbonate in 55 mL H$_2$O was heated gently with a heat gun until mostly dissolved. The reaction mixture was chilled in an ice bath, and a solution of 3.73 g (54.0 mmol, 1.0 equiv.) sodium nitrite in 27 mL H$_2$O was added dropwise. After 15 min., the reaction mixture was transferred to a dropping funnel and added over 10 minutes to a beaker containing 55 g of crushed ice and 10.6 mL concentrated HCl. After stirring 10 min., the contents of the beaker were transferred to a dropping funnel and added over 5 minutes to a room temperature solution of 5.31 mL (47.1 mmol, 0.96 equiv) t-butyl thiol in 130 mL ethanol. The pH was adjusted to 4–5 by addition of saturated aqueous Na$_2$CO$_3$ solution, and the reaction mixture was allowed to stir 1 hour at ambient temperature. 200 mL brine were added, and the mixture was filtered. The solid was washed 1×H$_2$O and dried overnight to give 12.25 g (89%) of a brown/rust colored powder (caution—stench): mp 102° C. (dec); IR (KBr) 3200–2400, 2962, 2872, 2550, 1678, 1484, 1428, 1298, 1171 cm$^{-1}$; $^1$H NMR (300 MHz, DMSO-d$_6$) d 0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1h, J=1.7, 7.9 Hz), 13.18 (br s, 1H); MS (thermospray, NH$_4$OAc) m/z 281 (M+H$^+$, base); Anal. calcd for C$_{14}$H$_{20}$N$_2$O$_2$S: C, 59.96; H, 7.19; N, 9.99. Found: C, 59.71; H, 7.32; N, 10.02.

D. 3-Ethyl-1H-indazole-6-carboxylic acid

A solution of 12.0 g (42.8 mmol, 1.0 equiv) 3-carboxy-6-propyl-benzenediazo t-butyl sulfide in 150 mL DMSO was added dropwise over 15 min. to a room temperature solution of 44.6 g (398 mmol, 9.3 equiv) potassium t-butoxide in 200 mL DMSO. After stirring 2 hours at ambient temperature, the reaction mixture was poured into 1.5 L of 0° C. $^1$N HCl, stirred 5 min., then extracted 2×350 mL ethyl acetate. The ethyl acetate extracts (caution—stench) were combined, washed 2×250 mL H$_2$O, and dried over MgSO$_4$. Filtration, concentration of filtrate and drying gave a tan solid, which was triturated with 1 L of 1:3 Et$_2$O/Hexanes and dried to give 7.08 g (87%) of a tan crystalline powder: mp 248–251° C.; IR (KBr) 3301, 3300–2400, 2973, 2504, 1702, 1455, 1401, 1219 cm$^{-1}$; $^1$H NMR (300 MHz, DMSO-d$_6$) d 1.31 (t, 3H, J=7.6 Hz), 2.94 (q, 2H, J=7.6 Hz), 7.63 (dd, 1H, J=1.1, 8.4 Hz), 7.81 (d, 1H, J=8.4 Hz), 8.06 (d, 1H, J=1.1 Hz) 12.95 (br s, 1H); MS (Cl, NH$_3$) m/z 191 (M+H$^+$, base); Anal. calcd for C$_{10}$H$_{10}$N$_2$O$_2$: C, 63.14; H, 5.30; N, 14.73. Found: C, 62.66; H, 5.42; N, 14.80.

E. 3-Ethyl-1H-indazole-6-carboxylic acid methyl ester 8.78 g (45.8 mmol, 1.1 equiv) 1-(3-dimethylaminopropyl)-3-ethylcarbodiimide hydrochloride were added in one portion to a room temperature solution of 7.92 g (41.6 mmol, 1.0 equiv) 3-ethyl-1H-indazole-6-carboxylic acid, 16.9 mL (416 mmol, 10 equiv) methanol and 5.59 g(45.8 mmol, 1.1 equiv) DMAP in 250 mL CH$_2$Cl$_2$. After 18 hours at room temperature, the reaction mixture was concentrated to 150 mL, diluted with 500 mL ethyl acetate, washed 2×100 mL 1N HCl, 1×100 mL H$_2$O, 1×100 mL brine, and dried over Na$_2$SO$_4$. Filtration, concentration of filtrate and drying gave 7.8 g of a brown solid, which was purified on a silica gel column (30% to 50% ethyl acetate/hexanes gradient) to give 6.41 g (75%) of a tan solid: mp 107–108° C.; IR (KBr) 3100–2950,1723, 1222 cm$^{-1}$; $^1$H NMR (300 MHz, CDCl$_3$) d 8.19 (m, 1H), 7.7–7.8 (m, 2H), 3.96 (s, 3H), 3.05 (q, 2H, J=7.7 Hz), 1.43 (t, 3H, 7.7 Hz); MS (Cl, NH$_3$) m/z 205 (M+H$^+$, base); Anal. calcd for C$_{11}$H$_{12}$N$_2$O$_2$: C, 64.70; H, 5.92; N, 13.72. Found: C, 64.88; H, 6.01; N, 13.96.

F. 1-Cyclopentyl-3-ethyl-1H-indazole-6-carboxylic acid methyl ester 1.17 g (29.4 mmol, 1.05 equiv) sodium hydride, 60% oil dispersion, was added in one portion to a room temperature solution of 5.7 g (27.9 mmol, 1.0 equiv) 3-ethyl-1H-indazole-6-carboxylic acid methyl ester in 125 mL anhydrous DMF. After 20 minutes, 3.89 mL (36.6 mmol, 1.3 equiv)cyclopentyl bromide were added dropwise, and the reaction was mixture allowed to stir overnight at room temperature. The mixture was then poured into 1 L H$_2$O and extracted 3×450 mL ethyl acetate. The organic extracts were combined, washed 3×400 mL H$_2$O, 1×200 mL brine, and dried over Na$_2$SO$_4$. Filtration, concentration of filtrate and drying gave an amber oil, which was purified on a silica gel column (10% ethyl acetate/hexanes, gravity) to give 5.48 g (72%) of a clear oil: $^1$H NMR (300 MHz, CDCl$_3$) d 8.16 (d, 1H, J=1.0 Hz), 7.7 (m, 2H), 5.00 (quintet, 1H, J=7.5 Hz), 3.97 (s, 3H), 3.01 (q, 2H, J=7.6 Hz), 2.2 (m, 4H), 2.0 (m, 2H), 1.8 (m, 2H), 1.39 (t, 3H, J=7.6 Hz); HRMS calcd for C$_{16}$H$_{20}$N$_2$O$_2$; 272.1526. Found: 272.15078.

G. (1-Cyclopentyl-3-ethyl-i H-indazol6-yl)-methanol 7 mL (7.0 mmol, 1.0 equiv) lithium aluminum hydride, 1.0 M solution in THF, were added to a 0° C. solution of 1.02 g (7.05 mmol, 1.0 equiv) 1-cyclopentyl-3-ethyl-1H-indazole-6-carboxylic acid methyl ester in 50 mL anhydrous THF. After 20 minutes, 1 mL methanol was added cautiously, then the reaction mixture was poured into 500 mL of 5% H$_2$SO$_4$ and extracted 3×50 mL ethyl acetate. The organic extracts were combined, washed 2×40 mL H$_2$O, 1×40 mL brine, and dried over Na$_2$SO$_4$. Filtration, concentration of filtrate, and drying gave 1.58 g of a clear oil, which was purified on a silica gel column to give 1.53 g (89%) clear oil: IR (CHCl$_3$) 3606, 3411, 3009, 2972, 2875,1621, 1490 cm$^{-1}$; $^1$H NMR (300 Mhz, CDCl$_3$) d 7.65 (d, 1H, J=8.0 Hz), 7.42 (s, 1H), 7.06 (dd, 1H, J=1.0, 8.2 Hz), 4.92 (quintet, 1H, J=7.7 Hz), 4.84 (s, 2h), 2.98 (q, 2H, J=7.6 Hz), 2.2 (m, 4H), 2.0 (m, 2H), 1.7 (m, 3H), 1.38 (t, 3H, J=7.6 Hz); MS (thermospray, NH$_4$OAc) m/z 245 (M+H+, base); HRMS calcd for C$_{15}$H$_{20}$N$_2$O+H: 245.1654. Found: 245.1675.

H. 1-Cyclopentyl-3-ethyl-1H-indazole-6-carbaldehyde 06 mg (0.301 mmol, 0.05 equiv) tetrapropylammonium perruthenate (VII) were added to a room temperature suspension of 1.47 g (6.02 mmol, 1.0 equiv) (1-cyclopentyl-3-ethyl-1H-indazol-6-yl)-methanol, 1.06 g (9.03 mmol, 1.5 equiv) N-methylmorpholine N-oxide and 3.01 g 4A molecular sieves in 12 mL anhydrous CH$_2$Cl$_2$. After 30 minutes, the reaction mixture was filtered through a short column of silica gel (eluted with CH$_2$Cl$_2$). Fractions containing product were concentrated, and the residue chromatographed on a silica gel column (15% ethyl acetate/hexanes, flash) to give 924 mg (63%) of a pale yellow solid: mp 41° C.; IR (KBr) 3053, 2966, 2872, 2819, 1695 cm$^{-1}$; $^1$H NMR (300 MHz, CDCl$_3$) d 10.13 (s, 1H), 7.93 (d, 1H, J=0.9 Hz), 7.77 (d, 1H, J=8.4 Hz), 7.60 (dd, 1H, J=1.2, 8.4 Hz), 5.00 (quintet, 1H, J=7.5 Hz), 3.01 (q, 2H, J=7.6 Hz), 2.2 (m, 4H), 2.0 (m, 2H), 1.7 (m, 2H), 1.39 (t, 3H, J=7.5 Hz); MS (Cl, NH$_3$) m/z 243 (M+H$^+$, base); Anal. calcd for C$_{15}$H$_{18}$N$_2$O: C, 74.35; H, 7.49; N, 11.56. Found: C, 74.17; H, 7.58; N, 11.79.

EXAMPLE 2

A. 4-Bromo-2-nitro-1-propyl-benzene 125 g (628 mmol, 1.0 equiv) 1-bromo4-propyl-benzene were added in one portion to a 10° C. solution of 600 mL concentrated H$_2$SO$_4$ and 200 mL H$_2$0. With vigorous mechanical stirring, a room temperature mixture of 43.2 mL (691 mmol, 1.1 equiv) conc. HNO$_3$ (69–71%, 16M) in 150 mL conc. H$_2$SO$_4$ and 50 mL H$_2$O was added dropwise over 30 minutes. The ice bath was allowed to warm to room temperature, and the reaction stirred at room temperature for 68 hours. The reaction mixture was poured into a 4 L beaker, loosely packed full with crushed ice. After stirring 1 hour, the mixture was transferred to a 4 L separatory funnel and extracted 4×800 mL isopropyl ether. The organic extracts were combined, washed 3×800 mL H$_2$O, 1×500 mL brine, and dried over Na$_2$SO$_4$. Filtration, concentration of filtrate and drying gave 150 mL of a yellow liquid, which was purified by silica gel chromatography (2 columns, 3 kg silica gel each, 2% ethyl acetate/hexanes) to afford 63.9 g (42%) of a yellow liquid. The desired regioisomer is the less polar of the two, which are formed in a 1:1 ratio. bp 108° C., 2.0 mm; IR (CHCl$_3$) 3031, 2966, 2935, 2875, 1531, 1352 cm$^{-1}$; $^1$H NMR (300 MHZ, CDCl$_3$) d 8.01 (d, 1H, J=2.1Hz), 7.62 (dd, 1H, J=2.1, 8.3 Hz), 7.23 (d, 1H, J=8.3 Hz), 2.81 (m, 2H), 1.67 (m, 2H), 0.98 (t, 3H, J=7.4 Hz); $^{13}$C NMR (75.5 MHz, CDCl$_3$) d 13.94, 23.74, 34.43, 119.6, 127.4, 133.3, 135.7, 136.4, 149.8; GCMS (El) m/z 245/243 (M$^+$.), 147 (base); HRMS calcd for C$_9$H$_{10}$NO$_2$BR+H: 243.9973. Found: 243.9954.

B. 5-Bromo-2-propyl-phenylamine 121 g (639 mmol, 3.0 equiv) of stannous chloride (anhydrous) were added in one portion to a room temperature solution of 51.9 g (213 mmol, 1.0 equiv) 4-bromo-2-nitro-1-propyl-benzene in 1200 mL absolute ethanol and 12 mL (6 equiv) H$_2$O. After 24 hours at room temperature, most of the ethanol was removed on a rotary evaporator. The residue was poured into a 4 L beaker, three-quarters full with crushed ice and H$_2$O. 50 9 of NaOH pellets were added portionwise, with stirring, until the pH=10 and most of the tin hydroxide has dissolved. The mixture was divided in half, and each half extracted 2×750 mL ethyl acetate. All four ethyl acetate extracts were combined, washed 1×500 mL each 1N NaOH, $H_2O$, and brine, then dried over $Na_2SO_4$. Filtration, concentration of filtrate and drying gave a yellow liquid, which was purified on a 1.2 kg silica gel column (1:12 ethyl acetate/hexanes) to give 41.83 g (92%) of a pale yellow liquid: IR (CHCl$_3$) 3490, 3404, 3008, 2962, 2933, 2873, 1620, 1491 cm$^{-1}$; $^1$H NMR (300 MHz, CDCl$_3$) d 6.8–6.9 (m, 3H), 3.90 br s, 2H), 2.42 (m, 2H0, 1.62 (m, 2H), 0.99 (t, 3H, J=7.3 Hz); GCMS (EI) m/z 215/213 (M$^+$.), 186/184 (base); Anal. calcd for $C_9H_{12}NBr$: C, 50.49; H, 5.65; N, 6.54 Found: C, 50.77; H, 5.70; N, 6.50.

C. 6-Bromo-3-ethyl-1H-indazole 49.22 g (230 mmol, 1.0 equiv) 5-bromo-2-propyl-phenylamine were placed in a 3 L flask and chilled in an ice bath. A 0° C. solution of 57.5 mL (690 mmol, 3.0 equiv) conc. HCl in 165 mL $H_2O$ was added, and the resulting solid mass which formed was ground up until a fine white suspension resulted. 100 mL more $H_2O$ were added, then a solution of 15.9 g (230 mmol, 1.0 equiv) sodium nitrite in 75 mL $H_2O$ was added dropwise over 10 min. The ice bath was removed, and the reaction allowed to stir at room temperature for 30 minutes. The reaction mixture was then filtered through a sintered glass funnel, precooled to 0° C. The filtrate was chilled in an ice bath, and with mechanical stirring, a 0° C. solution/suspension of 32.8 g (313 mmol, 1.36 equiv) ammonium tetrafluoroborate in 110 mL $H_2O$ was added dropwise over 10 min. The thick white suspension which formed (aryl diazonium tetrafluoroborate salt) was allowed to stir 1.5 hours at 0° C. The mixture was then filtered, and the solid washed 1×200 mL 5% aq. $NH_4BF_4$ (cooled to 0° C.), 1×150 mL $CH_3OH$ (cooled to 0° C.), then 1×200 mL $Et_2O$. Drying at high vacuum, room temperature for 1 hour gave 54.47 g (76%) of the diazonium salt, an off-white solid.

1500 mL of ethanol free chloroform was placed in a 3 L flask, then 34.16 g (348 mmol, 2.0 equiv) potassium acetate (powdered and dried) and 2.3 g (8.7 mmol, 0.05 equiv) 18-crown-6 were added. After 10 minutes the diazonium salt was added in one portion, and the reaction mixture allowed to stir at room temperature under nitrogen atmosphere for 18 hours. The mixture was then filtered, the solid washed 2× with CHCl$_3$, and the filtrate concentrated to give 47 g of crude product (brown crystals). Silica gel chromatography (1.23 kg silica gel, ethyl acetate/hexanes gradient 15%, 20%, 40%) gave 21.6 g (55% for second step, 42% overall) of tan crystals: mp 112–114° C.; IR (KBr) 3205, 3008, 2969, 2925, 1616, 1340, 1037 cm$^{-1}$; $^1$H NMR (300 MHz, CDCl$_3$) d 9.86 (br s, 1H), 7.61 (d, 1H, J=1.3 Hz), 7.57 (d, 1H. J=8.4 Hz), 7.24 (dd, 1H, J=1.5, 8.6 Hz), 2.99 (q, 2H, J=7.6 Hz), 1.41 (t, 3H, J=7.6 Hz); MS (Cl, NH$_3$) m/z 227/225 (M+H$^+$, base); Anal. calcd for $C_9H_9N_2Br$: C, 48.02; H, 4.03; N, 12.45. Found: C, 48.08; H, 3.87; N, 12.45.

D. 6-Bromo-1-cyclopentyl-3-ethyl-1H-indazole 2.46 g (61.4 mmol, 1.05 equiv) sodium hydride, 60% oil dispersion, was added in 0.5 g portions to a 10° C. solution of 13.17 g (58.5 mmol, 1.0 equiv) 6-bromo-3-ethyl-1H-indazole in 500 mL anhydrous DMF. The mixture was stirred at room temperature for 20 minutes, then a solution of 8.8 mL (81.9 mmol, 1.4 equiv)cyclopentyl bromide in 10 mL anhydrous DMF was added dropwise. After 18 hours, the reaction mixture was poured into 2 L $H_2O$ and extracted 2×1L ethyl acetate. The organic extracts were combined, washed 2×750 mL $H_2O$, 1×500 mL brine, and dried over $Na_2SO_4$. Filtration, concentration of filtrate and drying gave 20.7 g of crude product, which was purified on a silica gel column (1.1 kg silica gel, 3% ethyl acetate/hexanes) to give 10.6 g (62%) of an amber liquid: IR (CHCl$_3$)2972, 2875, 1606, 1501, 1048 cm$^{-1}$; $^1$H NMR (300 MHz, CDCl$_3$) d 7.56 (d, 1H, J=1.3 Hz), 7.52 (d, 1H, J=8.7 Hz), 7.17 (dd, 1H, J=1.5, 8.5 Hz), 4.83 (quintet, 1H, J=7.6 Hz), 2.96 (q, 2H, J=7.6 Hz), 2.15 (m, 4H), 2.0 (m, 2H), 1.65 (m, 2H), 1.36 (t, 3H, J =7.7 Hz); MS (thermospray, NH$_4$OAc) m/z 295/293 (M+H$^+$, base); Anal. calcd for $C_{14}H_{17}N_2Br$: C, 57:35; H, 5.84; N, 9.55. Found: C, 57.48; H, 5.83; N, 9.90.

E. (1-Cyclopentyl-3-ethyl-1H-indazole)-6-carbaldehyde 11.6 mL (28.4 mmol, 1.0 equiv) n-BuLi, 2.45 M in hexanes, were added to a –78° C. solution of 8.32 g (28.4 mmol, 1.0 equiv) 6-bromo-1-cyclopentyl-3-ethyl-1H-indazole in 200 mL anhydrous THF. After 30 min. at –78° C., 8.8 mL (114 mmol, 4.0 equiv) anhydrous DMF was added dropwise, and the reaction mixture was allowed to stir an additional 30 min. at –78° C. The mixture was warmed to room temperature over 1 hour, then 125 mL 1N HCl was added. After stirring for 10 minutes, most of the THF was removed on a rotary evaporator. The residue was diluted with 500 mL $H_2O$, and extracted 2×250 mL ethyl acetate. The organic extracts were combined, washed 1×100 mL $H_2O$, 1×100 mL brine, and dried over $Na_2SO_4$. Filtration, concentration of filtrate and drying gave a yellow oil, which was purified on a silica gel column (15% ethyl acetate/hexanes, gravity) to give 4.70 g (68%) of a yellow crystalline solid: $^1$H NMR (300 MHz, CDCl$_3$) identical to the spectrum of the compound from example 8.

F. (1-Cyclopentyl-3-ethyl-1H-indazol-6-yl)-acetonitrile 4.44 mL (35.0 mmol, 1.5 equiv) trimethylsilyl chloride were added dropwise to a room temperature suspension of 5.65 g (23.3 mmol, 1.0 equiv) 1-cyclopentyl-3-ethyl-1H-indazole-6-carbaldehyde and 3.84 g (44.3 mmol, 1.9 equiv) lithium bromide in 115 mL anhydrous acetonitrile. After 15 minutes, the reaction mixture was cooled in an ice bath, and 6.84 mL (38.7 mmol, 1.66 equiv) 1,1,3,3-tetramethyidisiloxane were added dropwise, and the reaction was allowed to warm to room temperature over 2 hours. The reaction mixture was heated to reflux for 6 hours, then cooled to room temperature, diluted with 300 mL $CH_2Cl_2$, and filtered through Celite®. The filtrate was concentrated and dried at high vacuum, room temperature to give 13.08 g of a tan oily solid.

This solid was dissolved in 200 mL anhydrous DMF, 259 g (52.9 mmol, 2.27 equiv) sodium cyanide were added, and the mixture stirred at room temperature for 2 hours. The reaction mixture was then poured into 500 mL $H_2O$ and extracted 3×200 mL ethyl acetate. The organic extracts were combined, washed 3×200 mL $H_2O$, 1×200 mL brine, and dried over $Na_2SO_4$. Filtration, concentration of filtrate and drying gave a brown oil, which was purified on a silica gel column (10%-20% ethyl acetate/hexanes gradient) to give 2.98 g of impure product and 2.05 g of recovered (impure) starting material.

The recovered starting material was resubjected to the reaction conditions described above, using 50 mL 1,1,3,3-tetramethyldisiloxane, followed by 50 mL DMF and 940 mg sodium cyanide. Silica gel chromatography gave 0.62 g of impure product, which was then combined with the 2.98 g lot of impure product and rechromatographed (10% ethyl acetate/hexanes) to give 3.27 g (55%) of a yellow oil: IR (CHCl$_3$) 3062, 2972, 2874, 2255, 1623 cm$^{-1}$; $^1$H NMR (300 MHz, CDCl$_3$) d 7.66 (d, 1H, J=8.3 Hz), 7.39 (s, 1H), 6.97 (dd, 1H, J=1.1, 8.4 Hz), 4.90 (quintet, 1H, J=7.6 Hz), 3.89 (s, 2H), 2.98 (q, 2H, J=7.6 Hz), 2.2 (m, 4H), 2.0 (m, 2H), 1.7 (m, 2H), 1.37 9t, 3H, J=7.4 Hz); MS (Cl, NH$_3$) m/z 254

(M+H⁺, base); Anal. calcd. for $C_{16}H_{19}N_3$: C, 75.86; H, 7.56; N, 16.59. Found: C, 75.84; H, 7.94; N, 16.60.

G. 4-Cyano-4-(1-cyclopentyl-3-ethyl-1H-indazol-6-yl)-heptanedioic acid dimethyl ester 530 mL (1.26 mmol, 0.1 equiv) triton B, 40% in methanol, was added to a room temperature solution of 3.19 g (12.6 mmol, 1.0 equiv) (1-cyclopentyl-3-ethyl-1H-indazol-6-yl)-acetonitrile in 100 mL anhydrous acetonitrile. The reaction mixture was heated to reflux, and 11.3 mL (126 mmol, 10.0 equiv) methyl acrylate was added dropwise. After 15 minutes, the reaction mixture was cooled to room temperature, and concentrated on a rotary evaporator. The residue was diluted with 300 mL ether, washed 1×50 mL 1N HCl, 1×50 mL brine, and dried over $Na_2SO_4$. Filtration, concentration of filtrate and drying gave a brown oil, which was purified on a silica gel column (20% ethyl acetate/hexanes, flash) to give 4.00 g (75%) of a yellow oil: IR ($CHCl_3$) 3031, 2972, 2955, 2874, 2250, 1735 cm⁻¹; ¹H NMR (300 MHz, $CDCl_3$) d 7.68 (d, 1H, J=8.5 Hz), 7.49 (s, 1H), 6.97 (d, 1H, J=8.5 Hz); 4.93 (quintet, 1H, J=7.6 Hz), 3.58 (s, 6H), 2.97 (q, 2H), J=7.7 Hz), 2.45 (m, 6H), 2.2 (m, 6H), 2.0 (m, 2H), 1.8 m, 2H), 1.37 (t, 3H, J=7.7 Hz); MS (Cl, $NH_3$) m/z 426 (M+H⁺, base); Anal. calcd for $C_{24}H_{31}N_3O_4$: C, 67.74; H, 7.34; N, 9.88. Found: C, 67.76; H, 7.40; N, 10.08.

H. (±)-5-Cyano-5-(1-cyclopentyl-3-ethyl-1H-indazol-6-yl)-2-oxo-cyclohexane-carboxylic acid methyl ester 924 mg (23.1 mmol, 2.5 equiv) sodium hydride, 60% oil dispersion, was added in one portion to a room temperature solution of 3.93 g (9.24 mmol, 1.0 equiv) 4-cyano-4-(1-cyclopentyl-3-ethyl-1H-indazol-6-yl)-heptanedioic acid dimethyl ester in 100 mL anhydrous 1,2-dimethoxyethane. The reaction mixture was heated to reflux under nitrogen atmosphere for 1.5 hours, then cooled to room temperature. After 18 hours, the reaction mixture was quenched with 50 mL $H_2O$, poured into 200 mL ethyl acetate, and washed 1×100 mL 1N HCl. The aqueous layer was extracted 1×50 mL ethyl acetate. The organic extracts were combined, washed 1×50 mL brine, and dried over $Na_2SO_4$. Filtration, concentration of filtrate and drying gave a yellow oil, which was purified on a silica gel column (10% ethyl acetate/hexanes) to give 2.78 g (76%) of a white amorphous solid: IR (KRr) 2954, 2871, 2240, 1663, 1619 cm⁻¹; ¹H NMR (300 MHz, $CDCl_3$) d 12.27 (s, 1H), 7.70 (d, 1H, J=8.5 Hz), 7.57 (s, 1H), 7.15 (dd, 1H, J=1.6, 8.5 Hz), 4.93 (quintet, 1H, J=7.6 Hz), 3.78 (s, 3H), 3.05 (m, 1H), 2.98 (q, 2H, J=7.6 Hz), 2.9 (m, 1H), 2.75 (m, 1H), 2.6 (m, 1H), 2.35 (m, 2H), 2.2 (m, 4H), 2.0 (m, 2H), 1.75 (m, 2H), 1.38 (t, 3H, J=7.6 Hz); MS (Cl, $NH_3$) m/z 394 (M+H⁺, base); Anal. calcd for $C_{23}H_{27}N_3O_3$: C, 70.22; H, 6.92; N, 10.68. Found: C, 70.07; H, 7.01; N, 10.70.

I. 1-(1-Cyclopentyl-3-ethyl-1H-indazol-6-yl)-4-oxo-cyclohexanecarbonitrile

A mixture of 2.72 g (6.91 mmol, 1.0 equiv) (±)-5-cyano-5-(1-cyclopentyl-3-ethyl-1H-indazol-6-yl)-2-oxo-cyclohexanecarboxylic acid methyl ester and 2.58 g (44.2 mmol, 6.4 eqiv) sodium chloride in 50 mL dimethyl sulfoxide and 4 mL $H_2O$ was heated in 140° C. oil bath under nitrogen atmosphere. After 3 hours, the reaction mixture was cooled to room temperature and allowed to stir for 72 hours. The reaction mixture was poured into 250 mL $H_2O$ and extracted 2×150 mL ethyl acetate. The organic extracts were combined, washed 2×100 mL $H_2O$, 1×100 mL brine, and dried over $Na_2SO_4$. The crude product was purified on a silica gel column (20% ethyl acetate/hexanes) to give 1.82 g (78%) of a white crystalline solid: mp 81–89° C.; IR (KBr) 2969, 2951, 2872, 2236, 1716 cm⁻¹; ¹H NMR (300 MHz, $CDCl_3$) d 7.71 (d,1H, J=8.5 Hz), 7.58 (s, 1H), 7.16 (dd, 1H, J=1.5, 8.5 Hz), 4.93 (quintet, 1H, J=7.6 Hz), 3.0 (m, 4H), 2.7 (m, 4H), 2.45 (m, 2H), $NH_4OAc$) m/z 336 (M+H⁺, base); Anal. calcd for $C_{21}H_{25}N_3O$: C, 75.20; H, 7.51; N, 12.53. Found: C, 74.06; H, 7.59; N, 12.41; HRMS calcd for $C_{21}H_{25}N_3O+H$: 336.20778. Found 336.2088.

EXAMPLE 3

A. 1-(1-Cyclopentyl-3-ethyl-1H-indazol-6-yl)-4-[1,3]dithian-2-ylidene-cyclohexane-carbonitrile 3.94 mL (9.84 mmol, 2.09 equiv) n-BuLi, 2.5 M in hexanes, was added dropwise to a 0° C. solution of 1.88 mL (9.89 mmol, 2.1 equiv) 2-trimethylsilyl-1,3-dithiane in 80 mL anhydrous THF. After 25 minutes at 0C, the reaction mixture was cooled to −78° C. and a solution of 1.58 g (4.71 mmol, 1.0 equiv) 1-(1-cyclopentyl-3-ethyl-1H-indazol-6-yl)-4-oxo-cyclohexanecarbonitrile in 40 mL anhydrous THF was added. After 1 hours at −78° C., the reaction mixture was quenched by addition of 50 mL brine, then warmed to room temperature, diluted with 100 mL $H_2O$, and extracted 1×100 mL $CH_2Cl_2$ and 1×50 mL brine, and dried over $Na_2SO_4$. Filtration, concentration of filtrate and drying gave a clear oil, which was purified on a silica gel column (10% ethyl acetate/hexanes) to give 1.51 g (73%) of a white amorphous solid: IR (KBr) 2962, 2870, 2232, 1620, 1569, 1508, 1434, 1217 cm⁻¹; ¹H NMR (300 MHz, $CDCl_3$) d 7.67 (d, 1H, J=8.5 Hz), 7.53 (s, 1H), 7.15 (dd, 1H, J=1.5, 8.6 Hz), 4.92 (quintet, 1H, J=7.6 Hz), 3.36 (m, 2H), 3.0 (m, 6H), 2.42 (m, 2H), 2.34 (m, 2H), 2.2 (m, 6H), 2.0 (m, 4H), 1.8 (m, 2H), 1.37 (t, 3H, J=7.5 Hz); MS (Cl, $NH_3$) m/z 438 (M+H⁺, base); Anal. calcd for $C_{25}H_{31}N_3S_2$: C, 68.60; H, 7.14; N, 9.60. Found: C, 68.26; H, 7.29; N, 9.58.

B. Trans-4-cyano-4-(1-cyclopentyl-3-ethyl-1H-indazol-6-yl)cyclohexanecarboxylic acid methyl ester and Cis-4-cyano-4-(1-cyclopentyl-3-ethyl-1H-indazol-6-yl)cyclohexanecarboxylic acid methyl ester A mixture of 1.45 g (3.31 mmol, 1.0 equiv) 1-(1-cyclopentyl-3-ethyl-1H-indazol-6-yl)-4-[1,3]dithian-2-ylidenecyclohexane-carbonitrile, 3.59 g (13.2 mmol, 4.0 equiv) mercury (II) chloride and 1.48 mL (16.9 mmol, 5.1 equiv) 70% perchloric acid in 60 mL methanol was heated to reflux under nitrogen atmosphere. After 2 hours, the reaction mixture was cooled to room temperature, diluted with 250 mL $CH_2Cl_2$ and filtered through Celite®. The filtrate was washed 1×100 mL saturated aqueous $NaHCO_3$, 1×75 mL 10% aqueous sodium sulfite, 1×100 mL $H_2O$, and dried over $Na_2SO_4$. Filtration, concentration of filtrate and drying gave a clear oil, which was purified on a silica gel column (15% ethyl acetate/hexanes) to give 340 mg (27%) of trans isomer (less polar) as a white solid, and 794 mg (63%) of cis isomer (more polar) as a white solid:

data for trans isomer: mp 79–82° C.; IR (KBr) 2973, 2949, 2890, 2871, 2235, 1721, 1618, 1484, 1453, 1217, 1170 cm⁻¹; ¹H NMR (300 MHz, $CDCl_3$) d 7.67 (d, 1H, J=8.4 Hz), 7.52 (s, 1Y), 7.14 (dd, 1H, J=1.4, 8.5 Hz), 4.93 (quintet, 1H, J=7.6 Hz), 3.74 (s, 3H), 2.97 (q, 2H, J=7.6 Hz), 2.85 (m 1HO, 2.3 (m, 2H), 2.2 (m, 10H), 2.0 (m, 2H), 1.75 (m, 2H), 1.37 (t, 3H, J=7.6 Hz); MS (Cl, $NH_3$) m/z 380 (M+H⁺, base); Anal. calcd for $C_{23}H_{29}N_3O_2$: C, 72.79; H, 7.70; N, 11.07. Found: C, 73.05; H, 7.80; N, 11.03.

data for cis isomer: mp 112–114° C.; IR (KBr) 3065, 2952, 2866, 2234, 1731, 1622, 1487, 1445, 1220, 1204 cm⁻¹; ¹H NMR (300 MHz, $CDCl_3$) d 7.68 (d, 1H, J=8.5 Hz), 7.55 (s, 1H), 7.14 (dd, 1H, J=1.3, 8.4 Hz), 4.93 (quintet, 1H, J=7.6 Hz), 3.73 (s, 3H), 2.98 (q, 2H, J=7.6 Hz ), 2.42 (m, 1H), 2.36 (m, 1H), 1.9–2.3 (m, 13H), 1.8 (m, 2H), 1.37 (t, 3H, J=7.5 Hz); MS (Cl, $NH_3$) m/z 380 (M+H⁺, base); Anal. calcd for $C_{23}H_{29}N_3O_2$: C, 72.79; H, 7.70; N, 11.07. Found: C, 72.93; H, 7.56; N, 10.92.

EXAMPLE 4
Trans-4-cyano-4-(1-cyclopentyl-3-ethyl-1H-indazol-6-yl)-cyclohexanecarboxylic acid A mixture of 337 mg (0.888 mmol, 1.0 equiv) trans-4-cyano-4-(1-cyclopentyl-3-ethyl-1H-indazol-6-yl)-cyclohexanecarboxylic acid methyl ester in 10 mL methanol, 2 mL THF and 2.7 mL (2.66 mmol, 3.0 equiv) 1N NaOH was allowed to stir at room temperature. After 3 hours, the reaction mixture was concentrated on a rotary evaporator, diluted with 100 mL $H_2O$, acidified to pH 1, and extracted 2×70 mL ethyl acetate. The organic extracts were combined, washed 1×50 mL $H_2O$, 1×50 mL brine, and dried over $Na_2SO_4$. Filtration, concentration and drying gave a white solid, which was purified on a silica gel column (5% $CH_3OH/CH_2Cl_2$) to give 197 mg (61%) of a white amorphous solid: IR (KBr) 3200–2500, 3060, 2963, 2871, 2245, 1729, 1702, 1621, 1453, 1219 $cm^{-1}$; $^1H$ NMR (300 MHz, DMSO-$_6$) d 12.4 (br s, 1H), 7.77 (d, 1H, J=8.5 Hz), 7.69 (s, 1H), 7.20 (dd, 1H, J=1.3, 8.5 Hz), 5.17 (quintet, 1H, J=7.6 Hz), 2.90 (q, 2H, J=7.6 Hz), 2.75 (m, 1H), 1.9–2.3 (m, 16H), 1.7 (m, 2H), 1.28 (t, 3H, J=7.6 Hz); MS (Cl, $NH_3$) m/z 366 (M+H$^+$, base); Anal. calcd for $C_{22}H_{27}N_3O_2$: C, 72.29; H, 7.45; N, 11.50. Found: C, 71.98; H, 7.75; N, 11.21.

EXAMPLE 5
Cis-4-cyano-4-(1-cyclopentyl-3-ethyl-1H-indazol-6-yl)-cyclohexanecarboxylic acid A mixture of 831 mg (2.19 mmol, 1.0 equiv) cis-4-cyano-4-(1-cyclopentyl-3-ethyl-1H-indazol-6-yl)-cyclohexanecarboxylic acid methyl ester in 20 mL methanol, 4 mL THF and 6.6 mL (6.57 mmol, 3.0 equiv) 1N NaOH was allowed to stir at room temperature. After 1.5 hours, the reaction mixture was concentrated on a rotary evaporator, diluted with 100 mL $H_2O$, acidified to pH 1, and extracted 2×70 mL ethyl acetate. The organic extracts were combined, washed 1×50 mL $H_2O$, 1×50 mL brine, and dried over $Na_2SO_4$. Filtration, concentration and drying gave 0.80 g of a white solid, which was purified on a silica gel column (5% $CH_3OH/CH_2Cl_2$) to give 730 mg (91%) of a white crystalline solid. Recrystallization from ethyl acetate/hexanes gave 538 mg of white crystals: mp 197–199° C.; IR (KBr) 3200–2600, 3061, 2961, 2948, 2939, 2871, 2245, 1732, 1625, 1451, 1255, 1185, 1169 $cm^{-1}$; $^1H$ NMR (300 MHz, DMSO-$d_6$) d 12.35 (brs, 1H), 7.77 (d, 1H, J=8.6 Hz), 7.73 (s, 1HO, 7.27 (dd, 1H, J=1.5, 8.5 Hz), 5.13 (quintet, 1H, J=7.5 Hz), 2.90 (q, 2H, J=7.6 Hz), 2.42 (m, 1H), 2.30 (m, 2H), 1.7–2.1 (m, 14H), 1.29 (t, 3H, J=7.5 Hz); MS (Cl, $NH_3$) m/z 366 (M+H$^+$, base); Anal. calcd for $C_{22}H_{27}N_3O_2$: C, 72.29; H, 7.45; N, 11.50. Found: C, 72.01; H, 7.60; N, 11.29.

EXAMPLE 6
A. 6-Bromo-1-cyclohex-2-enyl-3-ethyl-1H-indazole 2.12 g (52.9 mmol, 1.05 equiv) sodium hydride, 60% oil dispersion, was added in four portions over 10 min. to a room temperature solution of 11.35 g (50.4 mmol, 1.0 equiv) 6-bromo-ethyl-1H-indazole in 300 mL anhydrous DMF. After stirring 20 min., 9.0 mL (70.6 mmol, 1.4 equiv) 3-bromo-cyclohexene were added dropwise, and the reaction concentrated and dried at high vacuum, room temperature to give 7.52 g of an orange/yellow solid.

This solid was dissolved in anhydrous DMF, 1.56 g (31.8 mmol, 2.27 equiv) sodium cyanide were added, and the mixture stirred at room temperature for 2.5 h. The reaction mixture was then poured into 400 mL $H_2O$ and extracted 3×200 mL ethyl acetate. The organic extracts were combined, washed 3×150 mL $H_2O$, 1×150 mL brine, and dried over $Na_2SO_4$. Filtration, concentration of filtrate and drying gave a yellow oil, which was purified on a silica gel column (5%–10% ethyl acetate/hexanes gradient) to give 1.40 g (38%) of a yellow/green oil; MS (Cl, $NH_3$) 268 (M+H$^+$, base); Anal. calcd for $C_{17}H_{21}N_3$: C, 76.38; H, 7.92; N, 15.72. Found C, 76.43; H, 7.53; N, 15.39.

B. 6-Bromo-1-cyclohexyl-3-ethyl-1H-indazole

A mixture of 10.22 g (33.5 mmol, 1.0 equiv) 6-bromo-1-cyclohex-2-enyl-3-ethyl-1H-indazole and 1.5 g 10% Pt/C in 1 L cyclohexane was placed on a Parr® hydrogenation apparatus and shaken under 2–5 psi $H_2$ at room temperature. After 1 h, the reaction mixture was filtered through celite®, and the filtrate concentrated on a rotary evaporator and chromatographed (5% ethyl acetate/hexanes, flash) to give 9.70 g (94%) of a pale yellow oil: MS (Cl, $NH_3$) m/z 309/307 (M+H$^+$, base); Anal. calcd for $C_{15}H_{19}N_2Br$: C, 58.64; H, 6.23; N, 9.12. Found: C, 58.56; H, 6.29; N, 8.77.

C. 1-Cyclohexyl-3-ethyl-1H-indazole-6-carbaldehyde

This compound was prepared according to the method of example 2.E., using 5.02 g (16.3 mmol, 1.0 equiv) 6-bromo-1-cyclohexyl-3-ethyl-1H-indazole as starting material to give 3.65 g (87%) of a pale yellow oil: MS (Cl, $NH_3$) m/z 257 (M+H$^+$, base); Anal. calcd for $C_{16}H_{20}N_2O$: C, 74.97; H, 7.87; N, 10.93. Found: C, 75.00; H, 7.70; N, 10.74.

D. (1-(Cyclohexyl-3-ethyl-1H-indazol-4-yl)-acetonitrile 2.7 mL (21.0 mmol, 1.5 equiv) trimethylsilyl chloride were added dropwise to a room temperature suspension of 3.58 g (14.0 mmol, 1.0 equiv) 1-cyclohexyl-3-ethyl-1H-indazole-6-carbaldehyde and 2.31 g (26.6 mmol, 1.9 equiv) lithium bromide in 100 mL anhydrous acetonitrile. After 15 min., the reaction mixture was cooled in an ice bath, and 4.1 mL (23.2 mmol, 1.66 equiv) 1,1,3,3-tetramethyldisiloxane were added dropwise, and the reaction was allowed to warm to room temperature over 30 min. The reaction mixture was heated to reflux for 3 h, then cooled to room temperature, diluted with 300 mL $CH_2Cl_2$, and filtered through Celite®. The filtrate was concentrated and dried at high vacuum, room temperature to give 7.52 g of an orange/yellow solid.

This solid was dissolved in 100 mL anhydrous DMF, 1.56 g (31.8 mmol, 2.27 equiv) sodium cyanide were added, and the mixture stirred at room temperature for 2.5 h. The reaction mixture was then poured into 400 mL $H_2O$ and extracted 3×200 mL ethyl acetate. The organic extracts were combined, washed 3×150 mL $H_2O$, 1×150 mL brine, and dried over $Na_2SO_4$. Filtration, concentration of filtrate and drying gave a yellow oil, which was purified on a silica gel column (5% -10% ethyl acetate/hexanes gradient) to give 1.40 g (38%) of a yellow/green oil: MS (Cl, $NH_3$) 268 (M+H$^+$, base); Anal. calcd for $C_{17}H_{21}N_3$: C, 76.38; H, 7.92; N, 15.72. Found: C, 76.43; H, 7.53; N, 15.39.

E. 4-Cyano-4-(1-cyclohexyl-3-ethyl-1H-indazol-6-yl)-heptanedioic acid dimethyl ester This compound was prepared according to the method of example 2.G., using 1.33 g (4.98 mmol, 1.0 equiv) of (1-cyclohexyl-3-ethyl-1H-indazol-6-yl)-acetonitrile as starting material, to give 1.38 g (63%) of a yellow oil; MS (Cl, $NH_3$) m/z 440 (M+H$^+$, base); Anal. calcd for $C_{25}H_{33}N_3O_4$: C, 68.32; H, 7.57; N, 9.56. Found: C, 68.18; H, 7.52; N, 9.28.

F. 5-Cyano-5-(1-cyclohexyl-3-ethyl-1H-indazol-t-yl)-2-oxo-cyclohexanecarboxylic acid methyl ester This compound was prepared according to the method of example 2.H., using 1.33 g (3.03 mmol, 1.0 equiv) 4-cyano-(1-cyclohexyl-3-ethyl-1H-indazol-6-yl)-heptanedioic acid dimethyl ester as starting material, to give 983 mg (80%) of a white amorphous solid: MS (Cl, $NH_3$) m/z 408 (M+H$^+$, base); Anal. calcd for $C_{24}H_{29}N_3O_3$: C, 70.75; H, 7.18; N, 10.31. Found: C, 70.75; H, 7.33; N, 10.19.

G. 1-(1-Cyclohexyl-3-ethyl-1H-indazol-6-yl)-4-oxo-cyclohexanecarbonitrile

This compound was prepared according to the method of example 2.I., using 933 mg (2.29 mmol, 1.0 equiv) 5-cyano-5-(1-cyclohexyl-3-ethyl-1H-indazol-6-yl)-2-oxocyclohexane-carboxylic acid methyl ester as starting material, to give 588 mg (74%) of a white amorphous solid: MS (Cl, $NH_3$) m/z 350 (M+H$^+$, base); Anal. calcd for $C_{22}H_{27}N_3O$: C, 75.62; H, 7.79; N, 12.03. Found: C, 75.57; H, 7.90; N, 12.15.

EXAMPLE 7
Cis-4-cyano-4-(1-cyclohexyl-3-ethyl-1H-indazol-6-yl)-cyclohexanecarboxylic acid methyl ester and trans4-cyano-4-(1-cyclohexyl-3-ethyl-1H-indazol-6-yl)-cyclohexanecarboxylic acid methyl ester These compounds were prepared according to the method of example 3.B.,using 540 mg (1.20 mmol, 1.0 equiv) 1-(1-cyclohexyl-3-ethyl-1H-indazol-6-yl)-4-[1,3]dithian-2-ylidene-cyclohexane-carbonitrile as starting material, to give 117 mg (25%) of trans isomer as a white oily solid, and 233 mg (50%) of cis isomer as a white crystalline solid:

Data for trans isomer: $^1$H NMR (300 MHz, CDCl$_3$) d 7.68 (d, 1H, J=8.4 Hz), 7.50 (d, 1H, J=0.8 Hz), 7.13 (dd, 1H, J=1.6, 8.5 Hz), 4.34 (m, 1H), 3.74 (s, 3H), 2.98 (q, 2H, J+7.6 Hz), 2.85 (m, 1H), 2.35 (m, 2H), 1.9–2.2 (m, 12H), 1.8 (m, 2H), 1.55 (m, 2H), 1.37 (t, 3H, J=7.6 Hz); MS (Cl, NH$_3$) m/z 394 (M+H$^+$, base); Anal. calcd for $C_{24}H_{31}N_3O_2$: C, 73.25; H, 7.95; N, 10.68. Found: C, 73.07; H, 8.12; N, 10.89.

Data for cis isomer: 1H NMR (300 MHz, CDCl$_3$) d 7.68 (d, 1H, J=8.4 Hz), 7.53 (d, 1H, J=0.9 Hz), 7.14 (dd, 1H, J=1.6, 8.5 Hz), 4.34 (m, 1H), 3.74 (s, 3H), 2.98 (, 2H, J=7.6 Hz), 2.43 (m, 1H), 1.9–2.3 (m, 15H), 1.8 (m, 1H), 1.5 (m, 2H), 1.37 (t, 3H, JJ=7.6 Hz); (Cl, NH$_3$) m/z 394 (M+$^+$, base); Ana. calcd for $C_{24}H_{31}N_3O_2$: C, 73.25; H, 7.95; N. 10.68. Found: C, 73.17; H, 7.89; N, 10.43.

EXAMPLE 8
Cis-4-cyano-4-(1-cyclohexyl-3-ethyl-1H-indazol-6-yl)-cyclohexanecarboxylic acid This compound was prepared according to the method of example 5, using 201 mg (0.511 mmol, 1.0 equiv) cis-4-cyano-4-(1-cyclohexyl-3-ethyl-1H-indazol-6-yl)-cyclohexane-carboxylic acid methyl ester as starting material, to give 178 mg (92%) of a white crystalline solid, which was recrystallized from ethyl acetate hexanes to give 153 mg of a white crystalline powder; mp 192–194° C.; Anal. calculated for $C_{23}H_{29}N_3O_2$: C, 72.79; H, 7.70; N, 11.07. Found: C, 72.25; H, 7.99; N, 10.97.

EXAMPLE 9
Cis-1-(1-cyclohexyl-3-ethyl-1H-indazole-6-yl)-4-hydroxylmethylcyclohexane carbonitrile To a stirred solution of the product from Example 8 (220 mg, 0.58 mmol.) in dry tetrahydrofuran (5 mL) at 0° C. was added dropwise a solution of borane in tetrahydrofuran (1M, 1.3 mL, 1.3 mmol). The mixture was stirred at 0C for one hour then quenched by the slow addition of methanol (1 mL). The mixture was poured into water (100 mL) and extracted with ethyl acetate (2×100 mL). The organic extracts were combined, washed with water (1×20 mL), brine (1×20 mL) dried over magnesium sulfate and concentrated to give an oil. A separate identical experiment was carded out using the product from Example 8 (100 mg, 0.26 mmol.) and borane in tetrahydrofuran (1M, 0.6 mL, 0.58 mmol.). The crude product from both experiments were combined and chromatographed on Silica Gel eluting with 2.5% methanol in methylene chloride (v/v) to give an oil. Recrystallization from ethyl acetate/hexanes yielded 214 mg white solid (67%) mp 117–9° C. mass spectrum (m/e) 367 (M+1, 20), 366 (M+, 100).

EXAMPLE 10
Cis-4-Cyano-4-(1-cyclohexyl-3-ethyl-1H-indazol-6-yl)-cyclohexanecarboxylic acid amide A mixture of the product from Example 8 (150 mg, 0.4 mmol.) thionyl chloride (36 uL, 0.49 mmol) and dimethyl-formamide (5 mL) in dry methylene chloride (3 mL) was refluxed for four hours. The mixture was cooled to 0° C. and dry ammonia gas was bubbled with chloroform (200 mL), washed with water (1×40 mL) dried over magnesium sulfate and concentrated to give a solid. Recrystallization from ethyl acetate/hexane yielded 125 mg white solid (83%) mp 180–2° C. mass spectrum (m/e) (M+1, 20), 379 (M+, 100).

EXAMPLE 11
Trans-4-Cyano4-(1-cyclohexyl-3-ethyl-1H-indazol-6-yl)-cyclohexanecarboxylic acid amide The title compound was prepared in a manner analogous to the synthesis provided in Example 4. The melting point of the isolated product was 140–143° C.

EXAMPLE 12
Cis-1-(1-cyclohexyl-3-ethyl-1H-indazol-6-yl)-4-(1-hydroxy-1-methyl-ethyl)cyclohexanecarbonitrile To a stirred solution of cis cyano-4-(1-cyclohexyl-3-ethyl-1H-indazolol-6-yl)-cyclohexanecarboxylic acid methyl ester (360 mg, 0.90 mmol) in 10 mL of dry tetrahy-drofuran at −40° C. under nitrogen atmosphere was added 0.7 mL (2.1 mmol) of 3.0 M methyl magnesium bromide. Reaction mixture was allowed to warm up to room temperature over a period of one hour and stirred at room temperature for 3 hours. After this time, reaction mixture was quenched with excess of methanol (5.0 mL) and worked up by pouring into 100 mL of water and acidification with oxalic acid. Extraction with ethyl acetate followed by washing of ethyl acetate extract with water, brine and drying over magnesium sulfate (MgSO$_4$). Removal of ethyl acetate in vacuo gave crude final product which was homogenous by TLC analysis. Recrystallization from ethyl acetate/hexane gave 180 mg of pure final product or a white solid, mp=58–60° C. MS m/z 394 (M+H$^+$, base).

EXAMPLE 13
Cis-1-(1-cyclopentyl-3-ethyl-1H-indazol-6-yl)-4-hydroxycyclohexanecarbonitrile To a stirred solution of 2.9 g (8.6 mmol) 1-(1-cyclopentyl-3-ethyl-1H-indazol-6-yl)-4-oxo-cyclohexanecarbonitrile (compound 2G page 35 of PC) in 100 mL absolute methanol at 0° C. was added sodium borohydride 382 mg (10.8 mmol) portionwise. The mixture was stirred at 0° C. for 30 min, then quenched with 2 mL saturated ammonium chloride solution. The mixture was concentrated to a volume of 20 mL, poured into a mixture of 100 mL water and 100 mL saturated ammonium chloride solution and extracted with ethyl acetate (2×200 mL). The organic extract was combined, washed with water (1×100 mL), brine (1×100 mL), dried (MgSO$_4$) and concentrated to give an oil. Chromatography on silica gel eluting with ethyl acetate/hexanes (1:1) afforded an oil. Recrystallization from ethyl acetate/hexanes yielded 1.9 g (66%) cis-1-(1-cyclopentyl-3-ethyl-1H-indazole-6-yl)-4-hydroxycyclohexane-carbonitrile as a white solid. mp 107–109° C.

Anal. Calc'd. for $C_{21}H_{27}N_3O$: C, 74.74; H, 8.06; N, 12.45. Found: C, 74.81; H, 8.04; N, 12.43.

EXAMPLE 14

Cis-1-[3-ethyl-1(4-fluorophenyl)-1H-indazol-6-yl]4-hydroxy-cyclohexanecarbonitrile The title compound was prepared in an analogous manner to that described in the immediately preceding example for preparation of cis-1-(1-cyclopentyl-3-ethyl-1H-indazol-6-yl)-4-hydroxy-cyclohexanecarbonitrile, starting with 0.415 g (1.148 mmol) of 1-(4-fluorophenyl-3-ethyl-1H-indazol-6-yl)-4-oxo-cyclohexanecarbonitrile to give 0.28 g (76%) of white crystalline solid. mp =132–134° C.

Anal. Calc'd. for $C_{22}H_{22}N_3OF$: C, 72.71; H, 6.10; N, 11.56. Found: C, 72.55; H, 6.22; N, 11.40.

The 1-(4-fluorophenyl-3-ethyl-1H-indazol-6-yl)-4-oxo-cyclohexanecarbonitrile starting material was prepared from 6-bromo-3-ethyl-1-(4-fluorophenyl)-1H-indazole following the chemical synthesis sequence outlined in Scheme 3 (intermediate X→XIX) and described above in more detail.

EXAMPLE 15

Cis-1-(1-cyclohexyl-3-ethyl-1H-indazol-6-yl)-4-hydroxy-cyclohexanecarbonitrile

The title compound was prepared in an analogous manner to that described in a preceding example for preparation of cis-(1-cyclopentyl-3-ethyl-1H-indazol-6-yl)-4-hydroxy-cyclohexanecarbonitrile, starting with 1-(1-cyclohexyl-3-ethyl-1H-indazol-6-yl)-4-oxo-cyclohexanecarbonitrile. mp=124–126° C.; MS m/z 352 (M+H$^+$, base).

EXAMPLE 16

Trans-1-(1-Cyclobutyl-3-ethyl-1H-indazol-6-yl)-4-hydroxycyclohexanecarbonitrile

The title compound was prepared in an analogous manner to that described in a preceding example for preparation of cis-(1-cyclopentyl-3-ethyl-1H-indazol-6-yl)-4-hydroxy-cyclohexanecarbonitrile, starting from 1-(1-cyclobutyl-3-ethyl-1H-indazol-6-yl)-4-oxo-cyclohexanecarbonitrile. mp=60–65° C.; MS m/z 324 (M+H$^+$, base).

EXAMPLE 17

Cis-1-(1-cyclopentyl-3-ethyl-1H-indazol-6-yl-)4-hydroxy-4-methyl-cyclohexanecarbonitrile and trans-1-(1-cyclopentyl-3-ethyl-1H-indazol-6-yl)-4-hydroxy-4-methyl-cyclohexanecarbonitrile To a stirred suspension of 0.275 grams (1.115 mmol) of anhydrous $CeCl_3$ in 10 mL of dry tetra-hydrofuran under N2 atmosphere at 0° C. was added dropwise 0.4 mL (1.115 mmol) of 3.0 N $CH_3MgCl$. The reaction mixture was stirred at 0° C. for one hour. After this time, 0.3 g (0.891 mmol) of 1-(1-cyclopentyl-3-ethyl-1H-indazole-6-yl)-4-oxo-cyclohexanecarbonitrile dissolved in 10 mL of anhydrous tetrahydrofuran was added dropwise and the reaction mixture stirred at 0° C. for 1 hour. The mixture was quenched with 5 mL of 2N HOAc. The mixture was poured onto 100 mL of $H_2O$ and extracted with ethyl acetate (2×100 mL). The organic extracts were combined, washed with $H_2O$ (1×100 mL), brine (1×200 mL) and dried over $MgSO_4$. Filtration, concentration and purification on a silica gel column (2% EtOAc/hexane) gave 0.15 grams of less polar product (trans isomer) as amorphous solid. MS (Cl, $NH_3$) m/z 353 (M+H$^+$, base) and 0.045 grams of more polar product (cis isomer) as a white crystalline product. mp=156–158° C. MS (Cl, $NH_2$) m/z 352 (M+H$^+$, base).

EXAMPLE 18

Cis-4-cyano-4-(1-cyclobutyl-3-ethyl-1H-indazol-6-yl-)-cyclohexanecarboxylic acid This compound was prepared according to the method of Example 5 using 0.28 g (0.767 mmol) of cis-4-cyano-4-(1-cyclobutyl-3-ethyl-1H-indazol-6-yl)-cyclohexanecarboxylic acid methyl ester as a starting material to give 0.24 grams (89%) of white solid, which was recrystallized from ethyl acetate/hexane to give 0.15 grams of white crystalline product. mp=201–203° C.; MS (m/z) 352 (M+H$^+$, base).

EXAMPLE 19

Trans-4-cyano-4-(1-cyclobutyl-3-ethyl-1H-indazol-6-yl-)-cyclohexanecarboxylic acid This compound was prepared according to the method of Example 4 using 0.13 g (0.356 mmol) of trans-4-cyano-4-(1-cyclobutyl-3-ethyl-1H-indazol-6-yl)-cyclohexanecarboxylic acid methyl ester as a starting material to give white solid. Purification on silica gel column using 5% methanol/95% methylene chloride gave pure product (80 mg) which was recrystallized from ethyl acetate/hexane to give 43 mg of white crystalline solid; mp=157–159° C., MS (m/z) 312, (M+H$^+$, base).

EXAMPLE 20

6-Bromo-3-ethyl-1-(4-fluorophenyl)-1H-indazole

Methanesulfonic acid 5-bromo-2-propionyl-phenyl ester, prepared as described in U.S. Ser. No. 08/046,858, filed May 8, 1997 as Attorney Docket No. PC9798, 30 grams (97.66 mmol) was combined with 4-fluorophenyl hydrazine hydrochloride (31.76 g, 175.33 mmol) and sodium acetate (30 g, 364 mmol) in mesitylene (400 mL). The reaction mixture was heated to reflux in a Dean-Stark apparatus for 96 hours. The reaction mixture was cooled to room temperature and concentrated under reduced pressure. The crude product was diluted with 500 mL of diethyl ether and 600 mL of water. Organic layer was separated and aqueous layer extracted with 500 mL of ethyl acetate. Combined organic extracts were washed with water (2×600 mL), brine (1×200 mL), dried over $MgSO_4$ and concentrated which gave a brown-red oil. Hexane (600 mL) was added to crude reaction product and the mixture boiled in a steam bath for a few minutes. This was followed by cooling still the heterogeneous mixture to room temperature and allowing to stand at room temperature for 12–14 hours. The reaction mixture was filtered, undissolved solid washed with additional hexane and filtrate which contained approximately 80% pure desired product concentrated in vacuo to give brown-yellow solid. Purification of this product on silica gel column and eluting with 15% ethyl acetate/85% hexane gave 14.1 grams of light brown-tan solid. Recrystallization from hexane gave light tan needles. mp=72–73° C.; MS (APCl) m/z 319 (base).

EXAMPLE 21

4-[3-Ethyl-1-(4-fluorophenyl)-1H-indazole-6-yl]4-hydroxy-cyclohexanecarboxylic acid ethyl ester This compound was prepared according to the method described in Example 6 of U.S. Ser. No. 08/046,858, filed May 8, 1997 as Attorney Docket No. PC9798, starting with 3.0 grams (9.4 mmol) of 6-bromo-3-ethyl-1-(4-fluorophenyl)-1H-indazole and 2.0 grams (11.7 mmol) of 4-oxo-cyclohexanecarboxylic acid ethyl ester to give after silica gel flash column chromatography (using 20% ethyl acetate 80% hexane as elutant) 2.17 grams of light yellow semi-solid which was a mixture of diastereoisomers. $^1$H NMR (400 MHz, $CDCl_3$) δ1.25–1.3 (t, 3H); 1.4–1.5 (t, 3H); 1.6–1.78 (m, 2H); 1.8–2.5 (m, 7H); 2.70 (m, 1H); 3.04 (m, 2H); 4.16 (m, 2H); 7.17–7.28 (m, 3H); 7.61–7.79 (m, 4H); MS, m/z 324.4 (M+H$^+$, base).

EXAMPLE 22
4-Cyano-4-13-ethyl-1-(4-fluorophenyl)-1H-indazole-6-yl]cyclohexanecarboxylic acid ethyl ester and 4-[3-ethyl-1-(4-fluoro-phenyl)-1H-indazol-6-yl]cyclohex-3-enecarboxylic acid ethyl ester This compound was prepared according to the method described in Example 7 of U.S. Ser. No. 08/046,858, filed May 8, 1997 as Attorney Docket No. PC9798, starting with 2.1 grams (5.12 mmol) of 4-[3-ethyl-1-(4-fluorophenyl)-1H-indazole-6-yl]4hydroxy-cyclohexanecarboxylic acid ethyl ester to give after silica gel Flash 40 Biotage column chromatography (10% EtOAc/90% hexane) 0.714 grams of product which existed as a mixture of diastereoisomers. MS, m/z 420 (M+H$^+$, base); $^1$H NMR (400 MHz, CDCl$_3$) δ1.27 (t, J=7.26, 3H), 1.43 (t, J=7.68, 3H), 1.57 (S, 2H), 1.85–1.98 (m, 2H); 2.02–2.19 (m, 2H); 2.18–2.40 (m, 3H); 3.04 (q, J=7.67, 2H); 4.15 (q, J=7.26, 2H); 7.2–7.3 (m, 3H); 7.61 (m, 2H); 7.71 (s, 1H); 7.71 (d, J=8.5, 1H). In addition to the desired product 4-cyano-4-[3-ethyl-1-(4-fluorophenyl)-1H-indazol-6-yl]cyclohexanecarboxylic acid ethyl ester, a major byproduct, namely 4-[3-ethyl-1-(4-fluoro-phenyl)-1H-indazol-6-yl]cyclohex-3-enecarboxylic acid ethyl ester (1.16 grams) was obtained. MS m/z 393 (M+H$^+$, base). $^1$H NMR (400 MHz, CDCl$_3$) δ1.24 (m, 3H); 1.43 (m, 3H); 1.6–2.7 (m, 7H); 3.02 (m, 2H); 4.13 (m, 2H); 6.17 (br, s 1H); 7.15–7.25 (m, 4H); 7.50 (s, 1H); 7.61–7.67 (m, 2H).

EXAMPLE 23
Cis-4-cyano-4-[3-ethyl-1-(4-fluorophenyl)-1H-indazol-6-yl]-cyclohexanecarboxylic acid This compound was prepared in analogous manner as cis4-cyano-4-(1-cyclohexyl-3-ethyl-1H-indazol-6-yl)-cyclohexanecarboxylic acid, synthesis of which is described in detail in Schemes I and II of U.S. Ser. No. 08/048,858, filed May 8, 1997 as Attorney Docket No. PC9798, starting with 0.71 grams (1.694 mmol) of 4-cyano-4-[3-ethyl-1-(4-fluorophenyl)-1H-indazol-6-yl]-cyclohexanecarboxylic acid ethyl ester.

mp=173–175° C.; MS m/z 392 (M+H$^+$, base). Anal. Calc'd for C$_{23}$H$_{23}$O$_2$N$_2$F: C, 70.57; H, 5.66; N, 10.73. Found: C, 70.39; H, 5.61; N 10.82. $^1$H NMR (400 MHz, CDCl$_3$) δ 1.42–1.45 (t, J=7.57, 3H); 1.91 (t, J=13.28, 2H); 2.09 (m, 2H); 2.23–2.35 (m, 4H); 2.40–2.48 (m, 1H); 3.06 (q, J=7.67, 2H); 7.2–7.26 (m, 2H); 7.29 (d, J=7.47, 1H); 7.60 (m, 2H); 7.71 (s, 1H); 7.78 (d, J=8.5, 7H).

Alternatively, cis-4-cyano-4-[3-ethyl-1-(4-fluorophenyl)-1H-indazole-6-yl]cyclohexane-carboxylic acid can be prepared in analogous manner as cis-4-cyano-4-(1-cyclohexyl-3-ethyl-1H-indazol-6-yl)cyclohexanecarboxylic acid starting with 6-bromo-3-ethyl-1-(4-fluorophenyl)-1H-indazole following the synthetic steps outlined in Scheme 2, step 5, and Scheme 3, steps 1–7 described further above in more detail.

EXAMPLE 24
4-(3-ethyl-1-(4-fluorophenyl)-1H-indazol-6-yl)-cyclohex-3-ene-carboxylic acid To a stirred solution of 1.13 g (2.87 mmol) of 4-(3-ethyl-1-(4-fluorophenyl)-1H-indazol-6-yl)-cyclohex-3-ene-carboxylic acid ethyl ester dissolved in 50 mL of methanol and 15 mL of tetrahydrofuran was added 8.62 mL (8.61 mmol) of 1N sodium hydroxide and reaction mixture heated to reflux for 3 hr. After 3 hr, the reaction mixture was concentrated on a rotary evaporator, diluted with 200 mL of H$_2$O, acidified to pH 1 with 1N HCl and extracted 2×200 mL ethyl acetate. The organic extracts were combined, washed with water, brine and dried over Na$_2$SO$_4$. Filtration, concentration and drying gave crude product. Recrystallization from ethyl acetate/hexane gave 0.31 grams of white crystalline product. mp=214–216° C.; MS, m/z 365 (M+H$^+$, base).

EXAMPLE 25
1-Cyclohexyl-3-ethyl-6-fluoro-1H-indazole

To a solution of 1-(2,4-difluoro-phenyl)-propan-1-one (21.29 g, 125.1 mmol) in toluene (120 mL) was added sodium acetate (26.75 g, 326.1 mmol) and cyclohexylhydrazine mesylate (34.0 g, 163 mmol). The reaction mixture was heated to reflux in a Dean-Stark apparatus for 12 hours. The reaction was cooled to room temperature and poured into 1N hydrochloric acid (100 mL). The toluene layer was separated and washed with water (75 mL) and brine (75 mL). The organic layer was dried over magnesium sulfate, filtered, and concentrated to yield 30.07 g of 1-cyclohexyl-3-ethyl-6-fluoro-1H-indazole (98% yield). $^1$H NMR (400 MHz, CDCl$_3$) d 1.33 (t, 3, J=7.7), 1.35–1.44 (m, 2), 1.47–1.96 (m, 8), 2.93 (q, 2, J=7.7) 4.14–4.22 (m, 1), 6.81 (dt, 1, J=8.9, 2.1), 6.99 (dd, 1, J=9.8, 2.1), 7.40 (ddd, 1, J=8.7, 5.2, 0.4). $^{13}$C NMR (100 MHz, CDCl$_3$) d 13.97, 20.53, 25.37, 25.84, 32.32, 58.18, 94.77 (d, J=27.4), 109.11 (d, J=26.0), 119.38, 121.75 (d, J=11.5), 139.89 (d, J=13.0), 146.61, 161.95 (d, J=242). IR2968, 2934, 2856, 1624, 1507, 1174, 1125, 825 cm$^{-1}$. Analysis calculated for C$_{15}$H$_{19}$FN$_2$: C, 73.14; H, 7.77; N, 11.37. Found: C, 73.33; H, 7.90; N, 11.46.

EXAMPLE 26
1-(1-Cyclohexyl-3-ethyl-1H-indazol-6-yl)cyclohexane-1,4-dicarbonitrile To a solution of 1-cyclohexyl-3-ethyl-6-fluoro-1H-indazole (1.50 g, 6.09 mmol) and cylohexane-1,4-dicarbonitrile (3.27 g, 24.4 mmol) in toluene (15 mL) was added potassium bis(trimethylsilyl) amide (1.82g, 9.12 mmol). The reaction mixture was heated to 100° C. and stirred for 5 hours. The reaction mixture was cooled to room temperature and poured into 1N HCl (15 mL). The layers were separated and the organic extracts were concentrated. The crude product was stirred in 20% EtOAc/Hexanes (15 mL) for 20 minutes and the solids were filtered (1.1 g of cylohexane-1,4-dicarbonitrile recovered). The filtrate was concentrated to a crude oil. For characterization purposes, the diastereoisomers were obtained by purification by chromatography on silica gel (125 g) eluting with 2:1 hexanes/ethylacetate (1.69 g product isolated, 77% yield). Higher Rf diastereoisomer: $^1$H NMR (400 MHz, CDCl$_3$) d 1.37 (t, 3, J=7.7), 1.24–1.78 (m, 4), 1.92–2.10 (m, 6), 2.19–2.35 (m, 8), 2.98 (q, 2, J=7.7), 3.15–3.17 (m, 1), 4.30–4.39 (m, 1), 7.19 (dd, 1, J=8.5, 1.7), 7.51 (d, 1, J=0.8), 7.71 (d, 1, J=8.5). $^{13}$C NMR (100 MHz, CDCl$_3$) d 14.07, 20.60, 25.34, 25.79, 25.92, 32.61, 33.36, 44.30, 57.66, 105.92, 117.04, 121.00, 121.52, 121.79, 122.09.137.33, 139.54, 146.41. IR2934, 2239, 1620, 1448, 1435, 1238, 1049, 803 cm$^{-1}$. Analysis calculated for C$_{25}$H$_{28}$N$_4$: C, 76.63; H, 7.83; N, 15.54. Found: C, 76.69; H, 7.87; N, 15.65. Lower Rf diastereoisomer: $^1$H NMR (400 MHz, CDCl$_3$) d 1.36 (t, 3, J=7.7), 1.42–1.53 (m, 2), 1.74–1.82 (m, 2), 1.89–2.08 (m, 8), 2.17–2.34 (m, 6), 2.58 (tt, 1, J=12.2, 3.5), 2.97 (q, 2, J=7.7), 4.284.36 (m, 1), 7.09 (dd, 1, J=8.5, 1.7), 7.49 (d, 1, J=1.0), 7.69 (d, 1, J=8.5). $^{13}$C NMR (100 MHz, CDCl$_3$) d 14.02, 20.57, 25.32, 25.81, 27.07, 27.27, 32.57, 36.04, 43.63, 57.75, 106.05, 116.65, 121.17, 121.50, 122.13, 137.17, 139.54, 146.38. IR2935, 2231, 1620, 1447, 1211, 1061, 807 cm$^{-1}$. Analysis calculated for C$_{25}$H$_{28}$N$_4$: C, 76.63; H, 7.83; N, 15.54. Found: C, 76.52; H, 7.95; N, 15.37.

EXAMPLE 27

4-Cyano-4-(1-cyclohexyl-3-ethyl-1H-indazol-6-yl) cyclohexanecarboxylic acid ethyl ester

To a solution of 1-(1-cyclohexyl-3-ethyl-1H-indazol-6-yl)-cyclohexane-1,4-dicarbonitrile (2.58g, 7.16 mmol) in ethanol (35 mL) was bubbled hydrochloric acid gas for 20 minutes. The reaction mixture was stirred 20 minutes after which the solvent was concentrated. To the crude product was added toluene (20 mL) and water (20 mL) and the mixture was stirred for 8 hours. The layers were separated and the toluene layer was concentrated to a crude foam. For characterization purposes, the diastereoisomers were obtained by purification by chromatography on silica gel eluting with 4:1 hexanes/ethylacetate (2.37g product isolated, 81% yield).

What is claimed is:

1. A method for obtaining an indazole compound to treat a condition selected from acute respiratory distress syndrome, bronchitis, chronic obstructive pulmonary disease (COPD), asthma, chronic bronchitis, pulmonary emphysema, or silicosis, said method comprising (a) identifying a catechol compound which treats said condition and (b) obtaining said indazole compound by synthesizing said indazole compound having the same chemical structure as said catechol compound, except that said catechol moiety is replaced by an indazole moiety.

2. A method according to claim 1 wherein said indazole compound is a compound of Formula (IA) or (IB):

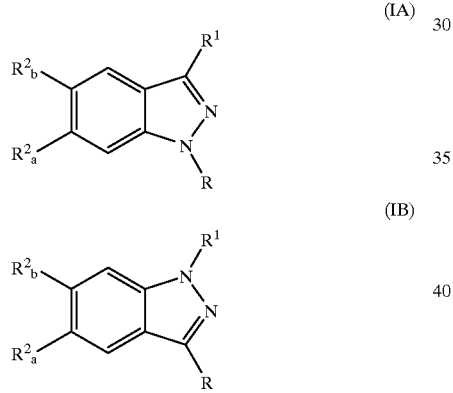

and pharmaceutically acceptable salts thereof;
wherein
—R is a member selected from the group consisting of hydrogen, $(C_1-C_9)$ alkyl; $—(CH_2)_n(C_3-C_{10})$ cycloalkyl wherein n is an integer selected from 0, 1, and 2; $(C_1-C_6)$ alkoxy$(C_1-C_6)$ alkyl; $(C_2-C_6)$ alkenyl; $—(CH_2)_n(C_3-C_9)$ heterocyclyl wherein n is an integer selected from 0, 1, and 2; and $—(Z^1)_b(Z^2)_c(C_6-C_9)$ aryl wherein b and c are integers independently selected from 0 and 1, $Z^1$ is $(C_1-C_6)$ alkylene or $(C_2-C_6)$ alkenylene, and $Z^2$ is O, S, $SO_2$, or $NR^{119}$; and further wherein said heterocyclyl is a member independently selected from the group consisting essentially of acridinyl; benzimidazolyl; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholmyl; 1,8-naphthyridinyl; oxadiazolyl; 1,3-oxathiolane; oxazolidmyl; oxazolyl; oxiranyl; parathiazinyl; phenazinyl; phenothiazinyl; phenoxazinyl; phthalazinyl; piperazinyl; piperidmyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; wherein said aryl is a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; wherein said alkyl, alkenyl, alkoxyalkyl, heterocyclyl, and aryl moieties defining said R groups are substituted by 0 to 3 substituents where each said substituent comprises a member independently selected from the group consisting essentially of bromo, chloro, or fluoro; hydroxy; $(C_1-C_5)$ alkyl; $(C_2-C_5)$ alkenyl; $(C_1-C_5)$ alkoxy; $(C_3-C_6)$ cycloalkoxy; mono-, di-, and tri-fluoromethyl; nitro; $—C(=O)OR^{119}$, $—C(=O)NR^{119}R^{120}$, $—NR^{119}R^{120}$ and $—S(=O)_2NR^{119}R^{120}$;

—$R^1$ is a member selected from the group consisting of hydrogen; $(C_1-C_9)$ alkyl; $(C_2-C_3)$ alkenyl; phenyl; $(C_3-C_7)$ cycloalkyl; and $(C_3-C_7)$ cycloalkyl$(C_1-C_2)$ alkyl; wherein said alkyl, alkenyl and phenyl moieties defining said $R^1$ groups are substituted by 0 to 3 substituents where each said substituent comprises a member independently selected from the group consisting essentially of methyl; ethyl; mono-, di-, and tri-fluoromethyl; and bromo, chloro, or fluoro; and —$R^2_a$ and $R^2_b$ are each a member independently selected from the group consisting of hydrogen and hereinafter recited substituents, provided that one, but not both of $R^2_a$ and $R^2_b$ must be independently selected as hydrogen; wherein said substituents comprise the following: a moiety of partial Formulas (IC), (ID), (IE), or (IF):

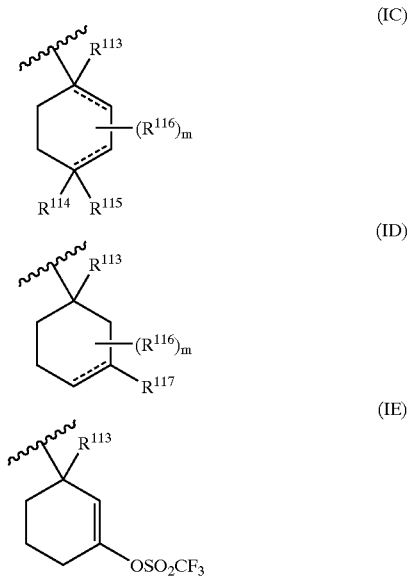

(IF)

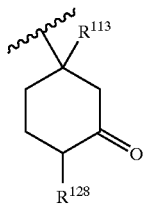

wherein the dashed lines in formulas (IC) and (ID) independently and optionally represent a single or double bond, provided that in formula (IC) both dashed lines cannot both represent double bonds at the same time;

m is an integer selected from 0, 1, 2, 3, and 4, and when 2, may apply to a single carbon atom on the ring;

—$R^{113}$ is a member selected from the group consisting of H; bromo, chloro, or fluoro; cyano; ($C_2$–$C_4$) alkynyl substituted by 0 or 1 substituent where said substituent is a member selected from the group consisting essentially of phenyl, pyridyl and pyrimidinyl; ($C_1$–$C_4$) alkyl substituted by 0 to 6 bromo, chloro, or fluoro; —$CH_2NHC(=O)C(=O)NH_2$; cyclopropyl substituted by 0 or 1 substituent where said substituent is a member selected from the group consisting essentially of $R^{121}$; $R^{127}$; $CH_2OR^{119}$; $NR^{119}R^{120}$; $CH_2NR^{119}R^{120}$; $C(=O)OR^{119}$; $C(=O)NR^{119}R^{120}$; $C\equiv CR_{11}$; $C(Z)H$; and —$CH=CR^{121}R^{121}$; provided that $R^{113}$ is H in Formula (IC) when the dashed line for the ring carbon of $R^{113}$ attachment represents a double bond;

—$R^{114}$ is a member selected from the group consisting of H; $R^{116}$; $C(Y)R^{124}$; $C(=O)OR^{124}$; $C(Y)NR^{127}R^{124}$; CN; $C(NR^{127})NR^{127}R^{124}$; $C(NOR^{119})R^{124}$; $C(=O)NR^{119}NR^{119}C(=O)R^{119}$; $C(=O)NR^{119}NR^{127}R^{124}$; $C(NOR^{124})R^{119}$; $C(NR^{119})NR^{127}R^{124}$; $C(NR^{124})NR^{119}R^{120}$; $C(NCN)NR^{127}R^{124}$, $C(NCN)S(C_1$–$C_4)$ alkyl; $CR^{119}R^{120}OR^{124}$, $CR^{119}R^{120}SR^{124}$, $CR^{119}R^{120}S(O)_nR^{125}$ where n is an integer selected from 0, 1, and 2; $CR^{119}R^{120}NR^{124}R^{127}$; $CR^{119}R^{120}NR^{127}S(=O)_2R_{15}$; $CR^{119}R^{120}NR^{127}C(Y)R^{124}$; $CR^{119}R^{120}NR^{127}C(=O)OR^{125}$; $CR^{119}R^{120}NR^{127}C(Y)NR^{127}R^{124}$; $CR^{119}R^{120}NR^{127}C(NCN)NR^{127}R^{124}$; $CR^{119}R^{120}NR^{127}C(CR^{119}NO_2)S(C_1$–$C_4)$ alkyl; $CR^{119}R^{120}C(=O)OR^{125}$; $CR^{119}R^{120}C(Y)NR^{127}R^{124}$; $CR^{119}R^{120}C(NR^{127})NR^{127}R^{124}$; $CR^{119}R^{120}CN$; $CR^{119}R^{120}C(NOR^{120})R^{124}$; $CR^{119}R^{120}C(NOR^{124})R^{120}$; $CR^{119}R^{120}NR^{127}C(NR^{127})S(C_1$–$C_4)$ alkyl; $CR^{119}R^{120}NR^{127}C(NR^{127})NR^{127}R^{124}$; $CR^{119}R^{120}NR^{127}C(=O)C(=O)NR^{127}R^{124}$; $CR^{119}R^{120}NR^{127}C(=O)C(=O)OR^{124}$; tetrazolyl; thiazolyl; imidazolyl; imidazolidinyl; pyrazolyl; thiazolidinyl; oxazolyl; oxazolidinyl; triazolyl; isoxazolyl; oxadiazolyl; thiadiazolyl; $CR^{119}R^{120}$(tetrazolyl); $CR^{119}R^{120}$(thiazolyl); $CR^{119}R^{120}$(imidazolyl); $CR^{119}R^{120}$(imidazolidinyl); $CR^{119}R^{120}$(pyrazolyl); $CR^{119}R^{120}$(thiazolidinyl); $CR^{119}R^{120}$(oxazolyl); $CR^{119}R^{120}$(oxazolidinyl); $CR^{119}R^{120}$(triazolyl); $CR^{119}R^{120}$(isoxazolyl); $CR^{119}R^{120}$(oxadiazolyl); $CR^{119}R^{120}$(thiadiazolyl); $CR^{119}R^{120}$(morpholinyl); $CR^{119}R^{120}$(piperidinyl); $CR^{119}R^{120}$(piperazinyl); and $CR^{119}R^{120}$(pyrrolyl); said heterocyclic groups being substituted by 0 to 3 substituents $R^{124}$;

—$R^{115}$ is a member selected from the group consisting of $R^{119}$; $OR^{119}$; —$CH_2OR^{119}$; cyano; $C(=O)R^{119}$; $C(=O)OR^{119}$; $C(=O)NR^{119}R^{120}$; and $NR^{119}R^{120}$;

provided that $R^{115}$ is absent when the dashed line in Formula (9.2) represents a double bond;

or

—$R^{114}$ and $R^{115}$ are taken together to form =O or =$R^{118}$;

or

—$R^{115}$ is hydrogen and $R^{114}$ is $OR^{124}$; $SR^{124}$; $S(O)_nR^{125}$, where n is an integer selected from 0, 1, and 2; $S(=O)_2NR^{127}R^{124}$; $NR^{127}R^{124}$; $NR^{124}C(=O)R^{119}$; $NR^{127}C(Y)R^{124}$; $NR^{127}C(=O)OR^{125}$; $NR^{127}C(Y)NR^{127}R^{124}$; $NR^{127}S(=O)_2NR^{127}R^{124}$; $NR^{127}C(NCN)NR^{127}R^{124}$; $NR^{127}S(=O)_2R^{125}$; $NR^{127}C(CR^{119}NO_2)NR^{127}R^{124}$; $NR^{127}C(NCN)S(C_1$–$C_4)$ alkyl; $NR^{127}C(CR^{119}NO_2)S(C_1$–$C_4)$ alkyl; $NR^{127}C(NR^{127})NR^{127}R^{124}$; $NR^{127}C(=O)C(=O)NR^{127}R^{124}$; or $NR^{127}C(=O)C(=O)OR^{124}$;

—$R^{116}$ is a member selected from the group consisting of methyl and ethyl substituted by 0 to 5 bromo, chloro, or fluoro, wherein m may be 2 with respect to a single ring carbon atom to which $R^{116}$ is attached;

—$R^{117}$ is a member selected from the group consisting of $OR^{124}$; $SR^{124}$; $SO_2NR^{127}R^{124}$; $NR^{127}R^{124}$; $NR^{124}C(=O)R^{119}$; $NR^{127}C(Y)R^{124}$; $R^{127}C(=O)OR^{125}$; $S(O)_nR_{12}$ where n is an integer selected from 0, 1, and 2; $OS(=O)_2R^{122}$; $OR^{122}$; $OC(=O)NR^{123}R^{122}$; $OC(=O)R^{123}$; $OC(=O)OR^{123}$; $O(CR^{122}R^{123})_mOR^{122}$ where m is an integer selected from 0, 1, and 2; $CR^{119}R^{120}OR^{124}$; $CR^{119}R^{120}NR^{127}R^{124}$; $C(Y)R^{124}$; $C(=O)OR^{124}$; $C(Y)NR^{127}R^{124}$; CN; $C(NR^{127})NR^{127}R^{124}$; $C(NOR^{119})R^{124}$; $C(=O)NR^{119}NR^{119}C(=O)R^{119}$; $C(=O)NR^{119}NR^{127}R^{124}$; $C(NOR^{124})R^{119}$; $C(NR^{119})NR^{127}R^{124}$; $C(NR^{124})NR^{119}R^{120}$; $C(NCN)NR^{127}R^{124}$; $C(NCN)S(C_1$–$C_4)$ alkyl; tetrazolyl; thiazolyl; imidazolyl; imidazolidinyl; pyrazolyl; thiazolidinyl; oxazolyl; oxazolidinyl; triazolyl; isoxazolyl; oxadiazolyl; and thiadiazolyl; where the recited heterocyclic groups are substituted by 0 to 3 substituents where said substituent is $R^{124}$;

—$R^{118}$ is a member selected from the group consisting of —$NR^{125}$; —$NCR^{119}R^{120}(C_2$–$C_6)$ alkenyl; —$NOR^{124}$; —$NOR^{129}$; —$NOCR^{119}R^{120}(C_2$–$C_6)$ alkenyl; —$NNR^{119}R^{124}$; —$NNR^{119}R^{129}$; —NCN; —$NNR^{119}C(Y)NR^{119}R^{124}$; —$C(CN)_2$; —$CR^{124}CN$; —$CR^{124}C(=O)OR^{119}$; —$CR^{124}C(=O)NR^{119}R^{124}$; —$C(CN)NO_2$; —$C(CN)C(=O)O(C_1$–$C_4)$ alkyl; —$C(CN)OC(=O)O(C_1$–$C_4)$ alkyl; —$C(CN)(C_1$–$C_4)$ alkyl; —$C(CN)C(=O)NR^{119}R^{124}$; 2-(1,3-dithiane), 2-(1,3-dithiolane), dimethylthio ketal, diethylthio ketal, 2-(1,3-dioxolane), 2-(1,3-dioxane), 2-(1,3-oxathiolane); dimethyl ketal and diethyl ketal;

—$R^{119}$ and $R^{120}$ are each a member independently selected from the group consisting of hydrogen and ($C_1$–$C_4$) alkyl substituted by 0 to 3 fluorine atoms;

—$R^{121}$ is fluoro; or $R^{120}$;

$R^{122}$ is a member selected from the group consisting of ($C_1$–$C_6$) alkyl; ($C_2$–$C_3$) alkenyl; ($C_3$–$C_7$) cycloalkyl; ($C_3$–$C_7$) cycloalkyl($C_1$–$C_2$) alkyl; ($C_6$–$C_{10}$) aryl; and ($C_3$–$C_9$) heterocyclyl; where said aryl and heterocyclyl are as defined under $R^A_5$ above; and where said $R^{122}$ groups are substituted with 0 to 3 substituents selected from the group consisting of methyl; ethyl; mono-, di-, and tri-fluoromethyl; and bromo, chloro, or fluoro;

—$R^{123}$ is a member selected from the group consisting of hydrogen and $R^{122}$;

—$R^{124}$ is a member selected from the group consisting of hydrogen and $R^{125}$; or when $R^{124}$ and $R^{27}$ appear together as $NR^{127}R^{124}$ then $R^{127}$ and $R^{124}$ may be taken together with the nitrogen to which they are attached to form a 5- to 7-membered ring optionally containing one additional heteroatom selected from O, N and S; p1

—$R^{125}$ is a member selected from the group consisting of($C_1$–$C_6$) alkyl and —$(CR^{119}R^{120})_nR^{126}$, where n is an integer selected from 0, 1, and 2 and $R^{126}$ and said ($C_1$–$C_6$) alkyl are substituted by 0 to 3 substituents where each said substituent is a member selected from the group consisting of bromo, chloro, or fluoro; nitro; cyano; $NR^{120}R^{127}$; (=O)$R^{119}$; $OR^{119}$; C(=O)$NR^{120}R^{127}$; OC(=O)$NR^{120}R^{127}$; $NR^{127}$C(=O)$NR^{127}R^{120}$; $NR^{127}$C(=O)$R^{120}$; $NR_{17}$C(=O)O($C_1$–$C_4$) alkyl; C($NR^{127}$)$NR^{127}R^{120}$; C(NCN)$NR^{127}R^{120}$; C(NCN)S($C_1$–$C_4$) alkyl; $NR^{127}$C(NCN)S($C_1$–$C_4$) alkyl; $NR^{127}$C(NCN)$NR^{127}R^{120}$; $NR^{127}$S(=O)$_2$($C_1$–$C_4$) alkyl; S(O)$_n$($C_1$–$C_4$) alkyl; where n is an integer selected from 0, 1, and 2; $NR^{127}$C(=O)C(=O)$NR^{127}R^{120}$, $NR^{127}$C(=O)C(=O)$R^{127}$; thiazolyl; imidazolyl; oxazolyl; pyrazolyl; triazolyl; tetrazolyl; and ($C_1$–$C_2$) alkyl substituted with 0 to 3 fluorine atoms;

—$R^{126}$ is a member selected from the group consisting of ($C_3$–$C_7$) cycloalkyl; pyridyl; pyrimidyl; pyrazolyl; imidazolyl; triazolyl; pyrrolyl; piperazinyl; piperidinyl; morpholinyl; furanyl; thienyl; thiazolyl; quinolinyl; naphthyl; and phenyl;

—$R^{127}$ is a member selected from the group consisting of $OR^{119}$ and $R^{120}$;

—$R^{128}$ is a member selected from the group consisting of H; C(Y)$R^{124}$; C(=O)$OR^{124}$; C(Y)$NR^{127}R^{124}$; CN; C($NR^{127}$)$NR^{127}R^{124}$; C($NOR^{119}$)$R^{124}$; C(=O)$NR^{119}NR^{119}$C(=O)$R^{119}$; C(=O)$NR^{119}NR^{127}R^{124}$; C($NOR^{124}$)$R^{119}$; C($NR^{119}$)$NR^{127}R^{124}$; C($NR^{124}$)$NR^{119}R^{120}$; C(NCN)$NR^{127}R^{124}$; C(NCN)S($C_1$–$C_4$) alkyl; $CR^{119}R^{120}OR^{124}$; $CR^{119}R^{120}SR^{124}$; $CR^{119}R^{120}S(O)_nR^{125}$, where n is an integer selected from 0, 1, and 2; $CR^{119}R^{120}NR^{124}R^{127}$; $CR^{119}R^{120}NR^{127}S(=O)_2R^{125}$;$CR^{119}R^{120}NR^{127}C(Y)R^{124}$; $CR^{119}R^{120}NR^{127}C(=O)OR^{125}$; $CR^{119}R^{120}NR^{127}C(Y)NR^{127}R^{124}$; $CR^{119}R^{120}NR^{127}C(NCN)NR^{127}R^{124}$; $CR^{119}R^{120}NR^{127}C(CR_9NO_2)S(C_1$–$C_4)$ alkyl; tetrazolyl; thiazolyl; imidazolyl; imidazolidinyl; pyrazolyl; thiazolidinyl; oxazolyl; oxazolidinyl; triazolyl; isoxazolyl; oxadiazolyl; thiadiazolyl; wherein said recited heterocyclic groups are substituted by 0 to 3 substituents where each said substituent is selected from the group consisting of $R^{124}$;

—$R^{129}$ is a member selected from the group consisting of —C(=O)$R^{12}$; —C(=O)$NR^{119}R^{124}$; —S(=O)$_2R^{125}$; and —S(=O)$_2NR^{119}R^{124}$;

—Y is O or S;

and

Z is O; $NR^{127}$; NCN; C(—CN)$_2$; $CR^{119}$CN; $CR^{119}NO_2$; $CR^{119}$C(=O)$NR^{119}R^{120}$; C(—CN)C(=O)(O$C_1$–$C_4$) alkyl); or C(—CN)C(=O)$NR^{119}R^{120}$.

3. A method according to claim 2 wherein for said indazole compound R is phenyl substituted by fluoro; $R^1$ is ($C_1$–$C_2$) alkyl; one of $R^2_a$ and $R^2_b$ is hydrogen and the other is a substituent of Formula (IC) where the dashed line represents a single bond, $R^{113}$ is cyano, and $R^{115}$ and $R^{114}$ are both hydrogen.

4. A method according to claim 3 wherein for said indazole compound $R^1$ is ethyl.

5. A method according to claim 2 wherein for said indazole compound R is a member selected from the group consisting of cyclohexyl, cyclopentyl, cyclobutyl, methylenecyclopropyl, isopropyl, phenyl, and 4-fluorophenyl.

6. A method according to claim 2 wherein for said indazole compound one of $R^2_a$ and $R^2_b$ is hydrogen and the other is a group of partial Formula (IC) wherein the dashed line attached to the ring carbon atom to which $R^{113}$ is attached represents a single bond; and $R^{113}$ and $R^{114}$ are cis with respect to each other.

7. A method according to claim 2 wherein for said indazole compound $R^{113}$ is cyano.

8. A method according to claim 7 wherein for said indazole compound m is 0; $R^{115}$ is hydrogen; and $R^{114}$ is a member selected from the group consisting of —OH; —CH$_2$OH; —C(CH$_3$)$_2$OH; —C(=O)OH; —(=O)OCH$_3$; —C(=O)OCH$_2$CH$_3$; and —CH$_2$C(=O)NH$_2$.

9. A method according to claim 8 wherein for said indazole compound R is a member selected from the group consisting of cyclobutyl, cyclopentyl, cyclohexyl, and 4-fluoro-phenyl; $R^1$ is ethyl; and $R^{114}$ is —C(=O)OH.

10. A method according to claim 1 wherein for said indazole compound agent said compound of Formula (IA) or (IB) is a member selected from the group consisting of:

1-(1-Cyclopentyl-3-ethyl-1H-indazol-6-yl)-4-oxocyclohexanecarbonitrile;

Trans-4-cyano-4-(1-cyclopentyl-3-ethyl-1H-indazol-6-yl)cyclohexanecarboxylic acid methyl ester;

Cis-4-cyano-4-(1-cyclopentyl-3-ethyl-1H-indazol-6-yl)cyclohexanecarboxylic acid methyl ester;

Trans-4-cyano-4-(1-cyclopentyl-3-ethyl-1H-indazol-6-yl)cyclohexanecarboxylic acid;

Cis-4-cyano-4-(1-cyclopentyl-3-ethyl-1H-indazol-6-yl)cyclohexanecarboxylic acid;

1-(1-Cyclohexyl-3-ethyl-1H-indazol-6-yl)-4-oxocyclohexanecarbonitrile;

Cis-4-cyano-4-(1-cyclohexyl-3-ethyl-1H-indazol-6-yl)cyclohexanecarboxylic acid methyl ester;

Trans-4-cyano-4-(1-cyclohexyl-3-ethyl-1H-indazol-6-yl)cyclohexanecarboxylic acid methyl ester;

Cis-4-cyano-4-(1-cyclohexyl-3-ethyl-1H-indazol-6-yl)cyclohexanecarboxylic acid;

Trans-4-cyano-4-(1-cyclohexyl-3-ethyl-1H-indazol-6-yl)cyclohexanecarboxylic acid;

Cis-1-(1-cyclohexyl-3-ethyl-1H-indazole-6-yl)-4-hydroxymethylcyclohexanecarbonitrile;

Cis-4-cyano-4-(1-cyclohexyl-3-ethyl-1H-indazol-6-yl)cyclohexanecarboxylic acid amide;

Trans-4-cyano-4-(1-cyclohexyl-3-ethyl-1H-indazol-6-yl)cyclohexanecarboxylic acid amide;

Cis-1-(1-cyclohexyl-3-ethyl-1H-indazol-6-yl)-4-(1-hydroxy-1-methylethyl)cyclohexanecarbonitrile;

Cis-1-(1-cyclohexyl-3-ethyl-1H-indazol-6-yl)-4-hydroxycyclohexanecarbonitrile;

Cis-1-[3-ethyl-1-(4-fluorophenyl)-1H-indazol-6-yl]-4-hydroxycyclohexanecarbonitrile;

Cis-1-(1-cyclopentyl-3-ethyl-1H-indazol-6-yl)-4-hydroxycyclohexanecarbonitrile;

Cis-1-(1-cyclobutyl-3-ethyl-1H-indazol-6-yl)-4-hydroxycyclohexanecarbonitrile;

Cis-1-(1-cyclopentyl-3-ethyl-1H-indazol-6-yl)-4-hydroxy-4-methylcyclohexanecarbonitrile;

Trans-1-(1-cyclopentyl-3-ethyl-1H-indazol-6-yl)-4-hydroxy-4-methylcyclohexanecarbonitrile;
Cis-4-cyano-4-(1-cyclobutyl-3-ethyl-1H-indazol-6-yl)cyclohexanecarboxylic acid;
Trans-4-cyano-4-(1-cyclobutyl-3-ethyl-1H-indazol-6-yl)cyclohexanecarboxylic acid;
4-[3-Ethyl-1-(4-fluorophenyl)-1H-indazol-6-yl]-4-hydroxycyclohexanecarboxylic acid ethyl ester;
4-Cyano-4-[3-ethyl-1-(4-fluorophenyl)-1H-indazol-6-yl]cyclohexanecarboxylic acid ethyl ester;
4-[3-Ethyl-1-(4-fluorophenyl)-1H-indazol-6-yl]cyclohex-3-enecarboxylic acid ethyl ester;
4-Cyano-4-(1-cyclohexyl-3-ethyl-1H-indazol-6-yl)-cyclohexanecarboxylic acid ethyl ester;
Cis-4-Cyano-4-[3-ethyl-1-(4-fluorophenyl)-1H-indazol-6-yl]cyclohexanecarboxylic acid;
4-[3-Ethyl-1-(4-fluorophenyl)-1H-indazol-6-yl]cyclohex-3-enecarboxylic acid; and
4-(1-Cyclohexyl-3-ethyl-1H-indazol-6-yl)-4-hydroxycyclohexanecarboxylic acid.

11. A method according to claim 1 wherein said indazole compound is useful for treating asthma.

\* \* \* \* \*